US012390520B2

(12) United States Patent
Kallen et al.

(10) Patent No.: US 12,390,520 B2
(45) **Date of Patent: *Aug. 19, 2025**

(54) VACCINATION IN NEWBORNS AND INFANTS

(71) Applicant: CureVac SE, Tübingen (DE)

(72) Inventors: Karl-Josef Kallen, Tübingen (DE); Thomas Kramps, Tübingen (DE); Margit Schnee, Constance (DE); Benjamin Petsch, Tübingen (DE); Lothar Stitz, Rottenburg (DE)

(73) Assignee: Cure Vac SE, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/299,676

(22) Filed: Apr. 12, 2023

(65) Prior Publication Data

US 2023/0233662 A1 Jul. 27, 2023

Related U.S. Application Data

(63) Continuation of application No. 16/910,845, filed on Jun. 24, 2020, now Pat. No. 11,672,856, which is a (Continued)

(30) Foreign Application Priority Data

Mar. 2, 2011 (WO) ................. PCT/EP2011/001047

(51) Int. Cl.
*A61K 39/155* (2006.01)
*A61K 39/00* (2006.01)
(Continued)

(52) U.S. Cl.
CPC ............ *A61K 39/155* (2013.01); *A61K 39/00* (2013.01); *A61K 39/12* (2013.01); *A61K 39/145* (2013.01);
(Continued)

(58) Field of Classification Search
None
See application file for complete search history.

(56) References Cited

U.S. PATENT DOCUMENTS

| | | | |
|---|---|---|---|
| 7,709,007 | B2 | 5/2010 | Murphy et al. |
| 8,592,385 | B2 | 11/2013 | Kataoka et al. |

(Continued)

FOREIGN PATENT DOCUMENTS

| | | |
|---|---|---|
| DE | 102004035227 | 2/2006 |
| DE | 102006007433 | 8/2007 |

(Continued)

OTHER PUBLICATIONS

Fleeton et al., "Self-Replicative RNA Vaccines Elicit Protection against Influenza A Virus, Respiratory Syncytial Virus, and a Tickborne Encephalitis Virus," The Journal of Infectious Diseases, 183:1395-8 (Year: 2001).*

(Continued)

*Primary Examiner* — M Franco G Salvoza
(74) *Attorney, Agent, or Firm* — Parker Highlander PLLC

(57) ABSTRACT

The present invention relates to vaccines comprising at least one mRNA encoding at least one antigen for use in the treatment of a disease in newborns and/or infants, preferably exhibiting an age of not more than 2 years, preferably of not more than 1 year, more preferably of not more than 9 months or even 6 months, wherein the treatment comprises vaccination of the newborn or infant and eliciting an immune response in said newborn or infant. The present invention is furthermore directed to kits and kits of parts comprising such a vaccine and/or its components and to methods applying such a vaccine or kit.

47 Claims, 3 Drawing Sheets

Figure 1A:
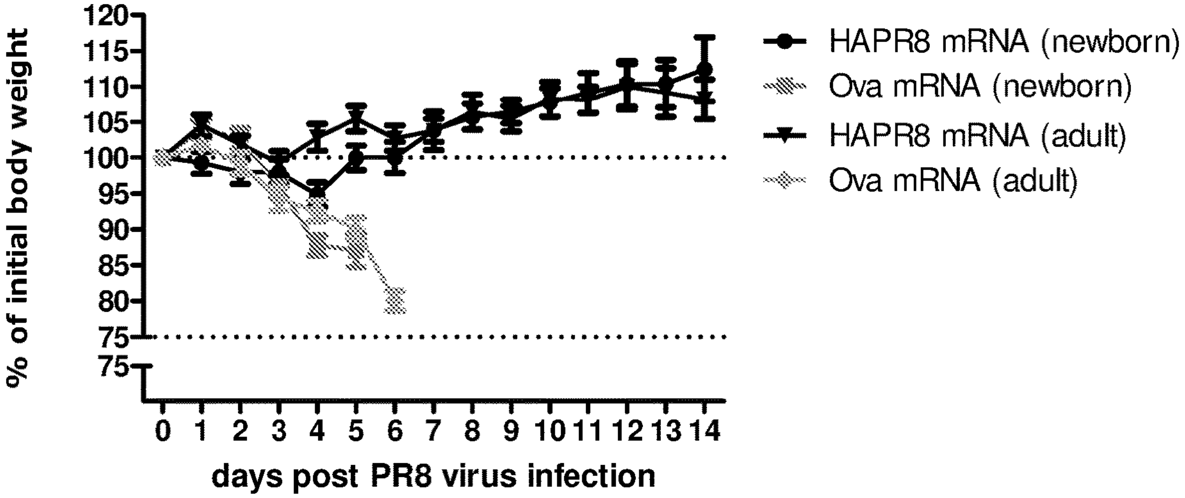

Specification includes a Sequence Listing.

Related U.S. Application Data continuation of application No. 16/273,525, filed on Feb. 12, 2019, now Pat. No. 10,729,761, which is a continuation of application No. 16/179,990, filed on Nov. 4, 2018, now Pat. No. 10,596,252, which is a continuation of application No. 15/466,308, filed on Mar. 22, 2017, now Pat. No. 10,172,935, which is a continuation of application No. 13/824,705, filed as application No. PCT/EP2012/000877 on Feb. 29, 2012, now Pat. No. 9,623,095.

(51) Int. Cl.

| | |
|---|---|
| ***A61K 39/12*** | (2006.01) |
| ***A61K 39/145*** | (2006.01) |
| ***A61K 45/06*** | (2006.01) |
| ***A61K 47/59*** | (2017.01) |
| ***A61K 47/64*** | (2017.01) |
| ***A61K 47/69*** | (2017.01) |
| ***A61P 31/16*** | (2006.01) |

(52) U.S. Cl.

CPC .............. *A61K 45/06* (2013.01); *A61K 47/59* (2017.08); *A61K 47/6455* (2017.08); *A61K 47/6921* (2017.08); *A61P 31/16* (2018.01); *A61K 2039/53* (2013.01); *A61K 2039/54* (2013.01); *A61K 2039/55* (2013.01); *A61K 2039/55583* (2013.01); *A61K 2039/572* (2013.01); *A61K 2039/575* (2013.01); *A61K 2039/6031* (2013.01); *A61K 2039/622* (2013.01); *C12N 2760/16134* (2013.01); *C12N 2760/18534* (2013.01); *C12N 2760/18571* (2013.01); *Y02A 50/30* (2018.01)

(56) References Cited

U.S. PATENT DOCUMENTS

| | | | |
|---|---|---|---|
| 9,254,265 | B2 | 2/2016 | Geall |
| 9,688,729 | B2 | 6/2017 | Kramps et al. |
| 10,017,543 | B2 | 7/2018 | Kwong et al. |
| 10,150,797 | B2 | 12/2018 | Kramps et al. |
| 11,034,729 | B2 | 6/2021 | Kramps et al. |
| 11,739,125 | B2 | 8/2023 | Kramps et al. |
| 11,911,453 | B2 | 2/2024 | Ciaramella et al. |
| 11,965,000 | B2 | 4/2024 | Kramps et al. |
| 12,097,253 | B2 | 9/2024 | Lutz et al. |
| 2005/0032730 | A1 | 2/2005 | von der Mülbe et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2007/0105193 | A1 | 5/2007 | Vilalta et al. |
| 2007/0280929 | A1 | 12/2007 | Hoerr et al. |
| 2008/0025944 | A1 | 1/2008 | Hoerr et al. |
| 2008/0171711 | A1 | 7/2008 | Hoerr et al. |
| 2008/0267873 | A1 | 10/2008 | Hoerr et al. |
| 2009/0246855 | A1 | 10/2009 | Fouchier et al. |
| 2009/0324584 | A1 | 12/2009 | Hoerr et al. |
| 2010/0048883 | A1 | 2/2010 | Ketterer et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | von der Mülbe et al. |
| 2010/0291156 | A1 | 11/2010 | Barner et al. |
| 2010/0305196 | A1 | 12/2010 | Probst et al. |
| 2011/0053829 | A1 | 3/2011 | Baumhof et al. |
| 2011/0250225 | A1 | 10/2011 | Fotin-Mleczek et al. |
| 2012/0258046 | A1 | 10/2012 | Mutzke |
| 2016/0168207 | A1 | 6/2016 | Kramps et al. |
| 2020/0197510 | A1 | 6/2020 | Ciaramella et al. |

FOREIGN PATENT DOCUMENTS

| | | |
|---|---|---|
| EP | 1083232 | 3/2001 |
| EP | 1905844 | 12/2002 |
| WO | WO 1998/019710 | 5/1998 |
| WO | WO 1998/047913 | 10/1998 |
| WO | WO 2003/059381 | 7/2003 |
| WO | WO 2003/068942 | 8/2003 |
| WO | WO 2006/046978 | 5/2006 |
| WO | WO 2007/031319 | 3/2007 |
| WO | WO 2007/069068 | 6/2007 |
| WO | WO 2007/099660 | 9/2007 |
| WO | WO 2008/014979 | 2/2008 |
| WO | WO 2008/022046 | 2/2008 |
| WO | WO 2009/030254 | 3/2009 |
| WO | WO 2009/030481 | 3/2009 |
| WO | WO 2009/079796 | 7/2009 |
| WO | WO 2009/095226 | 8/2009 |
| WO | WO 2010/037408 | 4/2010 |
| WO | WO 2010/037539 | 4/2010 |
| WO | WO 2010/088927 | 8/2010 |
| WO | WO 2010/149745 | 12/2010 |
| WO | WO 2011/026641 | 3/2011 |
| WO | WO 2012/006380 | 1/2012 |
| WO | WO 2012/013326 | 2/2012 |
| WO | WO 2012/019780 | 2/2012 |
| WO | WO 2012/037078 | 3/2012 |
| WO | WO 2012/113413 | 8/2012 |
| WO | WO 2012/158613 | 11/2012 |
| WO | WO 2013/090648 | 6/2013 |
| WO | WO 2014/160463 | 10/2014 |
| WO | WO 2015/024665 | 2/2015 |
| WO | WO 2015/199952 | 12/2015 |
| WO | WO 2017/062513 | 4/2017 |
| WO | WO 2017/070622 | 4/2017 |
| WO | WO 2017/075531 | 5/2017 |
| WO | WO 2017/172890 | 10/2017 |
| WO | WO 2018/170260 | 9/2018 |
| WO | WO 2020/123300 | 6/2020 |

OTHER PUBLICATIONS

Talaat et al., "A combination vaccine confers full protection against co-infections with influenza, herpes simplex and respiratory syncytial viruses," Vaccine 538-544 (Year: 2002).*

"150318.P1194.3.1_E20 bRSV Calf study," CureVac Presentation, 2015.

"Messenger RNA", Wikipedia, Retrieved from the Internet: URL:https://en.wikipedia.org/wiki/Messenger_RNA, accessed Apr. 13, 2016.

"The UK immunization programme", *UK NHS Green Book*, Chapter 11, 2011.

Antohi et al., "The reactivity pattern of hemagglutinin-specific clonotypes from mice immunized as neonates or adults with naked DNA," *International Immunology*, 10(4):663-668, 1998.

Arulanandam et al., "IL-12 is a potent neonatal vaccine adjuvant," *Eur. J. Immunol.*, 29:256-264, 1999.

Arulanandam et al., "Neonatal administration of IL-12 enhances the protective efficacy of antiviral vaccines," *The Journal of Immunology*, 164:3698-3704, 2000.

Belshe et al., "Live attenuated versus inactivated influenza vaccine in infants and young children," *N Engl. J. Med.*, 356:685-696, 2007.

Bettinger et al., "Peptide-mediated RNA delivery: a novel approach for enhanced transfection of primary and post-mitotic cells," *Nucleic Acids Research*, 29(18):3882-3891, 2001.

Bolhassani et al., "Improvement of different vaccine delivery systems for cancer therapy," *Molecular Cancer*, 10(1):3, 2011.

Bona, Neonatal Immunity. Humana Press: Totowa, N.J., 2005.

Bot et al., "Enhanced protection against influenza virus of mice immunized as newborns with a mixture of plasmids expressing hemagglutinin and nucleoprotein," *Vaccine*, 16(17):1675-1682, 1998.

Bot et al., "Genetic immunization of neonates," *Microbes and Infection*, 4(4):511-520, 2002.

Bot et al., "Induction of hum oral and cellular immunity against influenza virus by immunization of newborn mice with a plasmid bearing a hemagglutinin gene," *International Immunology*, 9(11):1641-1650, 1997.

Bot et al., "Protective cellular immunity against influenza virus induced by plasmid inoculation of newborn mice," *Developmental Immunology*, 5:197-210, 1998.

(56) References Cited

OTHER PUBLICATIONS

Brito et al., "Non-viral eNOS gene delivery and transfection with stents for the treatment of restenosis," *Biomed Eng*, 9:56, 2010.
Burke et al., "Extracellular barriers to in Vivo PEI and PEGylated PEI Polyplex-Mediated Gene Delivery to the Liver," *Bioconjugate Chem.*, 19(3):693-704, 2008.
Carralot et al., "Polarization of immunity induced by direct injection of naked sequence-stabilized mRNA vaccines," *Cellular and Molecular Life Sciences*, 61(18): 2418-2424, 2004.
Casciato et al., Manual of Clinical Oncology 6th edition. Lippincott Williams & Wilkins: Philadelphia, p. ix, 2009.
CDC (US), "Recommended Immunization Schedules for Persons Aged 0-18 years—United States, 2011," 2011.
Corbett et al., "Ontogeny of toll-like receptor mediated cytokine responses of human blood mononuclear cells," *PLOS One*, 5(11):e15041, 2010.
Corder et al., "A decade in review: a systematic review of universal influenza vaccines in clinical trials during the 2010 decade," *Viruses*, 12:1-22, 2020.
Cox et al., "Influenza Virus: Immunity and Vaccination Strategies. Comparison of the Immune Response to Inactivated and Live, Attenuated Influenza Vaccines," *Scand. J. Immunol.*, 59:1-15, 2004.
Danhier, "PLGA-based nanoparticles: An overview of biomedical applications," *J Control Release*, 161(2):505-22, 2012.
Deering et al., "Nucleic acid vaccines: prospects for non-viral delivery of mRNA vaccines," *Expert Opin. Drug Deliv.*, 11(6):885-899, 2014.
Deguchi et al., "Vaccination of influenza vaccine to the elderly subjects, high-risk subjects, medical care workers," *The Japanese Journal of Clinical and Experimental Medicine*, 81(12):1938-1942, 2004.
Demirjian and Levy, "Safety and efficacy of neonatal vaccination," *Eur J Immunol.*, 39(1):36-46, 2009.
Deshayes et al., "Cell-penetrating peptides: tools for intracellular delivery of therapeutics," *Cell Mol Life Sci.*, 62(16):1839-1849, 2005.
Fajac et al., "Histidylated polylysine as a synthetic vector for gene transfer into immortalized cystic fibrosis airway surface and airway gland serous cells," *J Gene Med.*, 2(5):368-78, 2000.
Foerg et al., "On the biomedical promise of cell penetrating peptides: limits versus prospects," *J Pharm Sci.*, 97(1):144-162, 2008.
Fotin-Mleczek et al., "Messenger RNA-based vaccines with dual activity induce balanced TLR-7 dependent adaptive immune responses and provide antitumor activity," *Journal of Immunotherapy*, 34(1):1-15, 2011.
Fujita et al., "Calcium enhanced delivery of tetraarginine-PEG-lipid-coated DNA/protamine complexes," *International Journal of Pharmaceutics*, 368(1-2):186-192, 2009.
Gao et al., "Nonviral gene delivery: what we know and what is next," *AAPS J.*, 9(1):E92-104, 2007.
Garinot et al., "PEGylated PLGA-based nanoparticles targeting M cells for oral vaccination," *Journal of Controlled Release*, 120(3):195-204, 2007.
Gervassi and Horton, "Is infant immunity actively suppressed or immature?" *Virology: Research and Treatment*, 5:1-9, 2014.
Giel-Peitraszuk et al., "Database Biosis, DB Acc. No. Prev199800116011," Pub Acta Biochimica Polonica, 1997.
Gravekamp et al., "Cancer vaccines in old age," *Experimental Gerontology*, 42(5):441-450, 2007.
Hamidi et al., "Pharmacokinetic consequences of pegylation," *Drug Deliv.*, 13(6):399-409, 2006.
Heil et al., "Species-specific recognition of single-stranded RNA via Toll-like receptor 7 and 8," *Science*, 303:1526-1529, 2004.
Hemmi et al., "A toll-like receptor recognizes bacterial DNA," *Nature*, 408(6813):740-745, 2000.
Hoerr et al., "In vivo application of RNA leads to induction of specific cytotoxic T lymphocytes and antibodies," *Eur. J. Immunol.*, 30(1):1-7, 2000.
Jiang et al., "SARS vaccine development," *Emerging Infectious Diseases*, 11(7):1016-1020, 2005.
Johansson et al., "Intradermal electroporation of naked replicon RNA elicits strong immune responses," *PLOS One*, 7(1):e29732, 2012.
Kim et al., "HIV vaccines—lessons learned and the way forward," *Curr Opin HIV AIDS*, 5(5):428-434, 2010.
Kovarik et al., "Optimization of vaccine responses in early life: The role of delivery systems and immunomodulators," *Immunology and Cell Biology*, 76(3):222-236, 1998.
Krieg et al., "The role of CpG dinucleotides in DNA vaccines," *Trends in Microbiology*, 6(1):23-27, 1998.
Kusters et al., "Manufacturing vaccines for an emerging viral infection—specific issues associated with the development of a prototype SARS vaccine," *Vaccines for Biodefense and Emerging and Neglected Diseases*, 147-156, 2009.
Kwok et al., "Formulation of highly soluble poly(ethylene glycol)-peptide DNA condensates," *J Pharm Sci.*, 88(10):996-1003, 1999.
Lochmann et al., "Drug delivery of oligonucleotides by peptides," *European Journal of Pharmaceutics and Biopharmaceutics*, 58(2):237-251, 2004.
Louten, "Virus structure and classification," *Essential Human Virology*, Chapter 2, 19-29, 2016.
Martin et al., "Peptide-guided gene delivery," *AAPS J.*, 9(1):E18-29, 2007.
Martinez et al., "Combining DNA and protein vaccines for early life immunization against respiratory syncytial virus in mice," *Eur. J. Immunol.*, 29:3390-3400, 1999.
Mattner, "Vaccination with Poly-I-Arginine As Immunostimulant for Peptide Vaccines: Induction of Potent and Long-Lasting T-cell Response against Cancer Antigens," *Cancer Research*, 62:14 77-1480, 2002.
Moingeon, "Strategies for designing vaccines eliciting Th1 responses in humans," *Journal of Biotechnology*, 98:189-198, 2002.
Nakamura et al., "Octaarginine-modified multifunctional envelope-type nano device for siRNA," *J Control Release*, 119(3):360-367, 2007.
National Immunisation Office (Ireland), "Previous Immunisation Schedules", 2017.
Neu et al., "Recent advances in rational gene transfer vector design based on poly(ethylene imine) and its derivatives," *J Gene Med.*, 7(8):992-1009, 2005.
Office Action issued in U.S. Appl. No. 13/824,705, mailed Feb. 27, 2015.
Office Action issued in U.S. Appl. No. 13/824,705, mailed Jul. 31, 2014.
Office Action issued in U.S. Appl. No. 13/824,705, mailed Nov. 19, 2015.
Office Action issued in U.S. Appl. No. 15/437,405, mailed Apr. 19, 2018.
Office Action issued in U.S. Appl. No. 15/466,308, mailed Feb. 8, 2018.
Office Action issued in U.S. Appl. No. 16/179,990, mailed Jun. 3, 2019.
Office Action issued in U.S. Appl. No. 16/179,990, mailed Sep. 19, 2019.
Office Action issued in U.S. Appl. No. 16/273,525, mailed Aug. 8, 2019.
Office Action issued in U.S. Appl. No. 16/273,525, mailed Mar. 21, 2019.
Office Action issued in U.S. Appl. No. 16/273,525, mailed Nov. 29, 2019.
Office Action issued in U.S. Appl. No. 16/910,845, mailed Jun. 9, 2022.
Office Action issued in U.S. Appl. No. 16/910,845, mailed Sep. 20, 2021.
Office Action issued in U.S. Appl. No. 17/067,709, mailed Dec. 29, 2023.
Office Action issued in U.S. Appl. No. 17/067,709, mailed Jul. 19, 2022.
Office Action issued in U.S. Appl. No. 17/067,709, mailed Jul. 14, 2021.
Office Action issued in U.S. Appl. No. 17/067,709, mailed Mar. 10, 2021.

(56) References Cited

OTHER PUBLICATIONS

Office Action issued in U.S. Appl. No. 17/067,709, mailed May 4, 2023.
Office Action issued in U.S. Appl. No. 17/090,885, mailed Feb. 18, 2021.
Ohfuji et al., "Target groups of influenza vaccination," *Japanese Journal of Public Health*, 54(6):361-367, 2007.
Opposition to European Patent No. EP 2680880 by Strawman Limited, filed Dec. 18, 2017.
Oupicky et al., "Importance of lateral and steric stabilization of polyelectrolyte gene delivery vectors for extended systemic circulation," *Mol Ther.*, 5(4):463-72, 2002.
Oupicky et al., "Laterally stabilized complexes of DNA with linear reducible polycations: strategy for triggered intracellular activation of DNA delivery vectors," *J Am Chem Soc.*, 124(1):8-9, 2002.
Parker et al., "Enhanced gene transfer activity of peptide-targeted gene-delivery vectors," *J Drug Target*, 13(1):39-51, 2005.
Pascolo, "Vaccination with messenger RNA (mRNA)," *Toll-Like Receptors (TLRs) and Innate Immunity*, 183:221-235, 2008.
Perlman et al., "Immunopathogenesis of coronavirus infections; implications for SARS," *Nature Reviews Immunology*, 5:917-927, 2005.
Petsch et al., "Protective efficacy of in vitro synthesized, specific mRNA vaccines against influenza A virus infection," *Nature Biotechnology*, 30(12):1210-1216, 2012.
Petsch, Declaration Under 37 C.F.R. § 1.132, submitted in U.S. Appl. No. 13/824,705, executed Jul. 27, 2015.
Petsch, Declaration Under 37 C.F.R. § 1.132, submitted in U.S. Appl. No. 15/466,308, executed Jun. 8, 2018.
Philbin et al., "Developmental Biology of the Innate Immune Response: Implications for Neonatal and Infant Vaccine Development," *Pediatric Research*, 65:98R-105R, 2009.
Pichon et al., "Poly[Lys-(AEDTP)]: A cationic polymer that allows dissociation of pDNA/cationic polymer complexes in a reductive medium and enhances polyfection," *Bioconjug Chem.*, 13(1 ):76-82, 2002.
Pomroy et al., "Solubilization of hydrophobic peptides by reversible cysteine PEGylation," *Biochem Biophys Res Commun.*, 245(2):618-21, 1998.
Radu et al., "Plasmid expressing the influenza HA gene protects old mice from lethal challenge with influenza virus," *Viral Immunology*, 12(3):217-226, 1999.
Read et al., "A versatile reducible polycation-based system for efficient delivery of a broad range of nucleic acids," *Nucleic Acids Res.*, 33(9):e86, 2005.
Read et al., "RNA-based therapeutic strategies for cancer," *Expert Opinion on Therapeutic Patents*, 13(5):627-638, 2003.
Read et al., "Vectors based on reducible polycations facilitate intracellular release of nucleic acids," *J Gene Med.*, 5(3):232-45, 2003.
Sakae et al., "Highly efficient in vivo gene transfection by plasmid/PEI complexes coated by anionic PEG derivatives bearing carboxyl groups and RGD peptide," *Biomedicine and Pharmacotherapy*, 62(7):448-453, 2008.
Sarzotti et al., "Induction of protective CTL responses in newborn mice by a murine retrovirus," *Science*, 271(5256):1726-1728, 1996.
Scheel et al., "Therapeutic anti-tumor immunity triggered by injections of immunostimulating single-stranded RNA," *Eur J Immunol*, 36(10):2807-2816, 2006.
Scheel et al., "Toll-like receptor-dependent activation of several human blood cell types by protamine-condensed mRNA," *Eur J Immunol*, 35(5):1557-1566, 2005.
Shiffman et al., "Protein dissociation from DNA in model systems and chromatin," *Nucleic Acids Res.*, 5(9):3409-26, 1978.
Smith et al., "Identification of common biological pathways and drug targets across multiple respiratory viruses based on human host gene expression analysis," *PLoS One*, 7(3):e33174, 2012.
Sugaya, "Influenza vaccine", *The Journal of Pediatric Practice*, 67(11): 1913-1918, 2004.
Takae et al., "PEG-detachable polyplex micelles based on disulfide-linked block catiomers as bioresponsive nonviral gene vectors," *J Am Chem Soc.*, 130(18):6001-6009, 2008.
Third Party Observation issued in U.S. Appl. No. 15/015,458, mailed on Sep. 1, 2017.
Third Party Observation issued in U.S. Appl. No. 15/437,405, mailed on Oct. 20, 2017.
Third Party Observation issued in U.S. Appl. No. 15/452,658, mailed on Sep. 1, 2017.
Third Party Observation issued in U.S. Appl. No. 15/466,308, mailed on Oct. 20, 2017.
Thompson and Locarnini, "Toll-like receptors, RIG-I-like RNA helicases and the antiviral innate immune response," *Immunology and Cell Biology*, 85(6):435-445, 2007.
Tönges et al., "Stearylated octaarginine and artificial virus-like particles for transfection of siRNA into primary rat neurons," *RNA*, 12(7):143 1-8, 2006.
UNICEF, "Immunization Summary: A statistical reference containing data through 2011," 2013.
Unnamalai et al., "Cationic oligopeptide-mediated delivery of dsRNA for post-transcriptional gene silencing in plant cells," *FEBS Lett.*, 566(1-3):307-10, 2004.
Vives et al., "A truncated HIV-1 Tat protein basic domain rapidly translocates through the plasma membrane and accumulates in the cell nucleus," *J Biol Chem.*, 272(25):16010-16017, 1997.
Wang et al., "An intracellular delivery method for siRNA by an arginine-rich peptide," *J Biochem Biophys Methods.*, 70(4):579-86, 2007.
Widman et al., "RepliVAX WN, a single-cycle flavivirus vaccine to prevent West Nile disease, elicits durable protective immunity in hamsters," *Vaccine*, 27(41):5550-5553, 2009.
Wilschut, "Influenza vaccines: the virosome concept," *Immunology Letters*, 122:118-121, 2009.
Wong et al., "An mRNA vaccine for influenza," *Nature Biotechnology*, 30(12):1202-1204, 2012.
Yoshitomi et al., "Design of core—shell-type nanoparticles carrying stable radicals in the core," *Biomacromolecules*, 10:596-601, 2009.
Yu et al., "A new insight into hepatitis C vaccine development," *J Biomed Biotechnol.*, 2010.
Zhang et al., "Delivery of Telomerase Reverse Transcriptase Small Interfering RNA in Complex with Positively Charged Single-Walled Carbon Nanotubes Suppresses Tumor Growth," *Clinical Cancer Research*, 12:4933-4939, 2006.
Zhang et al., "Type I interferons protect neonates from acute inflammation through interleukin 10-producing B cells," *J Exp. Med.*, 204(5):1107-1118, 2007.
Zohra et al., "Effective delivery with enhanced translational activity synergistically accelerates mRNA-based transfection," *Biochem Biophys Res Commun.*, 358(1):373-378, 2007.
Agenbach et al., "Amino Acid Variation within the Fusion Protein of Respiratory Syncytial Virus Subtype A and B Strains during Annual Epidemics in South Africa", *Virus Genes*, 30(2):267-278, 2005.
Anderson et al., "Strategic priorities for respiratory syncytial virus (RSV) vaccine development," *Vaccine*, 31S:B209-B215, 2013.
Cohen, "'Safety signal' in Moderna's RSV vaccine studies halts trials of other vaccines for childhood killer," Science Insider, Dec. 13, 2024. (4 pages).
De Baets et al., "Recombinant influenza virus carrying the respiratory syncytial virus (RSV) F85-93 CTL epitope reduces RSV replication in mice," *Journal of Virology*, 87(6):3314-3323, 2013.
Geall et al., "Nonviral delivery of self-amplifying RNA vaccines," *Proc Natl Acad Sci USA*, 109:14604-14609, 2012.
GenBank Accession No. EF566942, 2007, p. 1-2.
Hashimoto et al., "Neutralizing epitopes of RSV and palivizumab resistance in Japan", *Fukushima J. Med. Sci.*, 63(3):127-134, 2017.
Hause et al., "Sequence variability of the respiratory syncytial virus (RSV) fusion gene among contemporary and historical genotypes of RSV/A and RSV/B", *PLoS One*, 12(4):e0175792, 2017.
Higgins et al., "Advances in RSV vaccine research and development—A global agenda," *Vaccine*, 34(26):2870-2875, 2016.

(56) References Cited

OTHER PUBLICATIONS

Johnstone et al., "Shifting immunodominance pattern of two cytotoxic Tlymphocyte epitopes in the F glycoprotein of the Long strain of respiratory syncytial virus", *J. Gen. Virol.*, 85(11):3229-3238, 2004.
Joyce et al., "Iterative structure-based improvement of a fusion-glycoprotein vaccine against RSV," Nature Structural & Molecular Biology, 23:811-820, 2016.
McLellan et al., "Structure and Function of Respiratory Syncytial Virus Surface Glycoproteins", *Curr. Top. Microbiol. Immunol.*, 372:83-104, 2014.
McLellan et al., "Structure of RSV fusion glycoprotein trimer bound to a prefusion-specific neutralizing antibody," *Science*, 340:1113-1117, 2013.
McLellan et al., "Structure-based design of a fusion glycoprotein vaccine for respiratory syncytial virus," *Science*, 342(6158):592-598, 2013.
Mottram et al., "Type 1 and 2 immunity following vaccination is influenced by nanoparticle size: formulation of a model vaccine for respiratory syncytial virus," *Molecular Pharmaceutics*, 4(1):73-84, 2007.
Oomens et al., "The cytoplasmic tail of the human respiratory syncytial virus F protein plays critical roles in cellular localization of the F protein and infectious progeny production," *Journal of Virology*, 80(21):10465-10477, 2006.
Pierantoni et al., "Mucosal delivery of a vectored RSV vaccine is safe and elicits protective immunity in rodents and nonhuman primates," *Molecular Therapy—Methods & Clinical Development*, 2:15018, 2015.
Schlake et al., "Developing mRNA-vaccine technologies," *RNA Biology*, 9(11):1319-1330, 2012.
Ternette et al. "Expression of RNA virus proteins by RNA polymerase II dependent expression plasmids is hindered at multiple steps," Virology Journal, 4:51, 2007, p. 1-10.
Turner et al., "A novel influenza virus hemagglutinin-respiratory syncytial virus (RSV) fusion protein subunit vaccine against influenza and RSV," *Journal of Virology*, 87(19):10792-10804, 2013.

* cited by examiner

PR8 H1 mRNA

AUGAAGGCCAACCUGCUCGUGCUGCUGUGCGCCCUCGCGGCCGCCGACGCCGA
CACCAUCUGCAUCGGCUACCACGCCAACAACAGCACCGACACGGUCGACACCG
UGCUGGAGAAGAACGUGACCGUCACCCACUCCGUGAACCUGCUCGAGGACAGC
CACAACGGGAAGCUGUGCCGGCUGAAGGGCAUCGCGCCCCUCCAGCUGGGGAA
GUGCAACAUCGCCGGCUGGCUGCUCGGGAACCCGGAGUGCGACCCCCUGCUGC
CCGUGCGCUCCUGGAGCUACAUCGUCGAGACGCCCAACUCCGAGAACGGCAUC
UGCUACCCGGGCGACUUCAUCGACUACGAGGAGCUCCGGGAGCAGCUGAGCUC
CGUGAGCUCCUUCGAGCGCUUCGAGAUCUUCCCCAAGGAGAGCUCCUGGCCCA
ACCACAACACCAACGGGGUGACCGCCGCCUGCAGCCACGAGGGCAAGUCCAGC
UUCUACCGGAACCUGCUCUGGCUGACCGAGAAGGAGGGGUCCUACCCCAAGCU
GAAGAACAGCUACGUCAACAAGAAGGGCAAGGAGGUGCUCGUGCUGUGGGGA
UCCACCACCCGCCCAACUCCAAGGAGCAGCAGAACCUGUACCAGAACGAGAAC
GCGUACGUCAGCGUGGUGACGUCCAACUACAACCGCCGGUUCACCCCCGAGAU
CGCCGAGCGCCCCAAGGUCCGGGACCAGGCCGGCCGCAUGAACUACUACUGGA
CCCUCCUGAAGCCGGGCGACACCAUCAUCUUCGAGGCCAACGGGAACCUGAUC
GCCCCGAUGUACGCGUUCGCCCUCAGCCGGGGCUUCGGGAGCGGCAUCAUCAC
GUCCAACGCCAGCAUGCACGAGUGCAACACCAAGUGCCAGACCCCCCUGGGCG
CCAUCAACUCCAGCCUGCCCUACCAGAACAUCCACCCGGUGACCAUCGGGGAG
UGCCCCAAGUACGUGCGCUCCGCCAAGCUCCGGAUGGUCACGGGCCUGCGCAA
CAACCCCAGCAUCCAGUCCCGGGGGCUGUUCGGCGCGAUCGCCGGGUUCAUCG
AGGGCGGCUGGACCGGGAUGAUCGACGGCUGGUACGGGUACCACCACCAGAAC
GAGCAGGGCAGCGGGUACGCCGCCGACCAGAAGUCCACCCAGAACGCCAUCAA
CGGCAUCACCAACAAGGUGAACACGGUGAUCGAGAAGAUGAACAUCCAGUUCA
CCGCGGUCGGCAAGGAGUUCAACAAGCUCGAGAAGCGCAUGGAGAACCUGAAC
AAGAAGGUGGACGACGGGUUCCUGGACAUCUGGACCUACAACGCCGAGCUCCU
GGUGCUGCUCGAGAACGAGCGGACCCUGGACUUCCACGACAGCAACGUCAAGA
ACCUGUACGAGAAGGUGAAGUCCCAGCUCAAGAACAACGCCAAGGAGAUCGGC
AACGGGUGCUUCGAGUUCUACCACAAGUGCGACAACGAGUGCAUGGAGAGCGU
CCGCAACGGCACGUACGACUACCCCAAGUACUCCGAGGAGAGCAAGCUGAACC
GGGAGAAGGUGGACGGGGUGAAGCUGGAGUCCAUGGGCAUCUACCAGAUCCUC
GCCAUCUACAGCACCGUCGCCUCCAGCCUGGUGCUGCUGGUGUCCCUCGGCGC
GAUCAGCUUCUGGAUGUGCAGCAACGGGUCCCUGCAGUGCCGCAUCUGCAUCU
GA

Elements in 3'UTR of mRNAs: alpha goblin 3'UTR, poly A, poly C
Vector used: pCV19

FIG. 1B

Ovalbumin (control) mRNA

AUGGGCAGCAUCGGGGCCGCGUCGAUGGAGUUCUGCUUCGACGUGUUCAAGGA
GCUGAAGGUCCACCACGCCAACGAGAACAUCUUCUACUGCCCGAUCGCCAUCA
UGAGCGCGCUCGCCAUGGUGUACCUGGGCGCCAAGGACAGCACCCGGACGCAG
AUCAACAAGGUGGUCCGCUUCGACAAGCUGCCCGGCUUCGGGGACUCGAUCGA
GGCGCAGUGCGGCACCAGCGUGAACGUGCACAGCUCGCUCCGGGACAUCCUGA
ACCAGAUCACCAAGCCGAACGACGUCUACAGCUUCAGCCUGGCCUCGCGGCUC
UACGCCGAGGAGCGCUACCCGAUCCUGCCCGAGUACCUGCAGUGCGUGAAGGA
GCUCUACCGGGGCGGGCUGGAGCCGAUCAACUUCCAGACGGCGGCCGACCAGG
CCCGGGAGCUGAUCAACAGCUGGGUGGAGAGCCAGACCAACGGCAUCAUCCGC
AACGUCCUCCAGCCGUCGAGCGUGGACAGCCAGACCGCGAUGGUGCUGGUCAA
CGCCAUCGUGUUCAAGGGCCUGUGGGAGAAGACGUUCAAGGACGAGGACACCC
AGGCCAUGCCCUUCCGGGUGACCGAGCAGGAGUCGAAGCCGGUCCAGAUGAUG
UACCAGAUCGGGCUCUUCCGGGUGGCGAGCAUGGCCAGCGAGAAGAUGAAGAU
CCUGGAGCUGCCGUUCGCCUCGGGCACGAUGAGCAUGCUCGUGCUGCUGCCCG
ACGAGGUCAGCGGCCUCGAGCAGCUGGAGUCGAUCAUCAACUUCGAGAAGCUG
ACCGAGUGGACCAGCAGCAACGUGAUGGAGGAGCGCAAGAUCAAGGUGUACCU
CCCGCGGAUGAAGAUGGAGGAGAAGUACAACCUGACGUCGGUCCUGAUGGCGA
UGGGGAUCACCGACGUGUUCAGCAGCUCGGCCAACCUCAGCGGCAUCAGCUCG
GCCGAGAGCCUGAAGAUCAGCCAGGCGGUGCACGCCGCCCACGCGGAGAUCAA
CGAGGCCGGCCGGGAGGUCGUGGGGUCGGCCGAGGCGGGCGUGGACGCCGCCA
GCGUCAGCGAGGAGUUCCGCGCGGACCACCCGUUCCUGUUCUGCAUCAAGCAC
AUCGCCACCAACGCCGUGCUCUUCUUCGGCCGGUGCGUGUCGCCCUGA

Elements in 3’UTR of mRNAs: alpha goblin 3’UTR, poly A, poly C
Vector used: pCV19

FIG. 1C

VACCINATION IN NEWBORNS AND INFANTS

This application is a continuation of U.S. application Ser. No. 16/910,845, filed Jun. 24, 2020, which is a continuation of U.S. application Ser. No. 16/273,525, filed Feb. 12, 2019, now U.S. Pat. No. 10,729,761, which is a continuation of U.S. application Ser. No. 16/179,990, filed Nov. 4, 2018, now U.S. Pat. No. 10,596,252, which is a continuation of U.S. application Ser. No. 15/466,308, filed Mar. 22, 2017, now U.S. Pat. No. 10,172,935, which is a continuation of U.S. application Ser. No. 13/824,705, filed Jul. 10, 2013, now U.S. Pat. No. 9,623,095, which is a national phase application under 35 U.S.C. § 371 of International Application No. PCT/EP2012/000877, filed Feb. 29, 2012, which claims benefit of International Application No. PCT/EP2011/001047, filed Mar. 2, 2011, the entire contents of each of which are hereby incorporated by reference.

This application contains a Sequence Listing XML, which has been submitted electronically and is hereby incorporated by reference in its entirety. Said Sequence Listing XML, created on Apr. 12, 2023, is named CRVCP0101USC7.xml and is 401,949 bytes in size.

The present invention relates to vaccines comprising at least one mRNA encoding at least one antigen for use in the treatment of a disease in newborns and/or infants, preferably exhibiting an age of not more than 2 years, preferably of not more than 1 year, more preferably of not more than 9 months or even 6 months, wherein the treatment comprises vaccination of the newborn or infant and eliciting an immune response in said newborn or infant. The present invention is furthermore directed to kits and kits of parts comprising such a vaccine and/or its components and to methods applying such a vaccine or kit.

Diagnosing, preventing and treating infections and allergies in newborns and infants are of major interest and increasingly the subject of intense research worldwide. In this context, a profound knowledge about the mechanisms of the immune system of newborns and infants is of major importance. As widely known, the primary role of the immune system is to protect the organism against pathogens, but the response of the immune system to such pathogens is not equal throughout the whole life span. It is further known that responses of the immune system undergo age-associated alterations. Likewise, responses of the immune system of newborns and infants are not equal to those of adults. Particularly the response of T and B cells differs in many aspects, a fact, which may be contributed to the necessity of the prenatal requirements of the fetal immune system and the transition to the external conditions during birth.

As is well known, all organ systems of the body undergo a dramatic transition during birth from a sheltered intra-uterine existence to the radically distinct environment of the outside world. This acute transition is then followed by a gradual, age-dependent maturation. As reviewed by Ofer (see Ofer, NATURE REVIEWS| IMMUNOLOGY VOLUME 7|MAY 2007|379) the fetal and neonatal immune systems are usually associated with physiological demands that are three-fold: protection against infection, including viral and bacterial pathogens at the maternal-fetal interface, avoidance of potentially harmful pro-inflammatory/T helper 1 (Th1)-cell polarizing responses that can induce alloimmune reactions between mother and fetus, and mediation of the transition between the normally sterile intra-uterine environment to the foreign antigen-rich environment of the outside world, including primary colonization of the skin and intestinal tract by microorganisms. Given the limited exposure to antigens in utero and the well-described defects in neonatal adaptive immunity, newborns must rely on their innate immune systems for protection to a significant extent. As the innate immune system can instruct the adaptive immune response, distinct functional expression of neonatal innate immunity, including a bias against Th1-cell-polarizing cytokines, contributes to a distinct pattern of neonatal adaptive immune responses. Mounting evidence indicates that infection-induced production of pro-inflammatory/Th1 cell-polarizing cytokines, including tumour-necrosis factor (TNF) and interleukin-1β (IL-1β), is associated with premature labour and pre-term delivery. In particular, TNF production is thought to favour abortion through the induction of apoptosis in placental and fetal cells. The ability of proinflammatory cytokines to induce spontaneous abortion is likely to be an important reason for the strong bias of the maternal and fetal immune systems of multiple mammalian species towards TH2-cell-polarizing cytokines (see Levy, 2007, supra).

Because of this impaired production of Th1 cell associated cytokines, it was initially thought that the neonatal innate immune system was generally impaired or depressed; however, stimulus-induced production of certain cytokines (for example, IL-6, IL-10 and IL-23) by neonatal monocytes and antigen presenting cells (APCs) actually exceeds that of adults (see Angelone, D. et al., *Pediatr. Res.* 60, 205-209 (2006); Vanden Eijnden, S., Goriely, S., De Wit, D., Goldman, M. & Willems, F. *Eur. J. Immunol.* 36, 21-26, (2006); Chelvarajan, R. L. et al., *J. Leukoc. Biol.* 75, 982-994 (2004)). Nevertheless, there still appears to be a bias against Th1 cell-polarizing cytokines, which leaves the newborn susceptible to microbial infections and contributes to the impairment of neonatal immune responses to most vaccines, thereby frustrating efforts to protect this vulnerable population. After birth, there is an age-dependent maturation of the immune response. Of note, prenatal and postnatal exposure to environmental microbial products that can activate innate immunity might accelerate this maturation process, particularly if the exposure occurs repeatedly over time, diminishing TH2-cell polarization and/or enhancing Th1 cell polarization and thereby potentially reducing allergy and atopy, in accord with the hygiene hypothesis (see again Levy, 2007, supra).

T cell mediated immune responses in early life, particularly in newborns, have been reviewed by Marchant and Goldmann (see Marchant and Goldmann, Clinical and Experimental Immunology, 2005, 14: 10-18). As stated there circulating neonatal T lymphocytes are fundamentally different from naïve adult T cells and have characteristics of recent thymic emigrants. They contain high concentrations of T cell-receptor excision circles (TRECs), episomal DNA by products of TCRα-chain rearrangement that are not replicated but diluted during cell division. Like adult naïve cells, most neonatal T lymphocytes express the CD45 $RA^+$ isoform and the costimulatory molecules CD27 and CD28. In contrast to adult naïve lymphocytes, neonatal lymphocytes express the CD38 molecule. In addition, a high proportion of circulating neonatal T cells are in cycle and display an increased susceptibility to apoptosis indicating high cell turn-over. Proliferation of naïve T lymphocytes can also be detected during fetal life and could last up to five years of age. The high cell turn-over observed in early life probably plays a central role in the establishment of the T cell repertoire. Despite their high turn-over, T cells preserve long telomeric sequences through a high constitutive telomerase activity. In vitro apoptosis of neonatal T lymphocytes can be prevented by cytokines signalling through the γ-chain of the IL-2 receptor, namely IL-2, IL-4, IL-7 and IL-15. Among these cytokines, IL-7 and IL-15 also induce the proliferation of neonatal T lymphocytes in the absence of other stimuli. IL-7 is involved in thymocyte development at a stage preceding the T cell receptor rearrangement. IL-15 preferentially stimulates the proliferation of CD8 rather than CD4+ T cells. In contrast to IL-7, IL-15 induces the differentiation of CD8+T lymphocytes in vitro (see Marchant and Goldmann, 2005, supra).

Several mechanisms limit T helper 1 (Th1) type responses in early life. In utero, Th1 responses are toxic to the placenta and are inhibited by trophoblast-derived IL-10 and progesterone. At birth, Th1 responses are still of lower magnitude than later in life. In vitro, CD4+ T cells of newborns produce lower levels of IFNγ than naïve T cells of adults and are hypermethylated at CpG and non-CpG sites within the IFNγ promoter. In the presence of suboptimal CD28 costimulation, IL-12 stimulates the production of both IL-4 and IFNγ by neonatal CD4 T lymphocytes whereas adult cells do not produce IL-4 under similar conditions. In response to polyclonal or superantigen activation, postnatal thymocytes develop into Th2 cytokine producing CD4 cells whereas IL12 is required to stimulate the production of IFNγ. In contrast, neonatal CD8+ T cells produce similar levels of IFNγ and have a pattern of IFNγ promoter methylation comparable to that of naïve adult cells. In addition, neonatal CD8 T lymphocytes are strictly dependent on the presence of IL-4 at the time of priming to differentiate into IL-4-producing cells. The capacity of neonatal CD4 T lymphocytes to express CD40 ligand (CD154), a molecule playing a critical role in the help to B lymphocytes and CD8+ T cells, remains controversial (see also Marchant and Goldmann, 2005, supra).

Together, the available data indicate that naïve T lymphocytes are differently programmed in neonates and in adults. As may be summarized, the capacity of neonatal CD4+ T cells to produce IFNγ and of neonatal DCs to promote Th1 responses is lower as compared to adults in in vitro studies. Additionally, Th1 responses to a number of vaccines and infectious pathogens in vivo are poor during early life. However, mature Th1 responses can develop in certain conditions such as neonatal BCG vaccination and *Bordetella pertussis* infection, probably in relation with a more efficient activation of DCs. Accordingly, the classical paradigm that newborns have incompetent T lymphocytes developing only weak or even tolerogenic responses has to be reconsidered. The observation that mature cellular immune responses can be developed in early life suggests that under appropriate conditions of stimulation neonatal T lymphocytes may be instructed to fight intracellular pathogens (see also Marchant and Goldmann, 2005, supra).

Not only differences in T cell responses but also differences in B cell responses appear to exhibit a severe impact on immunoprotection in newborns and/or infants with respect to adult individuals. It has long been thought that the vulnerability of children younger than 18-24 months of age to encapsulated bacteria such as pneumococcus, *Haemophilus influenzae* B (Hib) and meningococcus has long been thought to reflect a general failure to generate T cell-independent B cell responses to most bacterial polysaccharides (see Claire-Anne Siegrist* and Richard Aspinall, NATURE REVIEWS| IMMUNOLOGY VOLUME 9|MARCH 2009|185). However, immaturity of the immune system in newborns and/or infants also has a direct effect on the magnitude of antibody responses to T cell-dependent protein antigens. Mechanisms that shape B cell responses in early life were investigated using neonatal mouse immunization models that were developed to reproduce the main limitations of immune responses to vaccines that are administered at an early age (see Claire-Anne Siegrist* and Richard Aspinall, 2009, supra). There are numerous differences between neonatal and adult mouse splenic B cells, although fewer differences have been identified by comparing human peripheral B cells. Specifically, human neonatal B cells express lower levels of the co-stimulatory molecules CD40, CD80 and CD86, which decreases their responses to CD40 ligand (CD40L) and interleukin-10 (IL-10) expressed by T cells. Splenic marginal zone infant B cells express lower levels of CD21, which limits their capacity to respond to polysaccharide-complement complexes. The expression of TACI (transmembrane activator and calcium-modulating cyclophilin-ligand interactor; also known as TNFRSF13B), an important co-stimulatory receptor, is also decreased on both neonatal mouse and neonatal human B cells, particularly those born prematurely. In addition, B cell responses in early life are influenced by numerous extrinsic factors. Antibodies of maternal origin bind to vaccine antigens in an epitope specific manner and therefore prevent infant B cells from accessing immunodominant vaccine epitopes. Furthermore, human and mouse neonates have low levels of serum complement component C3, which limits their responses to antigen-C3d complexes. The human spleen contains fewer marginal zone macrophages (which have a crucial role in the induction of an antibody response through the trapping of particulate antigens) in neonates than in adults, and the cells differ in their capacity to produce cytokines. In infant mice, B cell responses are limited by a marked delay in the maturation of the follicular dendritic cell (FDC) network, resulting from the failure of FDC precursors to respond to B cell-mediated lymphotoxin-α signalling. FDCs nucleate germinal centre reactions by attracting antigen-specific B cells, retain antigens in the form of immune complexes that are highly stimulatory to B cells and provide signals that lead to somatic hypermutation and class-switch recombination. The immaturity of the FDC network therefore delays the induction and limits the magnitude of germinal centre responses, even when potent adjuvants that induce adult-like B cell, T cell and DC activation patterns are used. Additional to the postnatal maturation of antibody responses, the antibody persistence in vivo exhibits an important effect. The long-term maintenance of specific antibodies with a short half-life requires the persistence of antibody-producing B cells, which can either be continually produced from a pool of memory B cells or can persist as long-lived plasma cells. Antibody mediated depletion of memory B cells, which does not affect plasma cells, has shown that the plasma-cell stage is independent of the memory B cell pool. It has also been shown, that persistence of antibodies in vivo may be influenced by environmental factors. This supports the hypothesis that the limited persistence of antibody responses in early life results from exposure to a large load of environmental antigens, which results in competition for access to a limited set of plasma-cell survival niches in the bone marrow (see Claire-Anne Siegrist* and Richard Aspinall, 2009, supra).

As known before, the administration of a single dose of vaccine at birth can fail to elicit specific antibodies while priming for subsequent secondary responses, which indicates a preferential neonatal differentiation pathway towards memory B cells rather than plasma cells. Several factors seem to contribute to this B cell differentiation pattern. The fate of antigen-specific naive B cells and their differentiation to short-lived plasma cells, long-lived plasma cells or memory B cells is controlled by early B cell activation signals. High-affinity B cells are actively recruited to the plasma-cell pool, whereas moderate-affinity B cells remain as memory B cells in the secondary lymphoid organs. So, decreased initial B cell receptor affinity and/or delayed affinity maturation of neonatal naive B cells might decrease the strength of the signal and favour memory B cell differentiation.

The limited expression of CD21 by infant B cells also supports the generation of memory B cells and impairs the development of plasma cells, which would be supported by CD40-mediated signalling, cytokines such as I1-21 and interactions with ligands such as B cell activating factor (BAFF; also known as TNFSF13B) and APRIL. Remarkably, these plasma-cell-supporting factors are all expressed at low levels early in life, unless additional activation signals are provided to enhance DC and T cell activation. Furthermore, early-life B cells might have to compete for limited resources within the germinal centre, which impairs antibody responses. Plasma-cell differentiation may thus be 'forced' in early life by providing additional DC activation signals.

Therefore, a combination of factors appears to result in the preferential differentiation of early-life B cells towards memory B cells instead of long-lived plasma cells in a pattern. Importantly, although it has been shown that the memory B cell pool can be formed early in life, this should not be considered as evidence that its magnitude or persistence is similar to that elicited in immunologically mature hosts. Recent observations of the failure of booster vaccines to elicit a memory response in adolescents or young adults that had been primed against hepatitis B virus in infancy suggest that infant-triggered memory B cells might not last life long. Whether this reflects a smaller B cell pool in infants and/or the influence of as yet undefined homeostatic factors remains to be determined. In summary, a large number of B cell intrinsic factors and extrinsic determinants appear to cooperate to limit the induction and the persistence of antibody-secreting plasma cells in early life, while supporting the preferential induction of memory B cell responses (see Claire-Anne Siegrist* and Richard Aspinall, 2009, supra).

Alterations in T cell responses and also in B cell responses as discussed above exhibit a significant effect not only on immunoprotection towards pathogens but also to vaccination strategies in newborns and/or infants when combating infectious diseases but possibly also allergies, autoimmune disorders or further diseases. Many attempts have been carried out to provide efficient vaccines, which may overcome at least some of the above limitations.

One previous approach to overcome theses deficiencies in the context of virus-based influenza vaccines refers to the administration of naked DNA plasmid (pHA) expressing hemagglutinin (HA) from the neurovirulent strain A/WSN/33 of influenza virus to prime protective immune responses by inoculating newborn and adult mice (see Bot et al, 1997, *International Immunology, Vol.* 9, *No.* 11, pp. 1641-1650). As shown by Bot et al. (1997) continuous exposure to small doses of antigen subsequent to neonatal DNA immunization may lead to priming of specific B and Th cells, rather than tolerance induction. However, only pHA immunization of adult mice primed a strongly biased Th1 response, whereas in neonates it induced a mixed Th1/Th2 response. One further very similar approach of the same working group was directed to the combined administration of plasmids expressing nucleoprotein (NP) or hemagglutinin (HA) of influenza virus. Neonatal immunization of BALB/c mice was followed by priming of B cells, Th cells and CTL rather than tolerance (see Bot et al., Vaccine, Vol. 16, No. 17, pp. 16751682, 1998). However, protection in terms of survival against lethal challenge with homologous or heterologous strains was not reported to be complete. Further, in the case of NP expressing plasmid, the protective immunity elicited by neonatal immunization required a longer time to develop, as compared with adult immunization. Neither Bot et al. (1997, supra) nor Bot et al. (1998, supra) showed good Th1 responses in neonates. Furthermore, even though it was stressed in both papers that DNA vaccination represents an efficient and safe means to generate broad humoral and cellular immune responses to influenza viruses during the earliest stages of postnatal life, DNA has been encountered meanwhile as dangerous due to unwanted insertion into the genome. Such DNA based vaccinations may even lead to interruption of functional genes and cancer or the formation of anti-DNA antibodies and are therefore out of focus as of today.

Further approaches were directed to improvement of delivery systems and administration of immunomodulators to optimize vaccine responses in early life. Jiri Kovarik and Claire-Anne Siegrist focus on problems arising from the attempt to vaccinate against pathogens very early in life and on the role of selective adjuvants that could be used to: (i) rapidly induce strong antibody responses of the appropriate isotypes; (ii) elicit sustained antibody responses extending beyond infancy; (iii) induce efficient Th1 and CTL responses in spite of the preferential Th2 polarization of early life responses; (iv) escape from maternal antibody mediated inhibition of vaccine responses; (v) show acceptable reactogenicity in early life; and (vi) allow incorporation of several vaccine antigens into a single formulation so as to reduce the number of required injections (see Jiri Kovarik and Claire-Anne Siegrist, *Immunology and Cell Biology* (1998) 76, 222-236). Kovarik and Siegrist (1998, supra) inter alia discuss different antigen delivery systems such as administration of particulate substances, emulsions, liposomes, virosomes, microspheres, live vaccines, vectors and DNA vaccines as well as the use of immunomodulators such as MPL, QS21, MDP derivatives, cytokines, interferons, and CpG oligodesoxynucleotides and combinations of antigen presentation systems and immunomodulators. However, as likewise shown in Kovarik and Siegrist (1998, supra) many of these combinations are hypothetical and may not even provide an efficient Th1 response or even lead to unwanted side effects.

Similarly, Adrian Bot and Constantin Bona (see Adrian Bot and Constantin Bona, Microbes and Infection 4 (2002) 511-520) suggest the use of bacterial CpG motifs to activate immature antigen-presenting cells and to enhance neonatal immunogenicity of DNA vaccines. Additionally, Bot and Bona (2002, supra) suggest a combination with subsequent boosting using conventional vaccines. Nevertheless, the strategy outlined in this paper does not lead to convincing Th1 responses. Furthermore, the approach is based on the use of DNA vaccine, which may be regarded as potentially dangerous as outlined above.

A further promising but very specific strategy relies on the use of the specific novel adjuvant IC31. As known in the art, there are only few adjuvants approved for human use. One major adjuvant approved for human use is e.g. Alum, an aluminium salt based adjuvant. However, although approved for human use, such aluminium salts failed to provide satisfactory augmentation of immune responses for seasonal influenza vaccines in early human clinical trials, an effect, which may be expected likewise during other vaccination strategies. Further licensed adjuvanted influenza vaccines include to date FLUAD® (Novartis Vaccines), containing MF59 in combination with a subunit vaccine formulation, and the virosomal vaccines INFLEXAL®V (Berna Biotech, a Crucell company) and INVIVAC® (Solvay). Although animal studies and human clinical trials revealed a higher immunogenicity profile—defined as increased antibody responses—with the MF59-adjuvanted influenza vaccine, MF59 is not a potent adjuvant for the induction of type 1 driven cellular immune responses. Unlike FLUAD®, the virosomal vaccines represent reconstituted influenza virus envelopes containing the functional influenza surface proteins haemagglutinin and neuraminidase in their phospholipid bilayer. The immunogenicity and local tolerability of virosome-based influenza vaccines has been shown in several studies. However, the development of virosomal formulations is very complex and the costs of goods are high.

In this context, Kamath et al. (see Kamath et al., 2008, PLoS ONE 3(11): e3683. doi:10.1371/journal.pone.0003683) report the use of a specific adjuvant IC31 with Ag85bESAT-6 fusion protein for immunization of neonatal mice and adult mice. Conversely to Alum, IC31H induced strong Th1 and Th17 responses in both age groups, characterized by multifunctional T cells expressing IL-2 and TNFα with or without IFNγ. In the draining lymph nodes, a similarly small number of DC contained the adjuvant and/or the antigen following neonatal or adult immunization. Expression of CD40, CD80, CD86 and IL-12p40 production was focused on the minute adjuvant-bearing DC population, wherein DC targeting/activation was similar in adults and neonates. These DC/T cell responses resulted in an equivalent reduction of bacterial growth following infection with *M. bovis* BCG, whereas no protection was observed when Alum was used as adjuvant. However, no further adjuvants are shown in Kamath et al. (2008, supra), which allow extension of this specific example to other vaccines.

Summarizing the above, none of the present prior art vaccines allow to efficiently evoke immune responses in newborns and/or infants, which show at least similar characteristics as an immune response in adults. Particularly, many vaccines fail to provide an efficient Th1 immune response in newborns and/or infants. Accordingly, there is an urgent need for vaccines optimized for such patients. More precisely, vaccines are required, which do not bear the problems shown in the prior art or at least diminish these problems to a significant extent. Furthermore, it is highly envisaged to provide vaccines, which allow inducing Th1 immune responses in newborns and/or infants, preferably without leading to a shift from Th1 to Th2 immune responses subsequent to administration. Likewise, the administration of DNA based vaccines should be avoided due to possible insertion of DNA into the genome, possible interruption of genes and formation of anti-DNA antibodies.

The object underlying the present invention is solved by the subject matter of the attached claims, more preferably as outlined in the following.

According to a first embodiment, the object underlying the present invention is solved by a vaccine comprising at least one mRNA encoding at least one antigen for use in the prophylaxis and/or treatment of a disease in newborns and/or infants, preferably exhibiting an age of not more than 2 years, preferably of not more than 1 year, more preferably of not more than 9 months or even 6 months, wherein the treatment comprises vaccination of the newborn or young infant and eliciting an immune response in said newborn or infant.

Without being bound to theory RNA vaccines elegantly integrate adjuvanticity and antigen expression, thereby mimicking relevant aspects of viral infections. This increases their efficacy compared to other inactivated (dead) vaccines that require the use of advanced adjuvants in a newborn or an infant, simplifying handling and production. RNA can address a range of dedicated immunologic pattern recognition receptors, including toll-like receptors 3, 7, and 8, RIG-I, MDA5, PKR, and others that may act synergistically and serve to enhance the induction of antigen-specific adaptive B and T cell responses. Importantly, by antigen synthesis in transfected host cells, mRNA vaccines directly introduce antigen into cellular antigen processing and presentation pathways, granting access to MHC molecules and triggering T cell responses, irrespective of the hosts MHC haplotype. This enables the induction of polyclonal T cell responses that may act synergistically with other immune responses, including B cells. Also, presenting the full spectrum of MHC-binding epitopes may circumvent limitations by immature immune systems in a newborn or an infant. Also, endogenous production of antigen ensures faithful posttranslational modification (e.g. proteolytic processing, glycosylation, etc.) that may positively impact immunogenicity. Also, RNA vaccines exhibit safety features that make them superior for use in newborns and/or infants. For example, the increased reactogenicity of live attenuated vaccines generally prevents use in this highly relevant target group. However, considering the short persistence and traceless decay of the vaccine vector within a matter of days the observed good immunogenicity is unexpected and contrasts claims for plasmid DNA vaccines that variously linked efficacy to the persistent expression of antigen.

The at least one mRNA of the inventive vaccine as defined in the first embodiment of the present invention, encoding at least one antigen, may be selected from any antigen, known to a skilled person, preferably suitable to elicit an antigen-specific immune response in a patient. According to the present invention, the term “antigen” refers to a substance which is recognized by the immune system and is capable of triggering an antigen-specific immune response, e.g. by formation of antibodies or antigen-specific T cells as part of an adaptive immune response. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that can serve as antigen-presenting cells are dendritic cells, macrophages, and B cells. Each of these cells has a distinct function in eliciting immune responses.

Tissue dendritic cells take up antigens by phagocytosis and macropinocytosis and are stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. Presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both TH2 and Th1 cells to produce different classes of antibody, thus driving the humoral immune response. T cells recognize an antigen by their T cell receptors which do not recognize and bind antigen directly, but instead recognize short peptide fragments e.g. of pathogens' protein antigens, which are bound to MHC molecules on the surfaces of other cells.

In the context of the present invention, antigens as encoded by the at least one mRNA of the inventive vaccine typically comprise any antigen, falling under the above definition, more preferably protein and peptide antigens. In accordance with the invention, antigens as encoded by the at least one mRNA of the inventive vaccine may be antigens generated outside the cell, more typically antigens not derived from the host organism (e.g. a human) itself (i.e. non-self antigens) but rather derived from host cells outside the host organism, e.g. pathogenic antigens, particularly viral antigens, bacterial antigens, fungal antigens, protozoological antigens, animal antigens (preferably selected from animals or organisms as disclosed herein), allergy antigens, etc. Antigens as encoded by the at least one mRNA of the inventive vaccine may be furthermore antigens generated inside the cell, the tissue or the body, e.g. by secretion of proteins, their degradation, metabolism, etc. Such antigens include antigens derived from the host organism (e.g. a human) itself, e.g. tumour antigens, self-antigens or auto-antigens, such as auto-immune self-antigens, etc., but also (non-self) antigens as defined above, which have been originally been derived from host cells outside the host organism, but which are fragmented or degraded inside the body, tissue or cell, e.g. by (protease) degradation, metabolism, etc.

Pathogenic antigens particularly comprise e.g. antigens from influenza, preferably influenza A, influenza B, influenza C or thogotovirus, preferably influenza antigens haemagglutinin (HA) and/or neuraminidase (NA), preferably influenza antigens derived from haemagglutinin subtypes H1, H2, H3, H4, H5, H6, H7, H8, H9, H10, H11, H12, H13, H14 or H15, and/or neuraminidase subtypes N1, N2, N3, N4, N5, N6, N7, N8 or N9, or preferably selected from influenza A subtypes H1N1, H1N2, H2N2, H2N3, H3N1, H3N2, H3N3, H5N1, H5N2, H7N7 or H9N2, or any further combination, or from matrix protein 1 (M1), ion channel protein M2 (M2), nucleoprotein (NP), etc; or e.g. antigens from respiratory syncytial virus (RSV), including F-protein, G-protein, etc.

One further class of antigens as encoded by the at least one mRNA of the inventive vaccine comprises allergy antigens. Allergy antigens are typically antigens, which cause an allergy in a human and may be derived from either a human or other sources. Such allergy antigens may be selected from antigens derived from different sources, e.g. from animals, plants, fungi, bacteria, etc. Allergens in this context also include antigens derived from e.g. grasses, pollens, molds, drugs, or numerous environmental triggers, etc. Allergy antigens typically belong to different classes of compounds, such as proteins or peptides and their fragments, carbohydrates, polysaccharides, sugars, lipids, phospholipids, etc. Of particular interest in the context of the present invention are antigens, which are encoded by the at least one mRNA of the inventive vaccine, i.e. protein or peptide antigens and their fragments or epitopes, or nucleic acids and their fragments, particularly nucleic acids and their fragments, encoding such protein or peptide antigens and their fragments or epitopes.

Particularly preferred, antigens derived from animals, which are encoded by the at least one mRNA of the inventive vaccine, may include antigens derived from, without being limited thereto, insects, such as mite (e.g. house dust mites), mosquito, bee (e.g. honey bee, bumble bee), cockroach, tick, moth (e.g. silk moth), midge, bug, flea, wasp, caterpillar, fruit fly, migratory locust, grasshopper, ant aphide, from crustaceans, such as shrimps, crab, krill, lobster, prawn, crawfish, scampi, from birds, such as duck, goose, seagull, turkey, ostrich, chicken, from fishes, such as eel, herring, carp, seabream, codfish, halibut, catfish, beluga, salmon, flounder, mackerel, cuttlefish, perch, form molluscs, such as scallop, octopus, abalone, snail, whelk, squid, clam, mussel, from spiders, from mammals, such as cow, rabbit, sheep, lion, jaguar, leopard, rat, pig, buffalo, dog, loris, hamster, guinea pig, fallow deer, horse, cat, mouse, ocelot, serval, from arthropod, such as spider, or silverfish, from worms, such as nematodes, from trichinella species, or roundworm, from amphibians, such as frogs, or from sea squirt, etc. Antigens derived from animals may also comprise antigens contained in animal products, preferably contained in animal products derived from animals as defined above, e.g. milk, eggs, meat, etc., but also from excrements or precipitates of any kind, derived from any of these animals.

Most preferably, antigens derived from animals, which are encoded by the at least one mRNA of the inventive vaccine, may include antigens derived from such animals, causing a disease as defined herein, preferably an infectious disease or an autoimmune disease as defined herein, or any further disease as defined herein.

Antigens derived from plants, which are encoded by the at least one mRNA of the inventive vaccine, may include antigens derived from, without being limited thereto, fruits, such as kiwi, pineapple, jackfruit, papaya, lemon, orange, mandarin, melon, sharon fruit, strawberry, lychee, apple, cherry paradise apple, mango, passion fruit, plum, apricot, nectarine, pear, passion fruit, raspberry, grape, from vegetables, such as garlic, onion, leek, soya bean, celery, cauliflower, turnip, paprika, chickpea, fennel, zucchini, cucumber, carrot, yam, bean, pea, olive, tomato, potato, lentil, lettuce, avocado, parsley, horseradish, chirimoya, beet, pumpkin, spinach, from spices, such as mustard, coriander, saffron, pepper, aniseed, from crop, such as oat, buckwheat, barley, rice, wheat, maize, rapeseed, sesame, from nuts, such as cashew, walnut, butternut, pistachio, almond, hazelnut, peanut, brazil nut, pecan, chestnut, from trees, such as alder, hornbeam, cedar, birch, hazel, beech, ash, privet, oak, plane tree, cypress, palm, from flowers, such as ragweed, carnation, forsythia, sunflower, lupine, chamomile, lilac, passion flower, from grasses, such as quack grass, common bent, brome grass, Bermuda grass, sweet vernal grass, rye grass, or from other plants, such as opium poppy, pellitory, ribwort, tobacco, asparagus, mugwort, cress, etc. Antigens derived from fungi, which are encoded by the at least one mRNA of the inventive vaccine, may include antigens derived from, without being limited thereto, e.g. *Alternia* sp., *Aspergillus* sp., *Beauveria* sp., *Candida* sp., *Cladosporium* sp., *Endothia* sp., *Curcularia* sp., *Embellisia* sp., *Epicoccum* sp., *Fusarium* sp., *Malassezia* sp., *Penicillum* sp., *Pleospora* sp., *Saccharomyces* sp., etc.

Antigens derived from bacteria, which are encoded by the at least one mRNA of the inventive vaccine, may include antigens derived from, without being limited thereto, e.g. *Bacillus tetani, Staphylococcus aureus, Streptomyces griseus*, etc.

One further class of antigens as encoded by the at least one mRNA of the inventive vaccine comprises tumour antigens. "Tumour antigens" are preferably located on the surface of the (tumour) cell. Tumour antigens may also be selected from proteins, which are overexpressed in tumour cells compared to a normal cell. Furthermore, tumour antigens also include antigens expressed in cells which are (were) not themselves (or originally not themselves) degenerated but are associated with the supposed tumour. Antigens which are connected with tumour-supplying vessels or (re)formation thereof, in particular those antigens which are associated with neovascularization, e.g. growth factors, such as VEGF, bFGF etc., are also included herein. Antigens connected with a tumour furthermore include antigens from cells or tissues, typically embedding the tumour. Further, some substances (usually proteins or peptides) are expressed in patients suffering (knowingly or not-knowingly) from a cancer disease and they occur in increased concentrations in the body fluids of said patients. These substances are also referred to as "tumour antigens", however they are not antigens in the stringent meaning of an immune response inducing substance. The class of tumour antigens can be divided further into tumour-specific antigens (TSAs) and tumour-associated-antigens (TAAs). TSAs can only be presented by tumour cells and never by normal "healthy" cells. They typically result from a tumour specific mutation. TAAs, which are more common, are usually presented by both tumour and healthy cells. These antigens are recognized and the antigen-presenting cell can be destroyed by cytotoxic T cells. Additionally, tumour antigens can also occur on the surface of the tumour in the form of, e.g., a mutated receptor. In this case, they can be recognized by antibodies. According to the invention, the terms "cancer diseases" and "tumour diseases" are used synonymously herein.

Examples of tumour antigens as encoded by the at least one mRNA of the inventive vaccine may comprise e.g. antigens selected from the group comprising, without being limited thereto, 5T4, 707-AP (707 alanine proline), 9D7, AFP (alpha-fetoprotein), AlbZIP HPG1, alpha5beta1-Integrin, alpha5beta6-Integrin, alpha-methylacyl-coenzyme A racemase, ART-4 (adenocarcinoma antigen recognized by T cells 4), B7H4, BAGE-1 (B antigen), BCL-2, BING-4, CA 15-3/CA 27-29, CA 19-9, CA 72-4, CA125, calreticulin, CAMEL (CTL-recognized antigen on melanoma), CASP-8 (caspase-8), cathepsin B, cathepsin L, CD19, CD20, CD22, CD25, CD30, CD33, CD40, CD52, CD55, CD56, CD80, CEA (carcinoembryonic antigen), CLCA2 (calcium-activated chloride channel-2), CML28, Coactosin-like protein, Collagen XXIII, COX-2, CT9/BRD6 (bromodomain testis-specific protein), Cten (C-terminal tensin-like protein), cyclin B1, cyclin D1, cyp-B (cyclophilin B), CYPB1 (cytochrom P450 1B1), DAM-10/MAGE-B1 (differentiation antigen melanoma 10), DAM-6/MAGE-B2 (differentiation antigen melanoma 6), EGFR/Her1, EMMPRIN (tumour cell-associated extracellular matrix metalloproteinase inducer/), EpCam (epithelial cell adhesion molecule), EphA2 (ephrin type-A receptor 2), EphA3 (ephrin type-A receptor 3), ErbB3, EZH2 (enhancer of Zeste homolog 2), FGF-5 (fibroblast growth factor-5), FN (fibronectin), Fra-1 (Fos-related antigen-1), G250/CAIX (glycoprotein 250), GAGE-1 (G antigen 1), GAGE-2 (G antigen 2), GAGE-3 (G antigen 3), GAGE-4 (G antigen 4), GAGE-5 (G antigen 5), GAGE-6 (G antigen 6), GAGE-7b (G antigen 7b), GAGE-8 (G antigen 8), GDEP (gene differentially expressed in prostate), GnT-V (N-acetylglucosaminyltransferase V), gp100 (glycoprotein 100 kDa), GPC3 (glypican 3), HAGE (helicase antigen), HAST-2 (human signet ring tumour-2), hepsin, Her2/neu/ErbB2 (human epidermal receptor-2/neurological), HERV-K-MEL, HNE (human neutrophil elastase), homeobox NKX 3.1, HOM-TES-14/SCP-1, HOM-TES-85, HPV-E6, HPV-E7, HST-2, hTERT (human telomerase reverse transcriptase), iCE (intestinal carboxyl esterase), IGF-1R, IL-13Ra2 (interleukin 13 receptor alpha 2 chain), IL-2R, IL-5, immature laminin receptor, kallikrein 2, kallikrein 4, Ki67, KIAA0205, KK-LC-1 (Kita-kyushu lung cancer antigen 1), KM-HN-1, LAGE-1 (L antigen), livin, MAGE-A1 (melanoma antigen-A1), MAGE-A10 (melanoma antigen-A10), MAGE-A12 (melanoma antigen-A12), MAGE-A2 (melanoma antigen-A2), MAGE-A3 (melanoma antigen-A3), MAGE-A4 (melanoma antigen-A4), MAGE-A6 (melanoma antigen-A6), MAGE-A9 (melanoma-antigen-A9), MAGE-B1 (melanoma-antigen-B1), MAGE-B10 (melanoma-antigen-B10), MAGE-B16 (melanoma-antigen-B16), MAGE-B17 (melanoma-antigen-B17), MAGE-B2 (melanoma-antigen-B2), MAGE-B3 (melanoma-antigen-B3), MAGE-B4 (melanoma-antigen-B4), MAGE-B5 (melanoma-antigen-B5), MAGE-B6 (melanoma-antigen-B6), MAGE-C1 (melanoma-antigen-C1), MAGE-C2 (melanoma-antigen-C2), MAGE-C3 (melanoma-antigen-C3), MAGE-D1 (melanoma-antigen-D1), MAGE-D2 (melanoma-antigen-D2), MAGE-D4 (melanoma-antigen-D4), MAGE-E1 (melanoma-antigen-E1), MAGE-E2 (melanoma-antigen-E2), MAGE-F1 (melanoma-antigen-F1), MAGE-H1 (melanoma-antigen-H1), MAGEL2 (MAGE-like 2), mammaglobin A, MART-1/Melan-A (melanoma antigen recognized by T cells-1/melanoma antigen A), MART-2 (melanoma antigen recognized by T cells-2), matrix protein 22, MC1R (melanocortin 1 receptor), M-CSF (macrophage colony-stimulating factor gene), mesothelin, MG50/PXDN, MMP 11 (M-phase phosphoprotein 11), MN/CA IX-antigen, MRP-3 (multidrug resistance-associated protein 3), MUC1 (mucin 1), MUC2 (mucin 2), NA88-A (NA cDNA clone of patient M88), N-acetylglucosaminyltransferase-V, Neo-PAP (Neo-poly(A) polymerase), NGEP, NMP22, NPM/ALK (nucleophosmin/anaplastic lymphoma kinase fusion protein), NSE (neuron-specific enolase), NY-ESO-1 (New York esophageous 1), NY-ESO-B, OA1 (ocular albinism type 1 protein), OFA-iLRP (oncofetal antigen-immature laminin receptor), OGT (O-linked N-acetylglucosamine transferase gene), OS-9, osteocalcin, osteopontin, p15 (protein 15), p15, p190 minor bcr-abl, p53, PAGE-4 (prostate GAGE-like protein-4), PAI-1 (plasminogen activator inhibitor 1), PAI-2 (plasminogen activator inhibitor 2), PAP (prostate acic phosphatase), PART-1, PATE, PDEF, Pim-1-Kinase, Pin1 (Propyl isomerase), POTE, PRAME (preferentially expressed antigen of melanoma), prostein, proteinase-3, PSA (prostate-specific antigen), PSCA, PSGR, PSM, PSMA (prostate-specific membrane antigen), RAGE-1 (renal antigen), RHAMM/CD168 (receptor for hyaluronic acid mediated motility), RU1 (renal ubiquitous 1), RU2 (renal ubiquitous 1), S-100, SAGE (sarcoma antigen), SART-1 (squamous antigen rejecting tumour 1), SART-2 (squamous antigen rejecting tumour 1), SART-3 (squamous antigen rejecting tumour 1), SCC (squamous cell carcinoma antigen), Sp17 (sperm protein 17), SSX-1 (synovial sarcoma X breakpoint 1), SSX-2/HOM-MEL-40 (synovial sarcoma X breakpoint), SSX-4 (synovial sarcoma X breakpoint 4), STAMP-1, STEAP (six transmembrane epithelial antigen prostate), surviving, survivin-2B (intron 2-retaining survivin), TA-90, TAG-72, TARP, TGFb (TGFbeta), TGFbRII (TGFbeta receptor II), TGM-4 (prostate-specific transglutaminase), TRAG-3 (taxol resistant associated protein 3), TRG (testin-related gene), TRP-1 (tyrosine related protein 1), TRP-2/6b (TRP-2/novel exon 6b), TRP-2/INT2 (TRP-2/intron 2), Trp-p8, Tyrosinase, UPA (urokinase-type plasminogen activator), VEGF (vascular endothelial growth factor), VEGFR-2/FLK-1 (vascular endothelial growth factor receptor-2), WT1 (Wilm' tumour gene), or may comprise e.g. mutant antigens expressed in cancer diseases selected from the group comprising, without being limited thereto, alpha-actinin-4/m, ARTC1/m, bcr/abl (breakpoint cluster region-Abelson fusion protein), beta-Catenin/m (beta-Catenin), BRCA1/m, BRCA2/m, CASP-5/m, CASP-8/m, CDC27/m (cell-division-cycle 27), CDK4/m (cyclin-dependent kinase 4), CDKN2A/m, CML66, COA-1/m, DEK-CAN (fusion protein), EFTUD2/m, ELF2/m (Elongation factor 2), ETV6-AML1 (Ets variant gene6/acute myeloid leukemia 1 gene fusion protein), FN1/m (fibronectin 1), GPNMB/m, HLA-A*0201-R170I (arginine to isoleucine exchange at residue 170 of the alpha-helix of the alpha2-domain in the HLA-A2 gene), HLAAll/m, HLA-A2/m, HSP70-2M (heat shock protein 70-2 mutated), KIAA0205/m, K-Ras/m, LDLR-FUT (LDR-Fucosyltransferase fusion protein), MART2/m, ME1/m, MUM-1/m (melanoma ubiquitous mutated 1), MUM-2/m (melanoma ubiquitous mutated 2), MUM-3/m (melanoma ubiquitous mutated 3), Myosin class I/m, neo-PAP/m, NFYC/m, N-Ras/m, OGT/m, OS9/m, p53/m, Pml/RARa (promyelocytic leukemia/retinoic acid receptor alpha), PRDX5/m, PTPRK/m (receptor-type protein-tyrosine phosphatase kappa), RBAF600/m, SIRT2/m, SYT-SSX-1 (synaptotagmin I/synovial sarcoma X fusion protein), SYT-SSX-2 (synaptotagmin I/synovial sarcoma X fusion protein), TEL-AML1 (translocation Ets-family leukemia/acute myeloid leukemia 1 fusion protein), TGFbRII (TGFbeta receptor II), TPI/m (triosephosphate isomerase). According to a specific aspect, however, mRNAs encoding antigens gp100, MAGE-A1, MAGE-A3, MART-1/melan-A, survivin, and/or tyrosinase, more preferably mRNAs encoding antigens gp100, MAGE-A1, MAGE-A3, MART-1/melan-A, survivin, and/or tyrosinase, wherein the mRNAs have been complexed with or stabilized with protamine (e.g. in a ratio of about 80 μg mRNA and 128 μg protamine), may be excluded from the scope of invention. In a preferred aspect the tumour antigens as encoded by the at least one mRNA of the inventive vaccine are selected from the group consisting of 5T4, 707-AP, 9D7, AFP, AlbZIP HPG1, alpha-5-beta-1-integrin, alpha-5-beta-6-integrin, alpha-actinin-4/m, alpha-methyl-acyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD40, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMM-PRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLAAll/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGEA9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGF, VEGFR2/FLK-1, and WT1.

According to a particularly preferred aspect, tumour antigens as encoded by the at least one mRNA of the inventive vaccine are selected from the group consisting of MAGE-A1 (e.g. MAGE-A1 according to accession number M77481), MAGE-A2, MAGE-A3, MAGE-A6 (e.g. MAGE-A6 according to accession number NM_005363), MAGE-C1, MAGE-C2, melan-A (e.g. melan-A according to accession number NM_005511), GP100 (e.g. GP100 according to accession number M77348), tyrosinase (e.g. tyrosinase according to accession number NM_000372), survivin (e.g. survivin according to accession number AF077350), CEA (e.g. CEA according to accession number NM_004363), Her-2/neu (e.g. Her-2/neu according to accession number M11730), WT1 (e.g. WT1 according to accession number NM_000378), PRAME (e.g. PRAME according to accession number NM_006115), EGFRI (epidermal growth factor receptor 1) (e.g. EGFRI (epidermal growth factor receptor 1) according to accession number AF288738), MUC1, mucin-1 (e.g. mucin-1 according to accession number NM_002456), SEC61G (e.g. SEC61G according to accession number NM_014302), hTERT (e.g. hTERT accession number NM_198253), 5T4 (e.g. 5T4 according to accession number NM_006670), NY-Eso-1 (e.g. NY-Eso1 according to accession number NM_001327), TRP-2 (e.g. TRP-2 according to accession number NM_001922), STEAP, PCA, PSA, PSMA, etc.

Particularly preferred, antigens are selected from Influenza A virus (HA, NA, NP, M2, M1 antigens), influenza B virus (HA, NA antigens), respiratory syncytial virus (F, G, M, SH antigens), parainfluenza virus (glycoprotein antigens), *Streptococcus pneumoniae* (pPht, PcsB, StkP antigens), *Corynebacterium diphtheriae, Clostridium tetani*, Measles, Mumps, Rubella, Rabies virus (G, N antigens), *Staphylococcus aureus* (toxin antigen), *Clostridium difficile* (toxin antigen), *Mycobacterium tuberculosis* (acute and dormant antigens), *Candida albicans, Haemophilus* influenzae B (HiB), poliovirus, hepatitis B virus (surface and core antigens), human papillomavirus (L1, L2, E6, E7), human immunodeficiency virus (gp120, gag, env antigens), SARS CoV (spike protein), *Staphylococcus aureus* (IsdA, IsdB, toxin antigens), Pertussis toxin, polio virus (VP1-4), *Plasmodium* (NANP, CSP protein, ssp2, ama1, msp142 antigens), *Staphylococcus aureus* (IsdA, IsdB, toxin), *Bordetella pertussis* (toxin), polio virus VP1-4, *Plasmodium* (NANP, CSP protein, ssp2, ama1, msp142 antigens)

Antigens as encoded by the at least one mRNA of the inventive vaccine may furthermore comprise fragments of such antigens as mentioned herein, particularly of protein or peptide antigens. Fragments of such antigens in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form.

Fragments of antigens as defined herein may also comprise epitopes of those antigens. Epitopes (also called "antigen determinants") are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

According to a further particularly preferred aspect, the tumour antigens as encoded by at least one mRNA of the inventive vaccine may form a cocktail of antigens, e.g. in an active (immunostimulatory) composition or a kit of parts (wherein preferably each antigen is contained in one part of the kit), preferably for eliciting an (adaptive) immune response for the treatment of a disease or disorder as defined herein. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein.

Such a cocktail of antigens, as encoded by the least one mRNA of the inventive vaccine may be used e.g. in the treatment of e.g. prostate cancer (PCa), preferably in the treatment of neoadjuvant and/or hormone-refractory prostate cancers, and diseases or disorders related thereto. For this purpose, the inventive vaccine may comprise at least one mRNA, wherein each mRNA may encode at least one, preferably two, three, four or even more (preferably different) antigens as mentioned herein. Alternatively, the inventive vaccine may contain at least one, two, three, four or even more (preferably different) mRNAs, wherein each mRNA encodes at least one antigen as mentioned herein. Preferably, the antigens are selected from PSA (Prostate-Specific Antigen)=KLK3 (Kallikrein-3), PSMA (Prostate-Specific Membrane Antigen), PSCA (Prostate Stem Cell Antigen), and/or STEAP (Six Transmembrane Epithelial Antigen of the Prostate).

Furthermore, such a cocktail of antigens, as encoded by the at least one mRNA of the inventive vaccine may be used in the treatment of e.g. non-small cell lung cancers (NSCLC), preferably selected from the three main sub-types squamous cell lung carcinoma, adenocarcinoma and large cell lung carcinoma, or of disorders related thereto. For this purpose, the inventive vaccine may comprise at least one mRNA, wherein each mRNA may encode at least one, preferably two, three, four, five, six, seven, eight, nine, ten eleven or twelve (preferably different) antigens as mentioned herein. Alternatively, the inventive vaccine may contain at least one, preferably two, three, four, five, six, seven, eight, nine, ten, eleven or twelve (preferably different) mRNAs, wherein each mRNA encodes at least one antigen as mentioned herein. Preferably, such antigens are selected from hTERT, WT1, MAGE-A2, 5T4, MAGE-A3, MUC1, Her-2/neu, NY-ESO-1, CEA, Survivin, MAGE-C1, and/or MAGE-C2.

In the above aspects, each of the above defined antigens may be encoded by one (monocistronic) mRNA. In other words, in this case the at least one mRNA of the inventive vaccine may comprise at least two (three, four, etc.) (monocistronic) mRNAs, wherein each of these at least two (three, four, etc.) (monocistronic) mRNAs may encode, e.g. just one (preferably different) antigen, preferably selected from one of the above mentioned antigen combinations.

According to a particularly preferred aspect, the at least one mRNA of the inventive vaccine may comprise (at least) one bi- or even multicistronic mRNA, preferably mRNA, i.e. (at least) one mRNA which carries, e.g. two or even more of the coding sequences of at least two (preferably different) antigens, preferably selected from one of the above mentioned antigen combinations. Such coding sequences, e.g. of the at least two (preferably different) antigens, of the (at least) one bi- or even multicistronic mRNA may be separated by at least one IRES (internal ribosomal entry site) sequence, as defined below. Thus, the term "encoding at least two (preferably different) antigens" may mean, without being limited thereto, that the (at least) one (bi- or even multicistronic) mRNA, may encode e.g. at least two, three, four, five, six, seven, eight, nine, ten, eleven or twelve or more (preferably different) antigens of the above mentioned group(s) of antigens, or their fragments or variants, etc. In this context, a so-called IRES (internal ribosomal entry site) sequence as defined herein can function as a sole ribosome binding site, but it can also serve to provide a bi- or even multicistronic RNA as defined herein which codes for several proteins, which are to be translated by the ribosomes independently of one another. Examples of IRES sequences which can be used according to the invention are those from picornaviruses (e.g. FMDV), pestiviruses (CFFV), polioviruses (PV), encephalomyocarditis viruses (ECMV), foot and mouth disease viruses (FMDV), hepatitis C viruses (HCV), classical swine fever viruses (CSFV), mouse leukemia virus (MLV), simian immunodeficiency viruses (SIV) or cricket paralysis viruses (CrPV).

According to a further particularly preferred aspect, the at least one mRNA of the inventive vaccine may comprise a mixture of at least one monocistronic mRNA as defined herein, and at least one bi- or even multicistronic RNA, preferably mRNA, as defined herein. The at least one monocistronic RNA and/or the at least one bi- or even multicistronic RNA preferably encode different antigens, or their fragments or variants, the antigens preferably being selected from one of the above mentioned antigens, more preferably in one of the above mentioned combinations. However, the at least one monocistronic RNA and the at least one bi- or even multicistronic RNA may preferably also encode (in part) identical antigens selected from one of the above mentioned antigens, preferably in one of the above mentioned combinations, provided that the at least one mRNA of the inventive vaccine as a whole provides at least two (preferably different) antigens, as defined herein. Such an aspect may be advantageous e.g. for a staggered, e.g. time dependent, administration of one or several of the at least one mRNA of the inventive vaccine to a patient in need thereof. The components of such a vaccine may be contained in (different parts of) a kit of parts composition or may be e.g. administered separately as components of the same inventive vaccine as defined according to the present invention.

In a further preferred embodiment the at least one mRNA of the inventive vaccine (or any further nucleic acid as defined herein) may also occur in the form of a modified nucleic acid.

According to a first aspect, the at least one mRNA of the inventive vaccine (or any further nucleic acid as defined herein) may be provided as a "stabilized nucleic acid" that is essentially resistant to in vivo degradation (e.g. by an exo- or endo-nuclease).

In this context, the at least one mRNA of the inventive vaccine (or any further nucleic acid as defined herein) may contain backbone modifications, sugar modifications or base modifications. A backbone modification in connection with the present invention is a modification in which phosphates of the backbone of the nucleotides contained in the at least one mRNA of the inventive vaccine (or any further nucleic acid as defined herein) are chemically modified. A sugar modification in connection with the present invention is a chemical modification of the sugar of the nucleotides of the at least one mRNA of the inventive vaccine (or any further nucleic acid as defined herein). Furthermore, a base modification in connection with the present invention is a chemical modification of the base moiety of the nucleotides of the at least one mRNA of the inventive vaccine (or any further nucleic acid as defined herein).

According to a further aspect, the at least one mRNA of the inventive vaccine (or any further nucleic acid as defined herein) can contain a lipid modification. Such a lipid-modified nucleic acid typically comprises a nucleic acid as defined herein, e.g. an mRNA or any further nucleic acid. Such a lipid-modified mRNA of the inventive vaccine (or any further lipid-modified nucleic acid as defined herein) typically further comprises at least one linker covalently linked with that nucleic acid molecule, and at least one lipid covalently linked with the respective linker. Alternatively, the lipid-modified mRNA of the inventive vaccine (or any further lipid-modified nucleic acid as defined herein) comprises at least one nucleic acid molecule as defined herein, e.g. an mRNA or any further nucleic acid, and at least one (bifunctional) lipid covalently linked (without a linker) with that nucleic acid molecule. According to a third alternative, the lipid-modified mRNA of the inventive vaccine (or any further lipid-modified nucleic acid as defined herein) comprises a nucleic acid molecule as defined herein, e.g. an mRNA or any further nucleic acid, at least one linker covalently linked with that nucleic acid molecule, and at least one lipid covalently linked with the respective linker, and also at least one (bifunctional) lipid covalently linked (without a linker) with that nucleic acid molecule.

The at least one mRNA of the inventive vaccine (or any further nucleic acid as defined herein) may likewise be stabilized in order to prevent degradation of the mRNA (or any further nucleic acid molecule) by various approaches. It is known in the art that instability and (fast) degradation of RNA in general may represent a serious problem in the application of RNA based compositions. This instability of RNA is typically due to RNA-degrading enzymes, "RNAases" (ribonucleases), wherein contamination with such ribonucleases may sometimes completely degrade RNA in solution. Accordingly, the natural degradation of RNA in the cytoplasm of cells is very finely regulated and RNase contaminations may be generally removed by special treatment prior to use of said compositions, in particular with diethyl pyrocarbonate (DEPC). A number of mechanisms of natural degradation are known in this connection in the prior art, which may be utilized as well. E.g., the terminal structure is typically of critical importance particularly for an mRNA. As an example, at the 5' end of naturally occurring mRNAs there is usually a so-called "cap structure" (a modified guanosine nucleotide), and at the 3' end is typically a sequence of up to 200 adenosine nucleotides (the so-called poly-A tail).

According to another aspect, the at least one mRNA of the inventive vaccine may be modified and thus stabilized by modifying the G/C content of the mRNA, preferably of the coding region thereof.

In a particularly preferred aspect of the present invention, the G/C content of the coding region of the at least one mRNA of the inventive vaccine is modified, particularly increased, compared to the G/C content of the coding region of its particular wild type coding sequence, i.e. the unmodified mRNA. The encoded amino acid sequence of the mRNA is preferably not modified compared to the coded amino acid sequence of the particular wild type mRNA.

The modification of the G/C-content of the at least one mRNA of the inventive vaccine is based on the fact that the sequence of any mRNA region to be translated is important for efficient translation of that mRNA. Thus, the composition and the sequence of various nucleotides are important. In particular, sequences having an increased G (guanosine)/C (cytosine) content are more stable than sequences having an increased A (adenosine)/U (uracil) content. According to the invention, the codons of the coding sequence or mRNA are therefore varied compared to its wild type coding sequence or mRNA, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Preferably, the G/C content of the coding region of the at least one mRNA of the inventive vaccine is increased by at least 7%, more preferably by at least 15%, particularly preferably by at least 20%, compared to the G/C content of the coded region of the wild type mRNA. According to a specific aspect at least 5%, 10%, 20%, 30%, 40%, 50%, 60%, more preferably at least 70%, even more preferably at least 80% and most preferably at least 90%, 95% or even 100% of the substitutable codons in the region coding for a protein or peptide as defined herein or its fragment or variant thereof or the whole sequence of the wild type mRNA sequence or coding sequence are substituted, thereby increasing the G/C content of said sequence.

In this context, it is particularly preferable to increase the G/C content of the at least one mRNA of the inventive vaccine to the maximum (i.e. 100% of the substitutable codons), in particular in the region coding for a protein, compared to the wild type sequence.

According to the invention, a further preferred modification of the at least one mRNA of the inventive vaccine, especially if the nucleic acid is in the form of an mRNA or codes for an mRNA, is based on the finding that the translation efficiency is also determined by a different frequency in the occurrence of tRNAs in cells. Thus, if so-called "rare codons" are present in the at least one mRNA of the inventive vaccine to an increased extent, the corresponding modified mRNA is translated to a significantly poorer degree than in the case where codons coding for relatively "frequent" tRNAs are present.

Preferably, the coding region of the at least one mRNA of the inventive vaccine is modified compared to the corresponding region of the wild type mRNA or coding sequence such that at least one codon of the wild type sequence which codes for a tRNA which is relatively rare in the cell is exchanged for a codon which codes for a tRNA which is relatively frequent in the cell and carries the same amino acid as the relatively rare tRNA. By this modification, the sequences of the at least one mRNA of the inventive vaccine, especially if the nucleic acid is in the form of an mRNA or codes for an mRNA, is modified such that codons for which frequently occurring tRNAs are available are inserted. In other words, according to the invention, by this modification all codons of the wild type sequence which code for a tRNA which is relatively rare in the cell can in each case be exchanged for a codon which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content which is increased, in particular maximized, in the modified at least one mRNA of the inventive vaccine with the "frequent" codons without modifying the amino acid sequence of the protein encoded by the coding region of the mRNA. This preferred aspect allows provision of a particularly efficiently translated and stabilized (modified) at least one mRNA of the inventive vaccine.

According to a further preferred aspect of the invention, the at least one mRNA of the inventive vaccine as defined herein or ay further nucleic acid molecule as defined herein preferably has at least one 5' and/or 3' stabilizing sequence. These stabilizing sequences in the 5' and/or 3' untranslated regions have the effect of increasing the half-life of the nucleic acid in the cytosol. These stabilizing sequences can have 100% sequence identity to naturally occurring sequences which occur in viruses, bacteria and eukaryotes, but can also be partly or completely synthetic. The untranslated sequences (UTR) of the (alpha-)globin gene, e.g. from *Homo sapiens* or *Xenopus laevis* may be mentioned as an example of stabilizing sequences which can be used in the present invention for a stabilized nucleic acid. Another example of a stabilizing sequence has the general formula (C/U)CCAN$_x$CCC(U/A)Py$_x$UC(C/U)CC (SEQ ID NO: 383), which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Such stabilizing sequences can of course be used individually or in combination with one another and also in combination with other stabilizing sequences known to a person skilled in the art.

Nevertheless, substitutions, additions or eliminations of bases are preferably carried out with the at least one mRNA of the inventive vaccine or any further nucleic acid molecule as defined herein, especially if the nucleic acid is in the form of an mRNA, using a DNA matrix for preparation of the nucleic acid molecule by techniques of the well known site directed mutagenesis or with an oligonucleotide ligation strategy (see e.g. Maniatis et al., Molecular Cloning: A Laboratory Manual, Cold Spring Harbor Laboratory Press, 3rd ed., Cold Spring Harbor, NY, 2001). In such a process, for preparation of the at least one mRNA of the inventive vaccine as defined herein a corresponding DNA molecule may be transcribed in vitro. This DNA matrix preferably comprises a suitable promoter, e.g. a T7 or SP6 promoter, for in vitro transcription, which is followed by the desired nucleotide sequence for the at least one mRNA to be prepared and a termination signal for in vitro transcription. The DNA molecule, which forms the matrix of the at least one mRNA of interest, may be prepared by fermentative proliferation and subsequent isolation as part of a plasmid which can be replicated in bacteria. Plasmids which may be mentioned as suitable for the present invention are e.g. the plasmids pT7 Ts (GenBank accession number U26404; Lai et al., Development 1995, 121: 2349 to 2360), PGEM® series, e.g. PGEM®1 (GenBank accession number X65300; from Promega) and pSP64 (GenBank accession number X65327); cf. also Mezei and Storts, Purification of PCR Products, in: Griffin and Griffin (ed.), PCR Technology: Current Innovation, CRC Press, Boca Raton, FL, 2001.

Nucleic acid molecules used according to the invention and as defined herein, e.g. the at least one mRNA of the inventive vaccine or any further nucleic acid molecule as defined herein, may be modified as outlined above for the at least one mRNA of the inventive vaccine.

Additionally, nucleic acid molecules used according to the invention and as defined herein, e.g. the at least one mRNA of the inventive vaccine or any further nucleic acid molecule as defined herein, may be prepared using any method known in the art, including synthetic methods such as e.g. solid phase synthesis, as well as in vitro methods, such as in vitro transcription reactions. According to one preferred aspect of the present invention the at least one mRNA of the inventive vaccine may be administered naked without being associated with any further vehicle, transfection or complexation agent for increasing the transfection efficiency of the at least one mRNA.

In a further preferred aspect of the present invention the at least one mRNA of the inventive vaccine is associated with a vehicle, transfection or complexation agent for increasing the transfection efficiency of the at least one mRNA. Particularly preferred agents in this context suitable for increasing the transfection efficiency are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, Pestivirus Ems, HSV, VP22 (Herpes simplex), MAP, KALA or protein transduction domains (PTDs), PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila* antennapedia), pAntp, pIsl, FGF, Lactoferrin, Transportan, Buforin-2, Bac715-24, SynB, SynB(1), pVEC, hCT-derived peptides, SAP, or histones. Additionally, preferred cationic or polycationic proteins or peptides may be selected from the following proteins or peptides having the following total formula: $(Arg)_l;(Lys)_m;(His)_n;(Orn)_o;(Xaa)_x$, wherein l+m+n+o+x=8-15, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred cationic peptides in this context are e.g. $Arg_7$, $Arg_8$, $Arg_9$, $H_3R_9$, $R_9H_3$, $H_3R_9H_3$, $YSSR_9SSY$, $(RKH)_4$, $Y(RKH)_2R$, etc. Further preferred cationic or polycationic compounds, which can be used as transfection agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIM-RI: Dimyristo-oxypropyl dimethyl hydroxyethyl ammonium bromide, DOTAP: dioleoyloxy-3-(trimethylammonio)propane, DC-6-14: O,O-ditetradecanoyl-N-((atrimethylammonioacetyl)diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyloxymethyloxy)ethyl] trimethylammonium, CLIP9: rac-[2(2,3-dihexadecyloxypropyloxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

The at least one mRNA of the inventive vaccine encoding at least one antigen may also be complexed with a polymeric carrier formed by disulfide-crosslinked cationic components. The term "cationic component" typically refers to a charged molecule, which is positively charged (cation) at a pH value of about 1 to 9, preferably of a pH value of or below 9, of or below 8, of or below 7, most preferably at physiological pH values, e.g. about 7.3 to 7.4. Accordingly, a cationic peptide, protein or polymer according to the present invention is positively charged under physiological conditions, particularly under physiological salt conditions of the cell in vivo. The definition "cationic" may also refer to "polycationic" components.

In this context the cationic components, which form basis for the polymeric carrier of the inventive vaccine by disulfide-crosslinkage, are typically selected from any suitable cationic or polycationic peptide, protein or polymer suitable for this purpose, particular any cationic or polycationic peptide, protein or polymer capable to complex a nucleic acid as defined according to the present invention, and thereby preferably condensing the nucleic acid. The cationic or polycationic peptide, protein or polymer, is preferably a linear molecule, however, branched cationic or polycationic peptides, proteins or polymers may also be used.

Each cationic or polycationic protein, peptide or polymer of the polymeric carrier, which may be used to complex the at least one mRNA of the inventive vaccine contains at least one —SH moiety, most preferably at least one cysteine residue or any further chemical group exhibiting an —SH moiety, capable to form a disulfide linkage upon condensation with at least one further cationic or polycationic protein, peptide or polymer as cationic component of the polymeric carrier as mentioned herein.

Each cationic or polycationic protein, peptide or polymer or any further component of the polymeric carrier, which may be used to complex the at least one mRNA of the inventive vaccine is preferably linked to its neighbouring component(s) (cationic proteins, peptides, polymers or other components) via disulfide-crosslinking. Preferably, the disulfide-crosslinking is a (reversible) disulfide bond (—S—S—) between at least one cationic or polycationic protein, peptide or polymer and at least one further cationic or polycationic protein, peptide or polymer or other component of the polymeric carrier. The disulfide-crosslinking is typically formed by condensation of —SH-moieties of the components of the polymeric carrier particularly of the cationic components.

Such an —SH-moiety may be part of the structure of the cationic or polycationic protein, peptide or polymer or any further component of the polymeric carrier prior to disulfide-crosslinking or may be added prior to disulfide-crosslinking by a modification as defined below. In this context, the sulphurs adjacent to one component of the polymeric carrier, necessary for providing a disulfide bond, may be provided by the component itself, e.g. by a —SH moiety as defined herein or may be provided by modifying the component accordingly to exhibit a —SH moiety. These —SH-moieties are typically provided by each of the components, e.g. via a cysteine or any further (modified) amino acid of the component, which carries a —SH moiety. In the case that the cationic component or any further component of the polymeric carrier is a peptide or protein it is preferred that the —SH moiety is provided by at least one cysteine residue. Alternatively, the component of the polymeric carrier may be modified accordingly with a —SH moiety, preferably via a chemical reaction with a compound carrying a —SH moiety, such that each of the components of the polymeric carrier carries at least one such —SH moiety. Such a compound carrying a —SH moiety may be e.g. an (additional) cysteine or any further (modified) amino acid or compound of the component of the polymeric carrier, which carries a —SH moiety. Such a compound may also be any non-amino compound or moiety, which contains or allows to introduce a —SH moiety into the component as defined herein. Such non-amino compounds may be attached to the component of the polymeric carrier according to the present invention via chemical reactions or binding of compounds, e.g. by binding of a 3-thio propionic acid or 2-iminothiolane (Traut's reagent), by amide formation (e.g. carboxylic acids, sulphonic acids, amines, etc.), by Michael addition (e.g maleinimide moieties, α,β unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. In some cases the —SH moiety may be masked by protecting groups during chemical attachment to the component. Such protecting groups are known in the art and may be removed after chemical coupling. In each case, the —SH moiety, e.g. of a cysteine or of any further (modified) amino acid or compound, may be present at the terminal ends or internally at any position of the component of the polymeric carrier. As defined herein, each of the components of the polymeric carrier typically exhibits at least one —SH-moiety, but may also contain two, three, four, five, or even more —SH-moieties. Additionally to binding of cationic components a —SH moiety may be used to attach further components of the polymeric carrier of the inventive vaccine as defined herein, particularly an amino acid component, e.g. antigen epitopes, antigens, antibodies, cell penetrating peptides (e.g. TAT), ligands, etc.

As defined above, the polymeric carrier, which may be used to complex the at least one mRNA of the inventive vaccine may be formed by disulfide-crosslinked cationic (or polycationic) components.

According to one first alternative, at least one cationic (or polycationic) component of the polymeric carrier, which may be used to complex the at least one mRNA of the inventive vaccine may be selected from cationic or polycationic peptides or proteins. Such cationic or polycationic peptides or proteins preferably exhibit a length of about 3 to 100 amino acids, preferably a length of about 3 to 50 amino acids, more preferably a length of about 3 to 25 amino acids, e.g. a length of about 3 to 10, 5 to 15, 10 to 20 or 15 to 25 amino acids. Alternatively or additionally, such cationic or polycationic peptides or proteins may exhibit a molecular weight of about 0.01 kDa to about 100 kDa, including a molecular weight of about 0.5 kDa to about 100 kDa, preferably of about 10 kDa to about 50 kDa, even more preferably of about 10 kDa to about 30 kDa.

In the specific case that the cationic component of the polymeric carrier, which may be used to complex the at least one mRNA of the inventive vaccine comprises a cationic or polycationic peptide or protein, the cationic properties of the cationic or polycationic peptide or protein or of the entire polymeric carrier, if the polymeric carrier is entirely composed of cationic or polycationic peptides or proteins, may be determined upon its content of cationic amino acids. Preferably, the content of cationic amino acids in the cationic or polycationic peptide or protein and/or the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 15% to 75%, even more preferably in the range of about 20% to 50%, e.g. 20, 30, 40 or 50%, or in a range formed by any two of the afore mentioned values, provided, that the content of all amino acids, e.g. cationic, lipophilic, hydrophilic, aromatic and further amino acids, in the cationic or polycationic peptide or protein, or in the entire polymeric carrier, if the polymeric carrier is entirely composed of cationic or polycationic peptides or proteins, is 100%.

Preferably, such cationic or polycationic peptides or proteins of the polymeric carrier, which comprise or are additionally modified to comprise at least one —SH moiety, are selected from, without being restricted thereto, cationic peptides or proteins such as protamine, nucleoline, spermine or spermidine, oligo- or poly-L-lysine (PLL), basic polypeptides, oligo or polyarginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila* antennapedia), pAntp, pIsl, etc., antimicrobial-derived CPPs e.g. Buforin-2, Bac715-24, SynB, SynB(1), pVEC, hCT-derived peptides, SAP, MAP, PpTG20, Loligomere, FGF, Lactoferrin, histones, VP22 derived or analog peptides, Pestivirus Ems, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

Alternatively or additionally, such cationic or polycationic peptides or proteins of the polymeric carrier, which comprise or are additionally modified to comprise at least one —SH moiety, are selected from, without being restricted thereto, following cationic peptides having the following sum formula (I):

$$\{(Arg)_l; (Lys)_m; (His)_n; (Orn)_o; (Xaa)_x\};$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Om (Omithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Om and Xaa may be positioned at any place of the peptide. In this context cationic peptides or proteins in the range of 7-30 amino acids are particular preferred. Even more preferred peptides of this formula are oligoarginines such as e.g. $Arg_7$, $Arg_8$, $Arg_9$, $Arg_{12}$, $His_3Arg_9$, $Arg_9His_3$, $His_3Arg_9His_3$, $His_6Arg_9His_6$, $His_3Arg_4His_3$, $His_6Arg_4His_6$, $TyrSer_2Arg_9Ser_2Tyr$, $(ArgLysHis)_4$, $Tyr(ArgLysHis)_2Arg$, etc.

According to a particular preferred embodiment, such cationic or polycationic peptides or proteins of the polymeric carrier having the empirical sum formula (I) as shown above, may, without being restricted thereto, comprise at least one of the following subgroup of formulae:

$Arg_7$, $Arg_8$, $Arg_9$, $Arg_{10}$, $Arg_{11}$, $Arg_{12}$, $Arg_{13}$, $Arg_{14}$, $Arg_{15-30}$;

$Lys_7$, $Lys_8$, $Lys_9$, $Lys_{10}$, $Lys_{11}$, $Lys_{12}$, $Lys_{13}$, $Lys_{14}$, $Lys_{15-30}$;

$His_7$, $His_8$, $His_9$, $His_{10}$, $His_{11}$, $His_{12}$, $His_{13}$, $His_{14}$, $His_{15-30}$;

$Orn_7$, $Orn_8$, $Orn_9$, $Orn_{10}$, $Orn_{11}$, $Orn_{12}$, $Orn_{13}$, $Orn_{14}$, $Orn_{15-30}$;

According to a further particularly preferred embodiment, cationic or polycationic peptides or proteins of the polymeric carrier, having the empirical sum formula (I) as shown above and which comprise or are additionally modified to comprise at least one —SH moiety, may be preferably selected from, without being restricted thereto, at least one of the following subgroup of formulae. The following formulae (as with empirical formula (I)) do not specify any amino acid order, but are intended to reflect empirical formulae by exclusively specifying the (number of) amino acids as components of the respective peptide. Accordingly, as an example, empirical formula $Arg_{(7-29)}Lys_1$ is intended to mean that peptides falling under this formula contain 7 to 19 Arg residues and 1 Lys residue of whatsoever order. If the peptides contain 7 Arg residues and 1 Lys residue, all variants having 7 Arg residues and 1 Lys residue are encompassed. The Lys residue may therefore be positioned anywhere in the e.g. 8 amino acid long sequence composed of 7 Arg and 1 Lys residues. The subgroup preferably comprises:

wherein $(Arg)_l;(Lys)_m;(His)_n;(Orn)_o;$ and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide.

This embodiment may apply to situations, wherein the cationic or polycationic peptide or protein of the polymeric carrier, e.g. when defined according to empirical formula $(Arg)_l;(Lys)_m;(His)_n;(Orn)_o;(Xaa)_x$ (formula (I)) as shown $Arg_{(4-29)}Lys_1$, $Arg_{(4-29)}His_1$, $Arg_{(4-29)}Orn_1$, $Lys_{(4-29)}His_1$, $Lys_{(4-29)}Orn_1$, $His_{(4-29)}Orn_1$, $Arg_{(3-28)}Lys_2$, $Arg_{(3-28)}His_2$, $Arg_{(3-28)}Orn_2$, $Lys_{(3-28)}His_2$, $Lys_{(3-28)}Orn_2$, $His_{(3-28)}Orn_2$, $Arg_{(2-27)}Lys_3$, $Arg_{(2-27)}His_3$, $Arg_{(2-27)}Orn_3$, $Lys_{(2-27)}His_3$, $Lys_{(2-27)}Orn_3$, $His_{(2-27)}Orn_3$, $Arg_{(1-26)}Lys_4$, $Arg_{(1-26)}His_4$, $Arg_{(1-26)}Orn_4$, $Lys_{(1-26)}His_4$, $Lys_{(1-26)}Orn_4$, $His_{(1-26)}Orn_4$, $Arg_{(3-28)}Lys_1His_1$, $Arg_{(3-28)}Lys_1Orn_1$, $Arg_{(3-28)}His_1Orn_1$, $Arg_1Lys_{(3-28)}His_1$, $Arg_1Lys_{(3-28)}Orn_1$, $Lys_{(3-28)}His_1Orn_1$, $Arg_1Lys_1His_{(3-28)}$, $Arg_1His_{(3-28)}Orn_1$, $Lys_1His_{(3-28)}Orn_1$;

$Arg_{(2-27)}Lys_2His_1$, $Arg_{(2-27)}Lys_1His_2$, $Arg_{(2-27)}Lys_2Orn_1$, $Arg_{(2-27)}Lys_1Orn_2$, $Arg_{(2-27)}His_2Orn_1$, $Arg_{(2-27)}His_1Orn_2$, $Arg_2Lys_{(2-27)}His_1$, $Arg_1Lys_{(2-27)}His_2$, $Arg_2Lys_{(2-27)}Orn_1$, $Arg_1Lys_{(2-27)}Orn_2$, $Lys_{(2-27)}His_2Orn_1$, $Lys_{(2-27)}His_1Orn_2$, $Arg_2Lys_1His_{(2-27)}$, $Arg_1Lys_2His_{(2-27)}$, $Arg_2His_{(2-27)}Orn_1$, $Arg_1His_{(2-27)}Orn_2$, $Lys_2His_{(2-27)}Orn_1$, $Lys_1His_{(2-27)}Orn_2$;

$Arg_{(1-26)}Lys_3His_1$, $Arg_{(1-26)}Lys_2His_2$, $Arg_{(1-26)}Lys_1His_3$, $Arg_{(1-26)}Lys_3Orn_1$, $Arg_{(1-26)}Lys_2Orn_2$, $Arg_{(1-26)}Lys_1Orn_3$, $Arg_{(1-26)}His_3Orn_1$, $Arg_{(1-26)}His_2Orn_2$, $Arg_{(1-26)}His_1Orn_3$, $Arg_3Lys_{(1-26)}His_1$, $Arg_2Lys_{(1-26)}His_2$, $Arg_1Lys_{(1-26)}His_3$, $Arg_3Lys_{(1-26)}Orn_1$, $Arg_2Lys_{(1-26)}Orn_2$, $Arg_1Lys_{(1-26)}Orn_3$, $Lys_{(1-26)}His_3Orn_1$, $Lys_{(1-26)}His_2Orn_2$, $Lys_{(1-26)}His_1Orn_3$, $Arg_3Lys_1His_{(1-26)}$, $Arg_2Lys_2His_{(1-26)}$, $Arg_1Lys_3His_{(1-26)}$, $Arg_3His_{(1-26)}Orn_1$, $Arg_2His_{(1-26)}Orn_2$, $Arg_1His_{(1-26)}Orn_3$, $Lys_3His_{(1-26)}Orn_1$, $Lys_2His_{(1-26)}Orn_2$, $Lys_1His_{(1-26)}Orn_3$;

$Arg_{(2-27)}Lys_1His_1Orn_1$, $Arg_1Lys_{(2-27)}His_1Orn_1$, $Arg_1Lys_1His_{(2-27)}Orn_1$, $Arg_1Lys_1His_1Orn_{(2-27)}$;

$Arg_{(1-26)}Lys_2His_1Orn_1$, $Arg_{(1-26)}Lys_1His_2Orn_1$, $Arg_{(1-26)}Lys_1His_1Orn_2$, $Arg_2Lys_{(1-26)}His_1Orn_1$, $Arg_1Lys_{(1-26)}His_2Orn_1$, $Arg_1Lys_{(1-26)}His_1Orn_2$, $Arg_2Lys_1His_{(1-26)}Orn_1$, $Arg_1Lys_2His_{(1-26)}Orn_1$, $Arg_1Lys_1His_{(1-26)}Orn_2$, $Arg_2Lys_1His_1Orn_{(1-26)}$, $Arg_1Lys_2His_1Orn_{(1-26)}$, $Arg_1Lys_1His_2Orn_{(1-26)}$;

According to a further particular preferred embodiment, cationic or polycationic peptides or proteins of the polymeric carrier, having the empirical sum formula (I) as shown above and which comprise or are additionally modified to comprise at least one —SH moiety, may be, without being restricted thereto, selected from the subgroup consisting of generic formulas $Arg_7$ (also termed as $R_7$), $Arg_9$ (also termed $R_9$), $Arg_{12}$ (also termed as $R_{12}$).

According to a one further particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above and which comprise or are additionally modified to comprise at least one —SH moiety, may be, without being restricted thereto, selected from subformula (Ia):

$$\{(Arg)_l;(Lys)_m;(His)_n;(Orn)_o;(Xaa')_x(Cys)_y\} \quad \text{formula (Ia)}$$

above, comprises or has been modified with at least one cysteine as —SH moiety in the above meaning such that the cationic or polycationic peptide as cationic component carries at least one cysteine, which is capable to form a disulfide bond with other components of the polymeric carrier.

According to another particular preferred embodiment, the cationic or polycationic peptide or protein of the polymeric carrier, when defined according to formula $\{(Arg)_l;(Lys)_m;(His)_n;(Orn)_o;(Xaa)_x\}$ (formula (I)) as shown above, may be, without being restricted thereto, selected from subformula (Ib):

$$Cys^1 \{(Arg)_l;(Lys)_m;(His)_n;(Orn)_o;(Xaa)_x\} Cys^2 \quad \text{(formula (Ib))}$$

wherein empirical formula $\{(Arg)_l;(Lys)_m;(His)_n;(Orn)_o;(Xaa)_x\}$ (formula (I)) is as defined herein and forms a core of an amino acid sequence according to (semiempirical) formula (I) and wherein $Cys^1$ and $Cys^2$ are Cysteines proximal to, or terminal to $(Arg)_l;(Lys)_m;(His)_n;(Orn)_o;(Xaa)_x$.

Exemplary examples may comprise any of the above sequences flanked by two Cys and following sequences:

$CysArg_7Cys$ (SEQ ID NO. 1)
Cys-Arg-Arg-Arg-Arg-Arg-Arg-Arg-Cys $CysArg_8Cys$ (SEQ ID NO. 2)
Cys-Arg-Arg-Arg-Arg-Arg-Arg-Arg-Arg-Cys $CysArg_9Cys$: (SEQ ID NO. 3)
Cys-Arg-Arg-Arg-Arg-Arg-Arg-Arg-Arg-Arg-Cys $CysArg_{10}Cys$ (SEQ ID NO. 4)
Cys-Arg-Arg-Arg-Arg-Arg-Arg-Arg-Arg-Arg-Arg-Cys $CysArg_{11}Cys$ (SEQ ID NO. 5)
Cys-Arg-Arg-Arg-Arg-Arg-Arg-Arg-Arg-Arg-Arg-Arg-Cys $CysArg_{12}Cys$: (SEQ ID NO. 6)
Cys-Arg-Arg-Arg-Arg-Arg-Arg-Arg-Arg-Arg-Arg-Arg-Arg-Cys $CysArg_{13}Cys$: (SEQ ID NO. 7)
Cys-Arg-Arg-Arg-Arg-Arg-Arg-Arg-Arg-Arg-Arg-Arg-Arg-Arg-Cys $CysArg_{14}Cys$: (SEQ ID NO. 8)
Cys-Arg-Arg-Arg-Arg-Arg-Arg-Arg-Arg-Arg-Arg-Arg-Arg-Arg-Arg-Cys $CysArg_{15}Cys$: (SEQ ID NO. 9)
Cys-Arg-Arg-Arg-Arg-Arg-Arg-Arg-Arg-Arg-Arg-Arg-Arg-Arg-Arg-Arg-Cys $CysArg_{16}Cys$: (SEQ ID NO. 10)
Cys-Arg-Arg-Arg-Arg-Arg-Arg-Arg-Arg-Arg-Arg-Arg-Arg-Arg-Arg-Arg-Arg-Cys $CysArg_{17}Cys$: (SEQ ID NO. 11)
Cys-Arg-Arg-Arg-Arg-Arg-Arg-Arg-Arg-Arg-Arg-Arg-Arg-Arg-Arg-Arg-Arg-Arg-Cys $CysArg_{18}Cys$: (SEQ ID NO. 12)
Cys-Arg-Arg-Arg-Arg-Arg-Arg-Arg-Arg-Arg-Arg-Arg-Arg-Arg-Arg-Arg-Arg-Arg-Arg-Cys $CysArg_{19}Cys$: (SEQ ID NO. 13)
Cys-Arg-Arg-Arg-Arg-Arg-Arg-Arg-Arg-Arg-Arg-Arg-Arg-Arg-Arg-Arg-Arg-Arg-Arg-Cys $CysArg_{20}Cys$: (SEQ ID NO. 14)
Cys-Arg-Arg-Arg-Arg-Arg-Arg-Arg-Arg-Arg-Arg-Arg-Arg-Arg-Arg-Arg-Arg-Arg-Arg-Arg Cys

This embodiment may apply to situations, wherein the cationic or polycationic peptide or protein of the polymeric carrier, which may be used to complex the at least one mRNA of the inventive vaccine, e.g. when defined according to empirical formula $(Arg)_l;(Lys)_m;(His)_n;(Orn)_o;(Xaa)_x$ (formula (I)) as shown above, has been modified with at least two cysteines as —SH moieties in the above meaning such that the cationic or polycationic peptide of the inventive polymeric carrier carries at least two (terminal) cysteines, which are capable to form a disulfide bond with other components of the polymeric carrier.

According to a second alternative, at least one cationic (or polycationic) component of the polymeric carrier may be selected from e.g. any (non-peptidic) cationic or polycationic polymer suitable in this context, provided that this (non-peptidic) cationic or polycationic polymer exhibits or is modified to exhibit at least one —SH-moiety, which provide for a disulfide bond linking the cationic or polycationic polymer with another component of the polymeric carrier as defined herein. Thus, likewise as defined herein, the polymeric carrier may comprise the same or different cationic or polycationic polymers.

In the specific case that the cationic component of the polymeric carrier comprises a (non-peptidic) cationic or polycationic polymer the cationic properties of the (non-peptidic) cationic or polycationic polymer may be determined upon its content of cationic charges when compared to the overall charges of the components of the cationic polymer. Preferably, the content of cationic charges in the cationic polymer at a (physiological) pH as defined herein is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 10% to 90%, more preferably in the range of about 30% to 100%, even preferably in the range of about 50% to 100%, e.g. 50, 60, 70, 80%, 90% or 100%, or in a range formed by any two of the afore mentioned values, provided, that the content of all charges, e.g. positive and negative charges at a (physiological) pH as defined herein, in the entire cationic polymer is 100%.

Preferably, the (non-peptidic) cationic component of the polymeric carrier represents a cationic or polycationic polymer, typically exhibiting a molecular weight of about 0.1 or 0.5 kDa to about 100 kDa, preferably of about 1 kDa to about 75 kDa, more preferably of about 5 kDa to about 50 kDa, even more preferably of about 5 kDa to about 30 kDa, or a molecular weight of about 10 kDa to about 50 kDa, even more preferably of about 10 kDa to about 30 kDa. Additionally, the (non-peptidic) cationic or polycationic polymer typically exhibits at least one —SH-moiety, which is capable to form a disulfide linkage upon condensation with either other cationic components or other components of the polymeric carrier as defined herein.

In the above context, the (non-peptidic) cationic component of the polymeric carrier, which may be used to complex the at least one mRNA of the inventive vaccine may be selected from acrylates, modified acrylates, such as pDMAEMA (poly(dimethylaminoethyl methylacrylate)), chitosanes, aziridines or 2-ethyl-2-oxazoline (forming oligo ethylenimines or modified oligoethylenimines), polymers obtained by reaction of bisacrylates with amines forming oligo beta aminoesters or poly amido amines, or other polymers like polyesters, polycarbonates, etc. Each molecule of these (non-peptidic) cationic or polycationic polymers typically exhibits at least one —SH-moiety, wherein these at least one —SH-moiety may be introduced into the (non-peptidic) cationic or polycationic polymer by chemical modifications, e.g. using imonothiolan, 3-thio propionic acid or introduction of —SH-moieties containing amino acids, such as cysteine or any further (modified) amino acid. Such —SH-moieties are preferably as already defined above.

In the context of the polymeric carrier, the cationic components, which form basis for the polymeric carrier, which may be used to complex the at least one mRNA of the inventive vaccine by disulfide-crosslinkage, may be the same or different from each other. It is also particularly preferred that the polymeric carrier of the present invention comprises mixtures of cationic peptides, proteins or polymers and optionally further components as defined herein, which are crosslinked by disulfide bonds as described herein.

In this context, the inventive polymeric carrier, which may be used to complex the at least one mRNA of the inventive vaccine allows to combine desired properties of different (short) cationic or polycationic peptides, proteins or polymers or other components. The polymeric carrier, e.g., allows to efficiently compact nucleic acids for the purpose of efficient transfection of nucleic acids, for adjuvant therapy, for the purposes of gene therapy, for gene knock-down or others strategies without loss of activity, particularly exhibiting an efficient transfection of a nucleic acid into different cell lines in vitro but particularly transfection in vivo. The polymeric carrier is furthermore not toxic to cells, provides for efficient release of its nucleic acid cargo, is stable during lyophilization and is applicable as immunostimulating agent or adjuvant. In this context the components of the inventive polymeric carrier can be varied in such a way that the cytokine pattern induced can be determined.

In particular, the polymeric carrier formed by disulfide-linked cationic components allows considerably to vary its peptide or polymeric content and thus to modulate its biophysical/biochemical properties, particularly the cationic properties of the polymeric carrier, quite easily and fast, e.g. by incorporating as cationic components the same or different cationic peptide(s) or polymer(s) and optionally adding other components into the polymeric carrier. Even though consisting of quite small non-toxic monomer units the polymeric carrier forms a long cationic binding sequence providing a strong condensation of the mRNA as its nucleic acid cargo and complex stability. Under the reducing conditions of the cytosole (e.g. cytosolic GSH), the complex is rapidly degraded into its (cationic) components, which are further degraded (e.g. oligopeptides). This supports deliberation of the nucleic acid cargo in the cytosol. Due to degradation into small oligopeptides or polymers in the cytosol, no toxicity is observed as known for high-molecular oligopeptides or polymers, e.g. from high-molecular polyarginine.

Accordingly, the polymeric carrier, which may be used to complex the at least one mRNA of the inventive vaccine may comprise different (short) cationic or polycationic peptides, proteins or polymers selected from cationic or polycationic peptides, proteins or (non-peptidic) polymers as defined above, optionally together with further components as defined herein.

Additionally, the polymeric carrier, which may be used to complex the at least one mRNA of the inventive vaccine as defined above, more preferably at least one of the different (short) cationic or polycationic peptides or (non-peptidic) polymers forming basis for the polymeric carrier via disulfide-crosslinking, may be, preferably prior to the disulfide-crosslinking, modified with at least one further component. Alternatively, the polymeric carrier as such may be modified with at least one further component. It may also optionally comprise at least one further component, which typically forms the polymeric carrier disulfide together with the other the (short) cationic or polycationic peptides as defined above via disulfide crosslinking.

To allow modification of a cationic or polycationic peptide or a (non-peptidic) polymer as defined above, each of the components of the polymeric carrier may (preferably already prior to disulfide-crosslinking) also contain at least one further functional moiety, which allows attaching such further components as defined herein. Such functional moieties may be selected from functionalities which allow the attachment of further components, e.g. functionalities as defined herein, e.g. by amide formation (e.g. carboxylic acids, sulphonic acids, amines, etc.), by Michael addition (e.g maleinimide moieties, α,β unsatured carbonyls, etc.), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components.

According to a particularly preferred embodiment, the further component, which may be contained in the polymeric carrier, and which may be used to complex the at least one mRNA of the inventive vaccine or which may be used to modify the different (short) cationic or polycationic peptides or (non-peptidic) polymers forming basis for the polymeric carrier or the biophysical/biochemical properties of the polymeric carrier as defined herein, is an amino acid component (AA). According to the present invention, the amino acid component (AA) comprises a number of amino acids preferably in a range of about 1 to 100, preferably in a range of about 1 to 50, more preferably selected from a number comprising 1, 2, 3, 4, 5, 6, 7, 8, 9, 10, 11, 12, 13, 14 or 15-20, or may be selected from a range formed by any two of the afore mentioned values. In this context the amino acids of amino acid component (AA) can be chosen independently from each other. For example if in the polymeric carrier two or more (AA) components are present they can be the same or can be different from each other.

The amino acid component (AA) may contain or may be flanked (e.g. terminally) by a —SH containing moiety, which allows introducing this component (AA) via a disulfide bond into the polymeric carrier as defined herein. In the specific case that the —SH containing moiety represents a cysteine, the amino acid component (AA) may also be read as -Cys-(AA)-Cys- wherein Cys represents Cysteine and provides for the necessary —SH-moiety for a disulfide bond. The —SH containing moiety may be also introduced into amino acid component (AA) using any of modifications or reactions as shown above for the cationic component or any of its components.

Furthermore, the amino acid component (AA) may be provided with two —SH-moieties (or even more), e.g. in a form represented by formula HS-(AA)-SH to allow binding to two functionalities via disulfide bonds, e.g. if the amino acid component (AA) is used as a linker between two further components (e.g. as a linker between two cationic polymers). In this case, one —SH moiety is preferably protected in a first step using a protecting group as known in the art, leading to an amino acid component (AA) of formula HS-(AA)-S-protecting group. Then, the amino acid component (AA) may be bound to a further component of the polymeric carrier, to form a first disulfide bond via the non-protected —SH moiety. The protected-SH-moiety is then typically deprotected and bound to a further free —SH-moiety of a further component of the polymeric carrier to form a second disulfide bond.

Alternatively, the amino acid component (AA) may be provided with other functionalities as already described above for the other components of the polymeric carrier, which allow binding of the amino acid component (AA) to any of components of the polymeric carrier.

Thus, according to the present invention, the amino acid component (AA) may be bound to further components of the polymeric carrier, which may be used to complex the at least one mRNA of the inventive vaccine with or without using a disulfide linkage. Binding without using a disulfide linkage may be accomplished by any of the reactions described above, preferably by binding the amino acid component (AA) to the other component of the polymeric carrier using an amid-chemistry as defined herein. If desired or necessary, the other terminus of the amino acid component (AA), e.g. the N- or C-terminus, may be used to couple another component, e.g. a ligand L. For this purpose, the other terminus of the amino acid component (AA) preferably comprises or is modified to comprise a further functionality, e.g. an alkyn-species (see above), which may be used to add the other component via e.g. click-chemistry. If the ligand is bound via an acid-labile bond, the bond is preferably cleaved off in the endosome and the polymeric carrier presents amino acid component (AA) at its surface.

The amino acid component (AA) may occur as a further component of the polymeric carrier, which may be used to complex the at least one mRNA of the inventive vaccine as defined above, e.g. as a linker between cationic components e.g. as a linker between one cationic peptide and a further cationic peptide, as a linker between one cationic polymer and a further cationic polymer, as a linker between one cationic peptide and a cationic polymer, all preferably as defined herein, or as an additional component of the polymeric carrier, e.g. by binding the amino acid component (AA) to the polymeric carrier or a component thereof, e.g. via side chains, SH-moieties or via further moieties as defined herein, wherein the amino acid component (AA) is preferably accordingly modified.

According to a further and particularly preferred alternative, the amino acid component (AA), may be used to modify the polymeric carrier, particularly the content of cationic components in the polymeric carrier as defined above.

In this context it is preferable, that the content of cationic components in the polymeric carrier is at least 10%, 20%, or 30%, preferably at least 40%, more preferably at least 50%, 60% or 70%, but also preferably at least 80%, 90%, or even 95%, 96%, 97%, 98%, 99% or 100%, most preferably at least 30%, 40%, 50%, 60%, 70%, 80%, 90%, 95%, 96%, 97%, 98%, 99% or 100%, or may be in the range of about 30% to 100%, more preferably in the range of about 50% to 100%, even preferably in the range of about 70% to 100%, e.g. 70, 80, 90 or 100%, or in a range formed by any two of the afore mentioned values, provided, that the content of all components in the polymeric carrier is 100%.

In the context of the present invention, the amino acid component (AA) may be selected from the following alternatives.

According to a first alternative, the amino acid component (AA) may be an aromatic amino acid component (AA). The incorporation of aromatic amino acids or sequences as amino aromatic acid component (AA) into the polymeric carrier of the present invention enables a different (second) binding of the polymeric carrier to the nucleic acid due to interactions of the aromatic amino acids with the bases of the nucleic acid cargo in contrast to the binding thereof by cationic charged sequences of the polymeric carrier molecule to the phosphate backbone. This interaction may occur e.g. by intercalations or by minor or major groove binding. This kind of interaction is not prone to decompaction by anionic complexing partners (e.g. Heparin, Hyaluronic acids) which are found mainly in the extracellular matrix in vivo and is also less susceptible to salt effects.

For this purpose, the amino acids in the aromatic amino acid component (AA) may be selected from either the same or different aromatic amino acids e.g. selected from Trp, Tyr, or Phe. Alternatively, the amino acids (or the entire aromatic amino acid component (AA)) may be selected from following peptide combinations Trp-Tyr, Tyr-Trp, Trp-Trp, Tyr-Tyr, Trp-Tyr-Trp, Tyr-Trp-Tyr, Trp-Trp-Trp, Tyr-Tyr-Tyr, Trp-Tyr-Trp-Tyr (SEQ ID NO: 23), Tyr-Trp-Tyr-Trp (SEQ ID NO: 24), Trp-Trp-Trp-Trp (SEQ ID NO: 25), Phe-Tyr, Tyr-Phe, Phe-Phe, Phe-Tyr-Phe, Tyr-Phe-Tyr, Phe-Phe-Phe, Phe-Tyr-Phe-Tyr (SEQ ID NO: 32), Tyr-Phe-Tyr-Phe (SEQ ID NO: 33), Phe-Phe-Phe-Phe (SEQ ID NO: 34), Phe-Trp, Trp-Phe, Phe-Phe, Phe-Trp-Phe, Trp-Phe-Trp, Phe-Trp-Phe-Trp (SEQ ID NO: 40), Trp-Phe-Trp-Phe (SEQ ID NO: 41), or Tyr-Tyr-Tyr-Tyr (SEQ ID NO: 42), etc. Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the aromatic amino acid component (AA) may be selected from e.g. peptide combinations Cys-Tyr-Cys, Cys-Trp-Cys, Cys-Trp-Tyr-Cys (SEQ ID NO: 45), Cys-Tyr-Trp-Cys (SEQ ID NO: 46), Cys-Trp-Trp-Cys (SEQ ID NO: 47), Cys-Tyr-Tyr-Cys (SEQ ID NO: 48), Cys-Trp-Tyr-Trp-Cys (SEQ ID NO: 49), Cys-Tyr-Trp-Tyr-Cys (SEQ ID NO: 50), Cys-Trp-Trp-Trp-Cys (SEQ ID NO: 51), Cys-Tyr-Tyr-Tyr-Cys (SEQ ID NO: 52), Cys-Trp-Tyr-Trp-Tyr-Cys (SEQ ID NO: 53), Cys-Tyr-Trp-Tyr-Trp-Cys (SEQ ID NO: 54), Cys-Trp-Trp-Trp-Trp-Cys (SEQ ID NO: 55), Cys-Tyr-Tyr-Tyr-Tyr-Cys (SEQ ID NO: 56), Cys-Phe-Cys, Cys-Phe-Tyr-Cys (SEQ ID NO: 58), Cys-Tyr-Phe-Cys (SEQ ID NO: 59), Cys-Phe-Phe-Cys (SEQ ID NO: 60), Cys-Tyr-Tyr-Cys (SEQ ID NO: 61), Cys-Phe-Tyr-Phe-Cys (SEQ ID NO: 62), Cys-Tyr-Phe-Tyr-Cys (SEQ ID NO: 63), Cys-Phe-Phe-Phe-Cys (SEQ ID NO: 64), Cys-Tyr-Tyr-Tyr-Cys (SEQ ID NO: 65), Cys-Phe-Tyr-Phe-Tyr-Cys (SEQ ID NO: 66), Cys-Tyr-Phe-Tyr-Phe-Cys (SEQ ID NO: 67), Cys-Phe-Phe-Phe-Phe-Cys (SEQ ID NO: 68), Cys-Phe-Trp-Cys (SEQ ID NO: 69), Cys-Trp-Phe-Cys (SEQ ID NO: 70), Cys-Phe-Phe-Cys (SEQ ID NO: 71), Cys-Phe-Trp-Phe-Cys (SEQ ID NO: 72), Cys-Trp-Phe-Trp-Cys (SEQ ID NO: 73), Cys-Phe-Trp-Phe-Trp-Cys (SEQ ID NO: 74), Cys-Trp-Phe-Trp-Phe-Cys (SEQ ID NO: 75), etc. Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 11, 12, 13, 14, 15 or even more times. These peptide combinations may also be combined with each other as suitable.

Each Cys above may also be replaced by any modified peptide or chemical compound carrying a free —SH-moiety as defined herein. (SEQ ID NOs: 43-75). Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the aromatic amino acid component (AA) may contain or represent at least one proline, which may serve as a structure breaker of longer sequences of Trp, Tyr and Phe in the aromatic amino acid component (AA), preferably two, three or more prolines.

According to a second alternative, the amino acid component (AA) may be a hydrophilic (and preferably non charged polar) amino acid component (AA). The incorporation of hydrophilic (and preferably non charged polar) amino acids or sequences as amino hydrophilic (and preferably non charged polar) acid component (AA) into the polymeric carrier of the present invention enables a more flexible binding to the nucleic acid cargo. This leads to a more effective compaction of the nucleic acid cargo and hence to a better protection against nucleases and unwanted decompaction. It also allows provision of a (long) polymeric carrier which exhibits a reduced cationic charge over the entire carrier and in this context to better adjusted binding properties, if desired or necessary.

For this purpose, the amino acids in the hydrophilic (and preferably non charged polar) amino acid component (AA) may be selected from either the same or different hydrophilic (and preferably non charged polar) amino acids e.g. selected from Thr, Ser, Asn or Gln. Alternatively, the amino acids (or the entire hydrophilic (and preferably non charged polar) amino acid component (AA)) may be selected from following peptide combinations Ser-Thr, Thr-Ser, Ser-Ser, Thr-Thr, Ser-Thr-Ser, Thr-Ser-Thr, Ser-Ser-Ser, Thr-Thr-Thr, Ser-Thr-Ser-Thr (SEQ ID NO: 84), Thr-Ser-Thr-Ser (SEQ ID NO: 85), Ser-Ser-Ser-Ser (SEQ ID NO: 86), Thr-Thr-Thr-Thr (SEQ ID NO: 87), Gln-Asn, Asn-Gln, Gln-Gln, Asn-Asn, Gln-Asn-Gln, Asn-Gln-Asn, Gln-Gln-Gln, Asn-Asn-Asn, Gln-Asn-Gln-Asn (SEQ ID NO: 96), Asn-Gln-Asn-Gln (SEQ ID NO: 97), Gln-Gln-Gln-Gln (SEQ ID NO: 98), Asn-Asn-Asn-Asn (SEQ ID NO: 99), Ser-Asn, Asn-Ser, Ser-Ser, Asn-Asn, Ser-Asn-Ser, Asn-Ser-Asn, Ser-Ser-Ser, Asn-Asn-Asn, Ser-Asn-Ser-Asn (SEQ ID NO: 108), Asn-Ser-Asn-Ser (SEQ ID NO: 109), Ser-Ser-Ser-Ser (SEQ ID NO: 110), or Asn-Asn-Asn-Asn (SEQ ID NO: 111), etc. Such peptide combinations may be repeated e.g. 1, 2, 3, 4, 5, 6, 7, 8, 9, 10, 11, 12, 13, 14, 15 or even more times. These peptide combinations may also be combined with each other as suitable.

Additionally, the hydrophilic (and preferably non-charged polar) amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the hydrophilic (and preferably non-charged polar) amino acid component (AA) may be selected from e.g. peptide combinations Cys-Thr-Cys, Cys-Ser-Cys, Cys-Ser-Thr-Cys (SEQ ID NO: 114), Cys-Thr-Ser-Cys (SEQ ID NO: 115), Cys-Ser-Ser-Cys (SEQ ID NO: 116), Cys-Thr-Thr-Cys (SEQ ID NO: 117), Cys-Ser-Thr-Ser-Cys (SEQ ID NO: 118), Cys-Thr-Ser-Thr-Cys (SEQ ID NO: 119), Cys-Ser-Ser-Ser-Cys (SEQ ID NO: 120), Cys-Thr-Thr-Thr-Cys (SEQ ID NO: 121), Cys-Ser-Thr-Ser-Thr-Cys (SEQ ID NO: 122), Cys-Thr-Ser-Thr-Ser-Cys (SEQ ID NO: 123), Cys-Ser-Ser-Ser-Ser-Cys (SEQ ID NO: 124), Cys-Thr-Thr-Thr-Thr-Cys (SEQ ID NO: 125), Cys-Asn-Cys, Cys-Gln-Cys, Cys-Gln-Asn-Cys (SEQ ID NO: 128), Cys-Asn-Gln-Cys (SEQ ID NO: 129), Cys-Gln-Gln-Cys (SEQ ID NO: 130), Cys-Asn-Asn-Cys (SEQ ID NO: 131), Cys-Gln-Asn-Gln-Cys (SEQ ID NO: 132), Cys-Asn-Gln-Asn-Cys (SEQ ID NO: 133), Cys-Gln-Gln-Gln-Cys (SEQ ID NO: 134), Cys-Asn-Asn-Asn-Cys (SEQ ID NO: 135), Cys-Gln-Asn-Gln-Asn-Cys (SEQ ID NO: 136), Cys-Asn-Gln-Asn-Gln-Cys (SEQ ID NO: 137), Cys-Gln-Gln-Gln-Gln-Cys (SEQ ID NO: 138), Cys-Asn-Asn-Asn-Asn-Cys (SEQ ID NO: 139), Cys-Asn-Cys, Cys-Ser-Cys, Cys-Ser-Asn-Cys (SEQ ID NO: 142), Cys-Asn-Ser-Cys (SEQ ID NO: 143), Cys-Ser-Ser-Cys (SEQ ID NO: 144), Cys-Asn-Asn-Cys (SEQ ID NO: 145), Cys-Ser-Asn-Ser-Cys (SEQ ID NO: 146), Cys-Asn-Ser-Asn-Cys (SEQ ID NO: 147), Cys-Ser-Ser-Ser-Cys (SEQ ID NO: 148), Cys-Asn-Asn-Asn-Cys (SEQ ID NO: 149), Cys-Ser-Asn-Ser-Asn-Cys (SEQ ID NO: 150), Cys-Asn-Ser-Asn-Ser-Cys (SEQ ID NO: 151), Cys-Ser-Ser-Ser-Ser-Cys (SEQ ID NO: 152), or Cys-Asn-Asn-Asn-Asn-Cys (SEQ ID NO: 153), etc. Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the hydrophilic (and preferably non-charged polar) amino acid component (AA) may contain at least one proline, which may serve as a structure breaker of longer sequences of Ser, Thr and Asn in the hydrophilic (and preferably non charged polar) amino acid component (AA), preferably two, three or more prolines.

According to a third alternative, the amino acid component (AA) may be a lipophilic amino acid component (AA). The incorporation of lipophilic amino acids or sequences as amino lipophilic acid component (AA) into the polymeric carrier of the present invention enables a stronger compaction of the nucleic acid cargo and/or the polymeric carrier and its nucleic acid cargo when forming a complex. This is particularly due to interactions of one or more polymer strands of the polymeric carrier, particularly of lipophilic sections of lipophilic amino acid component (AA) and the nucleic acid cargo. This interaction will preferably add an additional stability to the complex between the polymeric carrier and its nucleic acid cargo. This stabilization may somehow be compared to a sort of non covalent crosslinking between different polymer strands. Especially in aqueous environment this interaction is typically strong and provides a significant effect.

For this purpose, the amino acids in the lipophilic amino acid component (AA) may be selected from either the same or different lipophilic amino acids e.g. selected from Leu, Val, Ile, Ala, Met. Alternatively, the amino acid AA (or the entire lipophilic amino acid component (AA)) may be selected from following peptide combinations Leu-Val, Val-Leu, Leu-Leu, Val-Val, Leu-Val-Leu, Val-Leu-Val, Leu-Leu-Leu, Val-Val-Val, Leu-Val-Leu-Val (SEQ ID NO: 162), Val-Leu-Val-Leu (SEQ ID NO: 163), Leu-Leu-Leu-Leu (SEQ ID NO: 164), Val-Val-Val-Val (SEQ ID NO: 165), Ile-Ala, Ala-Ile, Ile-Ile, Ala-Ala, Ile-Ala-Ile, Ala-Ile-Ala, Ile-Ile-Ile, Ala-Ala-Ala, Ile-Ala-Ile-Ala (SEQ ID NO: 175), Ala-Ile-Ala-Ile (SEQ ID NO: 176), Ile-Ile-Ile-Ile (SEQ ID NO: 177), Ala-Ala-Ala-Ala (SEQ ID NO: 178), Met-Ala, Ala-Met, Met-Met, Ala-Ala, Met-Ala-Met, Ala-Met-Ala, Met-Met-Met, Ala-Ala-Ala, Met-Ala-Met-Ala (SEQ ID NO: 186), Ala-Met-Ala-Met (SEQ ID NO: 187), or Met-Met-Met-Met (SEQ ID NO: 188) etc. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain or may be flanked by a —SH containing moiety, which allows introducing this component via a disulfide bond as a further part of the polymeric carrier above, e.g. as a linker. Such a —SH containing moiety may be any moiety as defined herein suitable to couple one component as defined herein to a further component as defined herein. As an example, such a —SH containing moiety may be a cysteine. Then, e.g. the lipophilic amino acid component (AA) may be selected from e.g. peptide combinations Cys-Val-Cys, Cys-Leu-Cys, Cys-Leu-Val-Cys (SEQ ID NO: 191), Cys-Val-Leu-Cys (SEQ ID NO: 192), Cys-Leu-Leu-Cys (SEQ ID NO: 193), Cys-Val-Val-Cys (SEQ ID NO: 194), Cys-Leu-Val-Leu-Cys (SEQ ID NO: 195), Cys-Val-Leu-Val-Cys (SEQ ID NO: 196), Cys-Leu-Leu-Leu-Cys (SEQ ID NO: 197), Cys-Val-Val-Val-Cys (SEQ ID NO: 198), Cys-Leu-Val-Leu-Val-Cys (SEQ ID NO: 199), Cys-Val-Leu-Val-Leu-Cys (SEQ ID NO: 200), Cys-Leu-Leu-Leu-Leu-Cys (SEQ ID NO: 201), Cys-Val-Val-Val-Val-Cys (SEQ ID NO: 202), Cys-Ala-Cys, Cys-Ile-Cys, Cys-Ile-Ala-Cys (SEQ ID NO: 205), Cys-Ala-Ile-Cys (SEQ ID NO: 206), Cys-Ile-Ile-Cys (SEQ ID NO: 207), Cys-Ala-Ala-Cys (SEQ ID NO: 208), Cys-Ile-Ala-Ile-Cys (SEQ ID NO: 209), Cys-Ala-Ile-Ala-Cys (SEQ ID NO: 210), Cys-Ile-Ile-Ile-Cys (SEQ ID NO: 211), Cys-Ala-Ala-Ala-Cys (SEQ ID NO: 212), Cys-Ile-Ala-Ile-Ala-Cys (SEQ ID NO: 213), Cys-Ala-Ile-Ala-Ile-Cys (SEQ ID NO: 214), Cys-Ile-Ile-Ile-Ile-Cys (SEQ ID NO: 215), or Cys-Ala-Ala-Ala-Ala-Cys (SEQ ID NO: 216), Cys-Met-Cys, Cys-Met-Ala-Cys (SEQ ID NO: 218), Cys-Ala-Met-Cys (SEQ ID NO: 219), Cys-Met-Met-Cys (SEQ ID NO: 220), Cys-Ala-Ala-Cys (SEQ ID NO: 221), Cys-Met-Ala-Met-Cys (SEQ ID NO: 222), Cys-Ala-Met-Ala-Cys (SEQ ID NO: 223), Cys-Met-Met-Met-Cys (SEQ ID NO: 224), Cys-Ala-Ala-Ala-Cys (SEQ ID NO: 225), Cys-Met-Ala-Met-Ala-Cys (SEQ ID NO: 226), Cys-Ala-Met-Ala-Met-Cys (SEQ ID NO: 227), Cys-Met-Met-Met-Met-Cys (SEQ ID NO: 228), or Cys-Ala-Ala-Ala-Ala-Cys (SEQ ID NO: 229), etc. Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the lipophilic amino acid component (AA) may contain at least one proline, which may serve as a structure breaker of longer sequences of Leu, Val, Ile, Ala and Met in the lipophilic amino acid component (AA), preferably two, three or more prolines.

Finally, according to a fourth alternative, the amino acid component (AA) may be a weak basic amino acid component (AA). The incorporation of weak basic amino acids or sequences as weak basic amino acid component (AA) into the polymeric carrier of the present invention may serve as a proton sponge and facilitates endosomal escape (also called endosomal release) (proton sponge effect). Incorporation of such a weak basic amino acid component (AA) preferably enhances transfection efficiency.

For this purpose, the amino acids in the weak basic amino acid component (AA) may be selected from either the same or different weak amino acids e.g. selected from histidine or aspartate (aspartic acid). Alternatively, the weak basic amino acids (or the entire weak basic amino acid component (AA)) may be selected from following peptide combinations Asp-His, His-Asp, Asp-Asp, His-His, Asp-His-Asp, His-Asp-His, Asp-Asp-Asp, His-His-His, Asp-His-Asp-His (SEQ ID NO: 238), His-Asp-His-Asp (SEQ ID NO: 239), Asp-Asp-Asp-Asp (SEQ ID NO: 240), or His-His-His-His (SEQ ID NO: 241), etc. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain or may be flanked by a —SH containing moiety, which allows introducing this component via a disulfide bond as a further part of the polymeric carrier as defined above, e.g. as a linker. Such a —SH containing moiety may be any moiety as defined herein suitable to couple one component as defined herein to a further component as defined herein. As an example, such a —SH containing moiety may be a cysteine. Then, e.g. the weak basic amino acid component (AA) may be selected from e.g. peptide combinations Cys-His-Cys, Cys-Asp-Cys, Cys-Asp-His-Cys (SEQ ID NO: 244), Cys-His-Asp-Cys (SEQ ID NO: 245), Cys-Asp-Asp-Cys (SEQ ID NO: 246), Cys-His-His-Cys (SEQ ID NO: 247), Cys-Asp-His-Asp-Cys (SEQ ID NO: 248), Cys-His-Asp-His-Cys (SEQ ID NO: 249), Cys-Asp-Asp-Asp-Cys (SEQ ID NO: 250), Cys-His-His-His-Cys (SEQ ID NO: 251), Cys-Asp-His-Asp-His-Cys (SEQ ID NO: 252), Cys-His-Asp-His-Asp-Cys (SEQ ID NO: 253), Cys-Asp-Asp-Asp-Asp-Cys (SEQ ID NO: 254), or Cys-His-His-His-His-Cys (SEQ ID NO: 255), etc. Each Cys above may also be replaced by any modified peptide or chemical compound carrying a free —SH-moiety as defined herein. Such peptide combinations may be repeated e.g. 1, 2, 3, 4, 5, 6, 7, 8, 9, 10, 12, 13, 14, 15 or even more times. These peptide combinations may also be combined with each other as suitable.

Additionally, the weak basic amino acid component (AA) may contain at least one proline, which may serve as a structure breaker of longer sequences of histidine or aspartate (aspartic acid) in the weak basic amino acid component (AA), preferably two, three or more prolines.

According to a fifth alternative, the amino acid component (AA) may be a signal peptide or signal sequence, a localisation signal or sequence, a nuclear localisation signal or sequence (NLS), an antibody, a cell penetrating peptide, (e.g. TAT), etc. Preferably such an amino acid component (AA) is bound to the polymeric carrier or to another component of the polymeric carrier via a (reversible) disulfide bond. In this context the signal peptide or signal sequence, a localisation signal or sequence, a nuclear localisation signal or sequence (NLS), an antibody, a cell penetrating peptide, (e.g. TAT), etc.; additionally comprises at least one —SH-moiety. In this context a signal peptide, a localisation signal or sequence or a nuclear localisation signal or sequence (NLS), may be used to direct the inventive polymeric carrier cargo complex to specific target cells (e.g. hepatocytes or antigen-presenting cells) and preferably allows a translocalisation of the polymeric carrier to a specific target, e.g. into the cell, into the nucleus, into the endosomal compartment, sequences for the mitochondrial matrix, localisation sequences for the plasma membrane, localisation sequences for the Golgi apparatus, the nucleus, the cytoplasm and the cytoskeleton, etc. Such signal peptide, a localisation signal or sequence or a nuclear localisation signal may be used for the transport of any of the herein defined nucleic acids, preferably an RNA or a DNA, more preferably an shRNA or a pDNA, e.g. into the nucleus. Without being limited thereto, such a signal peptide, a localisation signal or sequence or a nuclear localisation signal may comprise, e.g., localisation sequences for the endoplasmic reticulum. Particular localisation signals or sequences or a nuclear localisation signals may include e.g. KDEL (SEQ ID NO: 256), DDEL (SEQ ID NO: 257), DEEL (SEQ ID NO: 258), QEDL (SEQ ID NO: 259), RDEL (SEQ ID NO: 260), and GQNLSTSN (SEQ ID NO: 261), nuclear localisation sequences, including PKKKRKV (SEQ ID NO: 262), PQKKIKS (SEQ ID NO: 263), QPKKP (SEQ ID NO: 264), RKKR (SEQ ID NO: 265), RKKRRQRRRAHQ (SEQ ID NO: 266), RQARRNRRRRWRERQR (SEQ ID NO: 267), MPLTRRRPAASQALAPPTP (SEQ ID NO: 268), GAALTILV (SEQ ID NO: 269), and GAALTLLG (SEQ ID NO: 270), localisation sequences for the endosomal compartment, including MDDQRDLISNNEQLP (SEQ ID NO: 271), localisation sequences for the mitochondrial matrix, including MLFNLRXXLNNAAFRHGHNFMVRN-FRCGQPLX (SEQ ID NO: 272), localisation sequences for the plasma membrane: GCVCSSNP (SEQ ID NO: 273), GQTVTTPL (SEQ ID NO: 274), GQELSQHE (SEQ ID NO: 275), GNSPSYNP (SEQ ID NO: 276), GVSGSKGQ (SEQ ID NO: 277), GQTITTPL (SEQ ID NO: 278), GQTLTTPL (SEQ ID NO: 279), GQIFSRSA (SEQ ID NO: 280), GQIHGLSP (SEQ ID NO: 281), GARASVLS (SEQ ID NO: 282), and GCTLSAEE (SEQ ID NO: 283), localisation sequences for the endoplasmic reticulum and the nucleus, including GAQVSSQK (SEQ ID NO: 284), and GAQLSRNT (SEQ ID NO: 285), localisation sequences for the Golgi apparatus, the nucleus, the cytoplasm and the cytoskeleton, including GNAAAAKK (SEQ ID NO: 286), localisation sequences for the cytoplasm and cytoskeleton, including GNEASYPL (SEQ ID NO: 287), localisation sequences for the plasma membrane and cytoskeleton, including GSSKSKPK (SEQ ID NO: 288), etc. Examples of secretory signal peptide sequences as defined herein include, without being limited thereto, signal sequences of classical or non-classical MHC-molecules (e.g. signal sequences of MHC I and II molecules, e.g. of the MHC class I molecule HLA-A*0201), signal sequences of cytokines or immunoglobulins as defined herein, signal sequences of the invariant chain of immunoglobulins or antibodies as defined herein, signal sequences of Lamp1, Tapasin, Erp57, Calreticulin, Calnexin, and further membrane associated proteins or of proteins associated with the endoplasmic reticulum (ER) or the endosomal-lysosomal compartment. Particularly preferably, signal sequences of MHC class I molecule HLA-A*0201 may be used according to the present invention. Such an additional component may be bound e.g. to a cationic polymer or to any other component of the polymeric carrier as defined herein. Preferably this signal peptide, localisation signal or sequence or nuclear localisation signal or sequence (NLS), is bound to the polymeric carrier or to another component of the polymeric carrier via a (reversible) disulfide bond. For this purpose the (AA) component additionally comprises at least one —SH moiety as defined herein. The binding to any of components of the polymeric carrier may also be accomplished using an acid-labile bond, preferably via a side chain of any of components of the polymeric carrier, which allows to detach or release the additional component at lower pH-values, e.g. at physiological pH-values as defined herein.

Additionally, according to another alternative, the amino acid component (AA) may be a functional peptide or protein, which may modulate the functionality of the polymeric carrier accordingly. Such functional peptides or proteins as the amino acid component (AA) preferably comprise any peptides or proteins as defined herein, e.g. as defined below as therapeutically active proteins. According to one alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the polymeric carrier (in complex with a nucleic acid) from the endosome by insertion into the lipid layer of the liposome. These cell penetrating peptides (CPPs) or cationic peptides for transportation, may include, without being limited thereto protamine, nucleoline, spermine or spermidine, oligo- or poly-L-lysine (PLL), basic polypeptides, oligo or poly-arginine, cell penetrating peptides (CPPs), chimeric CPPs, such as Transportan, or MPG peptides, HIV-binding peptides, Tat, HIV-1 Tat (HIV), Tat-derived peptides, members of the penetratin family, e.g. Penetratin, Antennapedia-derived peptides (particularly from *Drosophila antennapedia*), pAntp, pIsl, etc., antimicrobial-derived CPPs e.g. Buforin-2, Bac715-24, SynB, SynB(1), pVEC, hCT-derived peptides, SAP, MAP, KALA, PpTG20, Loligomere, FGF, Lactoferrin, histones, VP22 derived or analog peptides, Pestivirus Ems, HSV, VP22 (Herpes simplex), MAP, KALA or protein transduction domains (PTDs, PpT620, proline-rich peptides, arginine-rich peptides, lysine-rich peptides, Pep-1, L-oligomers, Calcitonin peptide(s), etc. Such an amino acid component (AA) may also be bound to any component of the polymeric carrier as defined herein. Preferably it is bound to the polymeric carrier or to another component of the polymeric carrier via a (reversible) disulfide bond. For the above purpose, the amino acid component (AA) preferably comprises at least one —SH moiety as defined herein. The binding to any of components of the polymeric carrier may also be accomplished using an SH-moiety or an acid-labile bond, preferably via a side chain of any of components of the polymeric carrier which allows to detach or release the additional component at lower pH-values, e.g. at physiological pH-values as defined herein.

According to a last alternative, the amino acid component (AA) may consist of any peptide or protein which can execute any favourable function in the cell. Particularly preferred are peptides or proteins selected from therapeutically active proteins or peptides, from antigens, e.g. tumour antigens, pathogenic antigens (animal antigens, viral antigens, protozoan antigens, bacterial antigens, allergic antigens), autoimmune antigens, or further antigens, from allergens, from antibodies, from immunostimulatory proteins or peptides, from antigen-specific T cell receptors, or from any other protein or peptide suitable for a specific (therapeutic) application as defined below for coding nucleic acids. Particularly preferred are peptide epitopes from antigens as defined herein.

The polymeric carrier, which may be used to complex the at least one mRNA of the inventive vaccine may comprise at least one of the above mentioned cationic or polycationic peptides, proteins or polymers or further components, e.g. (AA), wherein any of the above alternatives may be combined with each other, and may be formed by polymerizing same in a polymerization condensation reaction via their —SH-moieties.

According to another aspect, the polymeric carrier, which may be used to complex the at least one mRNA of the inventive vaccine or single components thereof, e.g. of the above mentioned cationic or polycationic peptides, proteins or polymers or further components, e.g. (AA), may be further modified with a ligand, preferably a carbohydrate, more preferably a sugar, even more preferably mannose. Preferably this ligand is bound to the polymeric carrier or to a component of the polymeric carrier via a (reversible) disulfide bond or via Michael addition. In the case that the ligand is bound by a disulfide bond the ligand additionally comprises at least one —SH-moiety. These ligands may be used to direct the inventive polymeric carrier cargo complex to specific target cells (e.g. hepatocytes or antigen-presenting cells). In this context mannose is particularly preferred as ligand in the case that dendritic cells are the target especially for vaccination or adjuvant purposes.

According to one specific aspect, the entire inventive polymeric carrier may be formed by a polymerization condensation (of at least one) of the above mentioned cationic or polycationic peptides, proteins or polymers or further components, e.g. (AA), via their —SH-moieties in a first step and complexing the nucleic acid to such a polymeric carrier in a second step. The polymeric carrier may thus contain a number of at least one or even more of the same or different of the above defined cationic or polycationic peptides, proteins or polymers or further components, e.g. (AA), the number preferably determined by the above range.

According to one alternative specific aspect, the inventive polymeric carrier, which may be used to complex the at least one mRNA of the inventive vaccine is formed by carrying out the polymerization condensation of at least one of the above mentioned cationic or polycationic peptides, proteins or polymers or further components, e.g. (AA), via their —SH-moieties simultaneously to complexing the at least one mRNA encoding the at least one antigen to the (in situ prepared) polymeric carrier. Likewise, the polymeric carrier may thus also here contain a number of at least one or even more of the same or different of the above defined cationic or polycationic peptides, proteins or polymers or further components, e.g. (AA), the number preferably determined by the above range.

According to a further alternative aspect, the inventive polymeric carrier may be selected from a polymeric carrier molecule according to generic formula (VI):

$$L\text{-}P^1\text{-}S\text{-}[S\text{-}P^2\text{-}S]_n\text{-}S\text{-}P^3\text{-}L$$

wherein,

- $P^1$ and $P^3$ are different or identical to each other and represent a linear or branched hydrophilic polymer chain, each $P^1$ and $P^3$ exhibiting at least one —SH-moiety, capable to form a disulfide linkage upon condensation with component $P^2$, or alternatively with (AA), $(AA)_x$, or $[(AA)_x]_z$ if such components are used as a linker between $P^1$ and $P^2$ or $P^3$ and $P^2$) and/or with further components (e.g. (AA), $(AA)_x$, $[(AA)_x]_z$ or L), the linear or branched hydrophilic polymer chain selected independent from each other from polyethylene glycol (PEG), poly-N-(2-hydroxypropyl)methacrylamide, poly-2-(methacryloyloxy)ethyl phosphorylcholines, poly(hydroxyalkyl L-asparagine), poly(2-(methacryloyloxy)ethyl phosphorylcholine), hydroxyethyl starch or poly(hydroxyalkyl L-glutamine), wherein the hydrophilic polymer chain exhibits a molecular weight of about 1 kDa to about 100 kDa, preferably of about 2 kDa to about 25 kDa; or more preferably of about 2 kDa to about 10 kDa, e.g. about 5 kDa to about 25 kDa or 5 kDa to about 10 kDa;
- $P^2$ is a cationic or polycationic peptide or protein, e.g. as defined herein, and preferably having a length of about 3 to about 100 amino acids, more preferably having a length of about 3 to about 50 amino acids, even more preferably having a length of about 3 to about 25 amino acids, e.g. a length of about 3 to 10, 5 to 15, 10 to 20 or 15 to 25 amino acids, more preferably a length of about 5 to about 20 and even more preferably a length of about 10 to about 20; or is a cationic or polycationic polymer, e.g. as defined herein, typically having a molecular weight of about 0.5 kDa to about 30 kDa, including a molecular weight of about 1 kDa to about 20 kDa, even more preferably of about 1.5 kDa to about 10 kDa, or having a molecular weight of about 0.5 kDa to about 100 kDa, including a molecular weight of about 10 kDa to about 50 kDa, even more preferably of about 10 kDa to about 30 kDa;

each $P^2$ exhibiting at least two —SH-moieties, capable to form a disulfide linkage upon condensation with further components $P^2$ or component(s) $P^1$ and/or $P^3$ or alternatively with further components (e.g. (AA), $(AA)_x$, or $[(AA)_x]_z$);
- —S—S— is a (reversible) disulfide bond (the brackets are omitted for better readability), wherein S preferably represents sulphur or a —SH carrying moiety, which has formed a (reversible) disulfide bond. The (reversible) disulfide bond is preferably formed by condensation of —SH-moieties of either components $P^1$ and $P^2$, $P^2$ and $P^2$, or $P^2$ and $P^3$, or optionally of further components as defined herein (e.g. L, (AA), $(AA)_x$, $[(AA)_x]_z$, etc); The —SH-moiety may be part of the structure of these components or added by a modification as defined below;
- L is an optional ligand, which may be present or not, and may be selected independent from the other from RGD, Transferrin, Folate, a signal peptide or signal sequence, a localization signal or sequence, a nuclear localization signal or sequence (NLS), an antibody, a cell penetrating peptide, (e.g. TAT or KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) etc.;
- n is an integer, typically selected from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 4 to 9, 4 to 10, 3 to 20, 4 to 20, 5 to 20, or 10 to 20, or a range of about 3 to 15, 4 to 15, 5 to 15, or 10 to 15, or a range of about 6 to 11 or 7 to 10. Most preferably, n is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

As defined above, ligands (L), may be optionally used in the inventive polymeric carrier molecule according to generic formula (VI), e.g. for direction of the inventive carrier polymer and its entire "cargo" (the adjuvant component and/or the antigen of the inventive composition or vaccine composition) into specific cells. They may be selected independent from the other from RGD, Transferrin, Folate, a signal peptide or signal sequence, a localization signal or sequence, a nuclear localization signal or sequence (NLS), an antibody, a cell penetrating peptide (CPP), (e.g. TAT, KALA), a ligand of a receptor (e.g. cytokines, hormones, growth factors etc), small molecules (e.g. carbohydrates like mannose or galactose or synthetic ligands), small molecule agonists, inhibitors or antagonists of receptors (e.g. RGD peptidomimetic analogues) or any such molecule as further defined below, etc. Particularly preferred are cell penetrating peptides (CPPs), which induce a pH-mediated conformational change in the endosome and lead to an improved release of the inventive polymeric carrier (in complex with a nucleic acid) from the endosome by insertion into the lipid layer of the liposome. Such called CPPs or cationic peptides for transportation, may include, without being limited thereto protamine, nucleoline, spermine or spermidine, poly-L-lysine (PLL), basic polypeptides, poly-arginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila* antennapedia), pAntp, pIsl, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Ems, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc. Particularly preferred in this context is mannose as ligand to target antigen presenting cells which carries on their cell membrane mannose receptors. In a further preferred aspect of the first embodiment of the present invention galactose as optional ligand can be used to target hepatocytes. Such ligands may be attached to component $P^1$ and/or $P^3$ by reversible disulfide bonds as defined below or by any other possible chemical attachment, e.g. by amide formation (e.g. carboxylic acids, sulphonic acids, amines, etc), by Michael addition (e.g. maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components.

In the context of formula (VI) of the present invention components $P^1$ and $P^3$ represent a linear or branched hydrophilic polymer chain, containing at least one —SH-moiety, each $P^1$ and $P^3$ independently selected from each other, e.g. from polyethylene glycol (PEG), poly-N-(2-hydroxypropyl) methacrylamide, poly-2-(methacryloyloxy)ethyl phosphorylcholines, poly(hydroxyalkyl L-asparagine) or poly(hydroxyalkyl L-glutamine). $P^1$ and $P^3$ may be identical or different to each other. Preferably, each of hydrophilic polymers $P^1$ and $P^3$ exhibits a molecular weight of about 1 kDa to about 100 kDa, preferably of about 1 kDa to about 75 kDa, more preferably of about 5 kDa to about 50 kDa, even more preferably of about 5 kDa to about 25 kDa. Additionally, each of hydrophilic polymers $P^1$ and $P^3$ typically exhibits at least one —SH-moiety, wherein the at least one —SH-moiety is capable to form a disulfide linkage upon reaction with component $P^2$ or with component (AA) or $(AA)_x$, if used as linker between $P^1$ and $P^2$ or $P^3$ and $P^2$ as defined below and optionally with a further component, e.g. L and/or (AA) or $(AA)_x$, e.g. if two or more —SH-moieties are contained. The following subformulae "$P^1$—S—S—$P^2$" and "$P^2$—S—S—$P^3$" within generic formula (VI) above (the brackets are omitted for better readability), wherein any of S, $P^1$ and $P^3$ are as defined herein, typically represent a situation, wherein one —SH-moiety of hydrophilic polymers $P^1$ and $P^3$ was condensed with one —SH-moiety of component $P^2$ of generic formula (VI) above, wherein both sulphurs of these —SH-moieties form a disulfide bond —S—S— as defined herein in formula (VI). These —SH-moieties are typically provided by each of the hydrophilic polymers $P^1$ and $P^3$, e.g. via an internal cysteine or any further (modified) amino acid or compound which carries a —SH moiety. Accordingly, the subformulae "$P^1$—S—S—$P^2$" and "$P^2$—S—S—$P^3$" may also be written as "$P^1$-Cys-Cys-$P^2$" and "$P^2$-Cys-Cys-$P^3$", if the —SH-moiety is provided by a cysteine, wherein the term Cys-Cys represents two cysteines coupled via a disulfide bond, not via a peptide bond. In this case, the term "—S—S—" in these formulae may also be written as "—S-Cys", as "-Cys-S" or as "-Cys-Cys-". In this context, the term "-Cys-Cys-" does not represent a peptide bond but a linkage of two cysteines via their —SH-moieties to form a disulfide bond. Accordingly, the term "-Cys-Cys-" also may be understood generally as "-(Cys-S)—(S-Cys)-", wherein in this specific case S indicates the sulphur of the —SH-moiety of cysteine. Likewise, the terms "—S-Cys" and "—Cys-S" indicate a disulfide bond between a —SH containing moiety and a cysteine, which may also be written as "—S—(S-Cys)" and "-(Cys-S)—S". Alternatively, the hydrophilic polymers $P^1$ and $P^3$ may be modified with a —SH moiety, preferably via a chemical reaction with a compound carrying a —SH moiety, such that each of the hydrophilic polymers $P^1$ and $P^3$ carries at least one such —SH moiety. Such a compound carrying a —SH moiety may be e.g. an (additional) cysteine or any further (modified) amino acid, which carries a —SH moiety. Such a compound may also be any non-amino compound or moiety, which contains or allows to introduce a —SH moiety into hydrophilic polymers $P^1$ and $P^3$ as defined herein. Such non-amino compounds may be attached to the hydrophilic polymers $P^1$ and $P^3$ of formula (VI) of the polymeric carrier according to the present invention via chemical reactions or binding of compounds, e.g. by binding of a 3-thio propionic acid or thioimolane, by amide formation (e.g. carboxylic acids, sulphonic acids, amines, etc), by Michael addition (e.g maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components. A particularly preferred PEG derivate in this context is alpha-Methoxy-omega-mercapto poly(ethylene glycol). In each case, the SH-moiety, e.g. of a cysteine or of any further (modified) amino acid or compound, may be present at the terminal ends or internally at any position of hydrophilic polymers $P^1$ and $P^3$. As defined herein, each of hydrophilic polymers $P^1$ and $P^3$ typically exhibits at least one —SH-moiety preferably at one terminal end, but may also contain two or even more —SH-moieties, which may be used to additionally attach further components as defined herein, preferably further functional peptides or proteins e.g. a ligand, an amino acid component (AA) or $(AA)_x$, antibodies, cell penetrating peptides or enhancer peptides (e.g. TAT, KALA), etc.

According to one preferred alternative, such further functional peptides or proteins may comprise so called cell penetrating peptides (CPPs) or cationic peptides for transportation. Particularly preferred are CPPs, which induce a pH-mediated conformational change in the endosome and lead to an improved release of the inventive polymeric carrier (in complex with a nucleic acid) from the endosome by insertion into the lipid layer of the liposome. Such called cell penetrating peptides (CPPs) or cationic peptides for transportation, may include, without being limited thereto protamine, nucleoline, spermine or spermidine, poly-L-lysine (PLL), basic polypeptides, polyarginine, cell penetrating peptides (CPPs), chimeric CPPs, such as Transportan, or MPG peptides, HIV-binding peptides, Tat, HIV-1 Tat (HIV), Tat-derived peptides, oligoarginines, members of the penetratin family, e.g. Penetratin, Antennapedia-derived peptides (particularly from *Drosophila* antennapedia), pAntp, pIsl, etc., antimicrobial-derived CPPs e.g. Buforin-2, Bac715-24, SynB, SynB(1), pVEC, hCT-derived peptides, SAP, MAP, PpTG20, Proline-rich peptides, Loligomers, Arginine-rich peptides, Calcitonin-peptides, FGF, Lactoferrin, poly-L-Lysine, poly-Arginine, histones, VP22 derived or analog peptides, Pestivirus Ems, HSV, VP22 (Herpes simplex), MAP, KALA or protein transduction domains (PTDs, PpT620, prolin-rich peptides, arginine-rich peptides, lysine-rich peptides, Pep-1, L-oligomers, Calcitonin peptide(s), etc.

According to a further preferred aspect of the first embodiment of the present invention, each of hydrophilic polymers $P^1$ and $P^3$ of formula (VI) of the polymeric carrier used according to the present invention may also contain at least one further functional moiety, which allows attaching further components as defined herein, e.g. a ligand as defined above, or functionalities which allow the attachment of further components, e.g. by amide formation (e.g. carboxylic acids, sulphonic acids, amines, etc), by Michael addition (e.g maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow S-type substitution reactions (e.g halogenalkans, thiols, alcohols, amines, hydrazines, hydrazides, sulphonic acid esters, oxyphosphonium salts) or other chemical moieties which can be utilized in the attachment of further components. Further functional moieties may comprise an amino acid component (AA) as defined herein or $(AA)_x$, wherein (AA) is preferably an amino component as defined above. In the above context, x is preferably an integer and may be selected from a range of about 1 to 100, preferably from a range of about 1 to 50, more preferably 1 to 30, and even more preferably selected from a number comprising 1, 2, 3, 4, 5, 6, 7, 8, 9, 10, 11, 12, 13, 14 or 15-30, e.g. from a range of about 1 to 30, from a range of about 1 to 15, or from a number comprising 1, 2, 3, 4, 5, 6, 7, 8, 9, 10, 11, 12, 13, 14 or 15, or may be selected from a range formed by any two of the afore mentioned values. Most preferably, x is 1. Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component [S—$P^2$—S]n within formula (VI) of the inventive polymeric carrier.

In the context of the entire formula (VI) of the inventive polymeric carrier may be preferably defined as follows:

$$L\text{-}P^1\text{-}S\text{-}[Cys\text{-}P^2\text{-}Cys]_n\text{-}S\text{-}P^3\text{-}L$$

wherein L, $P^1$, $P^2$, $P^3$ and n are as defined herein, S is sulphur and each Cys provides for one —SH-moiety for the disulfide bond.

According to a particular aspect, the inventive polymeric carrier according to formula (VI) as defined above, may comprise at least one amino acid component (AA) or $(AA)_x$, as defined above. Such an amino acid component (AA) or $(AA)_x$ may be contained in every part of the inventive polymeric carrier according to formula (VI) above and therefore may be attached to all components of the inventive polymeric carrier according to formula (VI). It is particularly preferred that amino acid component (AA) or $(AA)_x$ is present as a ligand or part of the repetitive component $[S—P^2—S]_n$ within formula (VI) of the inventive polymeric carrier. The amino acid component (AA) or $(AA)_x$ preferably contains or is flanked (e.g. terminally) by at least one —SH containing moiety, which allows introducing this component (AA) or $(AA)_x$ via a disulfide bond into the polymeric carrier according to formula (VI) as defined herein. Such a —SH-containing moiety may be any —SH containing moiety (or, of course, one sulphur of a disulfide bond), e.g. a cysteine residue. In the specific case that the —SH containing moiety represents a cysteine, the amino acid component $(AA)_x$ may also be read as -Cys-$(AA)_x$- or -Cys-$(AA)_x$-Cys- wherein Cys represents Cysteine and provides for the necessary —SH-moiety for a disulfide bond. The —SH containing moiety may be also introduced into the amino acid component $(AA)_x$ using any of modifications or reactions as shown above for components $P^1$, $P^2$ or $P^3$. In the specific case that the amino acid component $(AA)_x$ is linked to two components of the inventive polymeric carrier according to formula (VI) it is preferred that (AA) or $(AA)_x$ contains at least two —SH-moieties, e.g. at least two Cysteines, preferably at its terminal ends. This is particularly preferred if (AA) or $(AA)_x$ is part of the repetitive component $[S—P^2—S]_n$. Alternatively, the amino acid component (AA) or $(AA)_x$ is introduced into the inventive polymeric carrier according to formula (VI) as defined herein via any chemical possible addition reaction. Therefore the amino acid component (AA) or $(AA)_x$ contains at least one further functional moiety, which allows attaching same to a further component as defined herein, e.g. component $P^1$ or $P^3$, $P^2$, L, or a further amino acid component (AA) or $(AA)_x$, etc. Such functional moieties may be selected from functionalities which allow the attachment of further components, e.g. functionalities as defined herein, e.g. by amide formation (e.g. carboxylic acids, sulphonic acids, amines, etc), by Michael addition (e.g maleinimide moieties, α,β unsatured carbonyls, etc), by click chemistry (e.g. azides or alkines), by alkene/alkine methatesis (e.g. alkenes or alkines), imine or hydrozone formation (aldehydes or ketons, hydrazins, hydroxylamins, amines), complexation reactions (avidin, biotin, protein G) or components which allow Sn-type substitution reactions (e.g halogenalkans, thiols, alcohols, amines, hydrazines, hydrazides, sulphonic acid esters, oxyphosphonium salts) or other chemical moieties which can be utilized in the attachment of further components.

The amino acid component (AA) or $(AA)_x$ in the polymeric carrier of formula (VI) may also occur as a mixed repetitive amino acid component $[(AA)_x]_z$, wherein the number of amino acid components (AA) or $(AA)_x$ is further defined by integer z. In this context, z may be selected from a range of about 1 to 30, preferably from a range of about 1 to 15, more preferably 1 to 10 or 1 to 5 and even more preferably selected from a number selected from 1, 2, 3, 4, 5, 6, 7, 8, 9, 10, 11, 12, 13, 14 or 15, or may be selected from a range formed by any two of the afore mentioned values.

According to a specific and particularly preferred alternative, the amino acid component (AA) or $(AA)_x$, preferably written as S-$(AA)_x$-S or [S-$(AA)_x$-S] may be used to modify component $P^2$, particularly the content of component $S—P^2—S$ in repetitive component $[S—P^2—S]_n$ of the polymeric carrier of formula (VI) above. This may be represented in the context of the entire polymeric carrier according to formula (VI) e.g. by following formula (VIa):

$$L\text{-}P^1\text{-}S\text{-}\{[S\text{-}P^2\text{-}S]_a[S\text{-}(AA)_x\text{-}S]_b\}\text{-}S\text{-}P^3\text{-}L,$$

wherein x, S, L, AA, $P^1$, $P^2$ and $P^3$ are preferably as defined herein. In formula (VIa) above, any of the single components $[S—P^2—S]$ and $[S\text{-}(AA)_x\text{-}S]$ may occur in any order in the subformula $\{[S—P^2—S]_a[S\text{-}(AA)_x\text{-}S]_b\}$. The numbers of single components $[S—P^2—S]$ and $[S\text{-}(AA)_x\text{-}S]$ in the subformula $\{[S—P^2—S]_a[S\text{-}(AA)_x\text{-}S]_b\}$ are determined by integers a and b, wherein a+b=n. n is an integer and is defined as above for formula (VI).

a is an integer, typically selected independent from integer b from a range of about 1 to 50, preferably from a range of about 1, 2 or 3 to 30, more preferably from a range of about 1, 2, 3, 4, or 5 to 25, or a range of about 1, 2, 3, 4, or 5 to 20, or a range of about 1, 2, 3, 4, or 5 to 15, or a range of about 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, a is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

b is an integer, typically selected independent from integer a from a range of about 0 to 50 or 1 to 50, preferably from a range of about 0, 1, 2 or 3 to 30, more preferably from a range of about 0, 1, 2, 3, 4, or 5 to 25, or a range of about 0, 1, 2, 3, 4, or 5 to 20, or a range of about 0, 1, 2, 3, 4, or 5 to 15, or a range of about 0, 1, 2, 3, 4, or 5 to 10, including e.g. a range of about 3 to 20, 4 to 20, 5 to 20, or 10 to 20, or a range of about 3 to 15, 4 to 15, 5 to 15, or 10 to 15, or a range of about 6 to 11 or 7 to 10. Most preferably, b is in a range of about 1, 2, 3, 4, or 5 to 10, more preferably in a range of about 1, 2, 3, or 4 to 9, in a range of about 1, 2, 3, or 4 to 8, or in a range of about 1, 2, or 3 to 7.

According to one preferred aspect, the mRNA of the inventive vaccine encoding at least one antigen as defined above may be formulated together with a cationic or polycationic compound and/or with a polymeric carrier, preferably as defined herein.

According to a further preferred aspect, the mRNA of the inventive vaccine encoding at least one antigen as defined above may be formulated together with an (adjuvant) component. According to a particularly preferred aspect, the mRNA of the inventive vaccine encoding at least one antigen as defined above may be formulated to comprise a) an (adjuvant) component, comprising or consisting of at least one immunostimulatory nucleic acid, complexed with a cationic or polycationic compound and/or with a polymeric carrier, preferably as defined herein, and b) at least one free mRNA, encoding an antigen, preferably as defined herein for the inventive vaccine.

In the above context, a cationic or polycationic compound and/or a polymeric carrier used to complex the at least one immunostimulatory nucleic acid in the adjuvant component, may be selected from a cationic or polycationic compound and/or a polymeric carrier as defined above.

Furthermore, an immunostimulatory nucleic acid as defined above for the adjuvant component may be preferably selected from an mRNA as defined herein for the inventive vaccine, encoding at least one antigen. Alternatively, such an immunostimulatory nucleic acid may be selected from an immunostimulatory nucleic acid, as defined herein, preferably an immunostimulatory RNA (isRNA) as defined herein.

In this context, an immunostimulatory nucleic acid, as used herein, is preferably selected from immunostimulatory nucleic acids which are known to bind to TLR receptors. Such an immunostimulatory nucleic acid can be in the form of a(n) (immunostimulatory) CpG nucleic acid, in particular CpG-RNA or CpG-DNA, which preferably induces an innate immune response. A CpG-RNA or CpG-DNA used according to the invention can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid used according to the invention is preferably in the form of CpG-RNA, more preferably in the form of single-stranded CpG-RNA (ss CpG-RNA). Also preferably, such CpG nucleic acids have a length as described above. Preferably the CpG motifs are unmethylated.

Furthermore, an immunostimulatory nucleic acid, as used herein, is preferably selected from an immunostimulatory RNA (isRNA), which preferably elicits an innate immune response. Preferably, the immunostimulatory RNA may be a single-stranded, a double-stranded or a partially double-stranded RNA, more preferably a single-stranded RNA, and/or a circular or linear RNA, more preferably a linear RNA. More preferably, the immunostimulatory RNA may be a (linear) single-stranded RNA. Even more preferably, the immunostimulatory RNA may be a (long) (linear) (single-stranded) non-coding RNA. In this context it is particular preferred that the isRNA carries a triphosphate at its 5'-end which is the case for in vitro transcribed RNA. An immunostimulatory RNA may also occur as a short RNA oligonucleotide as defined herein. An immunostimulatory RNA as used herein may furthermore be selected from any class of RNA molecules, found in nature or being prepared synthetically, and which can induce an innate immune response and may support an adaptive immune response induced by an antigen. In this context, an immune response may occur in various ways. A substantial factor for a suitable (adaptive) immune response is the stimulation of different T cell sub-populations. T-lymphocytes are typically divided into two sub-populations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T cells. Th2 cells, on the other hand, promote the humoral immune response by stimulation of B cells for conversion into plasma cells and by formation of antibodies (e.g. against antigens). The Th1/Th2 ratio is therefore of great importance in the induction and maintenance of an adaptive immune response. In connection with the present invention, the Th1/Th2 ratio of the (adaptive) immune response is preferably shifted in the direction towards the cellular response (Th1 response) and a cellular immune response is thereby induced. According to one example, the innate immune system which may support an adaptive immune response may be activated by ligands of Toll-like receptors (TLRs). TLRs are a family of highly conserved pattern recognition receptor (PRR) polypeptides that recognize pathogen-associated molecular patterns (PAMPs) and play a critical role in innate immunity in mammals. Currently at least thirteen family members, designated TLR1-TLR13 (Toll-like receptors: TLR1, TLR2, TLR3, TLR4, TLR5, TLR6, TLR7, TLR8, TLR9, TLR10, TLR11, TLR12 or TLR13), have been identified. Furthermore, a number of specific TLR ligands have been identified. It was e.g. found that unmethylated bacterial DNA and synthetic analogs thereof (CpG DNA) are ligands for TLR9 (Hemmi H et al. (2000) Nature 408:740-5; Bauer S et al. (2001) Proc Natl. Acad. Sci. USA 98, 9237-42). Furthermore, it has been reported that ligands for certain TLRs include certain nucleic acid molecules and that certain types of RNA are immunostimulatory in a sequence-independent or sequence-dependent manner, wherein these various immunostimulatory RNAs may e.g. stimulate TLR3, TLR7, or TLR8, or intracellular receptors such as RIG-I, MDA-5, etc.

Preferably, an immunostimulatory nucleic acid, preferably an immunostimulatory RNA (isRNA), as used herein, may comprise any RNA sequence known to be immunostimulatory, including, without being limited thereto, RNA sequences representing and/or encoding ligands of TLRs, preferably selected from human family members TLR1-TLR10 or murine family members TLR1-TLR13, more preferably selected from (human) family members TLR1-TLR10, even more preferably from TLR7 and TLR8, ligands for intracellular receptors for RNA (such as RIG-I or MDA-5, etc.) (see e.g. Meylan, E., Tschopp, J. (2006). Toll-like receptors and RNA helicases: two parallel ways to trigger antiviral responses. Mol. Cell 22, 561-569), or any other immunostimulatory RNA sequence. Furthermore, (classes of) immunostimulatory RNA molecules, used as a further compound of the inventive vaccine, may include any other RNA capable of eliciting an immune response. Without being limited thereto, such an immunostimulatory RNA may include ribosomal RNA (rRNA), transfer RNA (tRNA), messenger RNA (mRNA), and viral RNA (vRNA). Such an immunostimulatory RNA may comprise a length of 1000 to 5000, of 500 to 5000, of 5 to 5000, or of 5 to 1000, 5 to 500, 5 to 250, of 5 to 100, of 5 to 50 or of 5 to 30 nucleotides.

According to a particularly preferred embodiment, an immunostimulatory nucleic acid sequence, particularly an isRNA, as used herein, may consist of or comprise a nucleic acid of formula (I) or (II):

$$G_l X_m G_n, \quad \text{(formula (I))}$$

wherein:

- G is guanosine, uracil or an analogue of guanosine or uracil;
- X is guanosine, uracil, adenosine, thymidine, cytosine or an analogue of the abovementioned nucleotides;
- l is an integer from 1 to 40,
  - wherein
  - when l=1 G is guanosine or an analogue thereof,
  - when l>1 at least 50% of the nucleotides are guanosine or an analogue thereof;
- m is an integer and is at least 3;
  - wherein
  - when m=3× is uracil or an analogue thereof,
  - when m>3 at least 3 successive uracils or analogues of uracil occur;
- n is an integer from 1 to 40,
  - wherein
  - when n=1 G is guanosine or an analogue thereof,
  - when n>1 at least 50% of the nucleotides are guanosine or an analogue thereof.

$$C_l X_m C_n, \quad \text{(formula (II))}$$

wherein:

- C is cytosine, uracil or an analogue of cytosine or uracil;
- X is guanosine, uracil, adenosine, thymidine, cytosine or an analogue of the abovementioned nucleotides;
- l is an integer from 1 to 40,
  - wherein
  - when l=1 C is cytosine or an analogue thereof,
  - when l>1 at least 50% of the nucleotides are cytosine or an analogue thereof;
- m is an integer and is at least 3;
  - wherein
  - when m=3× is uracil or an analogue thereof,
  - when m>3 at least 3 successive uracils or analogues of uracil occur;
- n is an integer from 1 to 40,
  - wherein
  - when n=1 C is cytosine or an analogue thereof,
  - when n>1 at least 50% of the nucleotides are cytosine or an analogue thereof.

The nucleic acids of formula (I) or (II), which may be used as an immunostimulatory nucleic acid sequence, particularly an isRNA, may be relatively short nucleic acid molecules with a typical length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of formula (I) or (II) has a maximum length of e.g. 100 nucleotides, m will typically be <=98. The number of nucleotides G in the nucleic acid of formula (I) is determined by 1 or n. 1 and n, independently of one another, are each an integer from 1 to 40, wherein when 1 or n=1 G is guanosine or an analogue thereof, and when 1 or n>1 at least 50% of the nucleotides are guanosine or an analogue thereof. For example, without implying any limitation, when 1 or n=4 $G_1$ or $G_n$ can be, for example, a GUGU, GGUU, UGUG, UUGG, GUUG, GGGU, GGUG, GUGG, UGGG or GGGG, etc.; when 1 or n=5 $G_1$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (I) according to the invention is preferably not a uracil. Similarly, the number of nucleotides C in the nucleic acid of formula (II) according to the invention is determined by 1 or n. 1 and n, independently of one another, are each an integer from 1 to 40, wherein when 1 or n=1 C is cytosine or an analogue thereof, and when 1 or n>1 at least 50% of the nucleotides are cytosine or an analogue thereof. For example, without implying any limitation, when 1 or n=4, $C_1$ or $C_n$ can be, for example, a CUCU, CCUU, UCUC, UUCC, CUUC, CCCU, CCUC, CUCC, UCCC or CCCC, etc.; when 1 or n=5 $C_1$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (II) according to the invention is preferably not a uracil. Preferably, for formula (I), when 1 or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_1$ and/or $G_n$ are uracil or an analogue thereof, as defined hereinbefore. Also preferably, 1 and n, independently of one another, are each an integer from 2 to 30, more preferably an integer from 2 to 20 and yet more preferably an integer from 2 to 15. The lower limit of 1 or n can be varied if necessary and is at least 1, preferably at least 2, more preferably at least 3, 4, 5, 6, 7, 8, 9 or 10. This definition applies correspondingly to formula (II).

According to a particularly preferred embodiment, a nucleic acid according to any of formulas (I) or (II) above, which may be used as an immunostimulatory nucleic acid sequence, particularly an isRNA, may be selected from a sequence consisting or comprising any of the following sequences:

According to a particularly preferred embodiment, a nucleic acid according to any of formulas (I) or (II) above, which may be used as an immunostimulatory nucleic acid sequence, particularly an isRNA, may be selected from a sequence consisting or comprising any of the following sequences:

(SEQ ID NO: 289)
GGUUUUUUUUUUUUUUUGGG;

(SEQ ID NO: 290)
GGGGGUUUUUUUUUUGGGGG;

(SEQ ID NO: 291)
GGGGGUUUUUUUUUUUUUUUUUUUUUUUUUUUUUUGGGGG;

(SEQ ID NO: 292)
GUGUGUGUGUUUUUUUUUUUUUUUUUUUUGUGUGUGUGU;

(SEQ ID NO: 293)
GGUUGGUUGGUUUUUUUUUUUUUUUUUUGGUUGGUUGGUU;

(SEQ ID NO: 294)
GGGGGGGGGUUUGGGGGGGG;

(SEQ ID NO: 295)
GGGGGGGGUUUUGGGGGGGG;

(SEQ ID NO: 296)
GGGGGGGUUUUUUGGGGGGG;

(SEQ ID NO: 297)
GGGGGGGUUUUUUUGGGGGG;

(SEQ ID NO: 298)
GGGGGGUUUUUUUUGGGGGG;

(SEQ ID NO: 299)
GGGGGGUUUUUUUUUGGGGG;

(SEQ ID NO: 300)
GGGGGGUUUUUUUUUUGGGG;

(SEQ ID NO: 301)
GGGGGUUUUUUUUUUUGGGG;

(SEQ ID NO: 302)
GGGGGUUUUUUUUUUUUGGG;

(SEQ ID NO: 303)
GGGGUUUUUUUUUUUUUGGG;

-continued (SEQ ID NO: 304)
GGGGUUUUUUUUUUUUUUGG;

(SEQ ID NO: 305)
GGUUUUUUUUUUUUUUUUGG;

(SEQ ID NO: 306)
GUUUUUUUUUUUUUUUUUUG;

(SEQ ID NO: 307)
GGGGGGGGGGUUUGGGGGGGGG;

(SEQ ID NO: 308)
GGGGGGGGGUUUUGGGGGGGGG;

(SEQ ID NO: 309)
GGGGGGGGUUUUUUGGGGGGGG;

(SEQ ID NO: 310)
GGGGGGGGUUUUUUUGGGGGGG;

(SEQ ID NO: 311)
GGGGGGGUUUUUUUUGGGGGGG;

(SEQ ID NO: 312)
GGGGGGGUUUUUUUUUGGGGGG;

(SEQ ID NO: 313)
GGGGGGGUUUUUUUUUUGGGGG;

(SEQ ID NO: 314)
GGGGGGUUUUUUUUUUUGGGGG;

(SEQ ID NO: 315)
GGGGGGUUUUUUUUUUUUGGGG;

(SEQ ID NO: 316)
GGGGGUUUUUUUUUUUUUGGGG;

(SEQ ID NO: 317)
GGGGGUUUUUUUUUUUUUUGGG;

(SEQ ID NO: 318)
GGGUUUUUUUUUUUUUUUUGGG;

(SEQ ID NO: 319)
GGUUUUUUUUUUUUUUUUUUGG;

(SEQ ID NO: 320)
GGGGGGGGGGGUUUGGGGGGGGGG;

(SEQ ID NO: 321)
GGGGGGGGGGUUUUGGGGGGGGGG;

(SEQ ID NO: 322)
GGGGGGGGGUUUUUUGGGGGGGGG;

(SEQ ID NO: 323)
GGGGGGGGGUUUUUUUGGGGGGGG;

(SEQ ID NO: 324)
GGGGGGGGUUUUUUUUGGGGGGGG;

(SEQ ID NO: 325)
GGGGGGGGUUUUUUUUUGGGGGGG;

(SEQ ID NO: 326)
GGGGGGGGUUUUUUUUUUGGGGGG;

(SEQ ID NO: 327)
GGGGGGGUUUUUUUUUUUGGGGGG;

(SEQ ID NO: 328)
GGGGGGGUUUUUUUUUUUUGGGGG;

(SEQ ID NO: 329)
GGGGGGUUUUUUUUUUUUUGGGGG;

(SEQ ID NO: 330)
GGGGGGUUUUUUUUUUUUUUGGGG;

-continued (SEQ ID NO: 331)
GGGGUUUUUUUUUUUUUUUGGGG;

(SEQ ID NO: 332)
GGGUUUUUUUUUUUUUUUUUGGG;

(SEQ ID NO: 333)
GUUUUUUUUUUUUUUUUUUUUUUUUUUUUUG;

(SEQ ID NO: 334)
GGUUUUUUUUUUUUUUUUUUUUUUUUUUUUUGG;

(SEQ ID NO: 335)
GGGUUUUUUUUUUUUUUUUUUUUUUUUUUUUUGGG;

(SEQ ID NO: 336)
GGGGUUUUUUUUUUUUUUUUUUUUUUUUUUUUUGGG;

(SEQ ID NO: 337)
GGGGGUUUUUUUUUUUUUUUUUUUUUUUUUUUUUGGGG;

(SEQ ID NO: 338)
GGGGGGUUUUUUUUUUUUUUUUUUUUUUUUUUUUUGGGGG;

(SEQ ID NO: 339)
GGGGGGGUUUUUUUUUUUUUUUUUUUUUUUUUUUUUGGGGGG;

(SEQ ID NO: 340)
GGGGGGGGUUUUUUUUUUUUUUUUUUUUUUUUUUUUUGGGGGGG;

(SEQ ID NO: 341)
GGGGGGGGGUUUUUUUUUUUUUUUUUUUUUUUUUUUUUGGGGGGGG;

(SEQ ID NO: 342)
GGUUUGG;

(SEQ ID NO: 343)
GGUUUUGG;

(SEQ ID NO: 344)
GGUUUUUGG;

(SEQ ID NO: 345)
GGUUUUUUGG;

(SEQ ID NO: 346)
GGUUUUUUUGG;

(SEQ ID NO: 347)
GGUUUUUUUUGG;

(SEQ ID NO: 348)
GGUUUUUUUUUGG;

(SEQ ID NO: 349)
GGUUUUUUUUUUGG;

(SEQ ID NO: 350)
GGUUUUUUUUUUUGG;

(SEQ ID NO: 351)
GGUUUUUUUUUUUUGG;

(SEQ ID NO: 352)
GGUUUUUUUUUUUUUGG;

(SEQ ID NO: 353)
GGUUUUUUUUUUUUUUGG;

(SEQ ID NO: 354)
GGUUUUUUUUUUUUUUUGG;

(SEQ ID NO: 355)
GGGUUUGGG;

(SEQ ID NO: 356)
GGGUUUUGGG;

(SEQ ID NO: 357)
GGGUUUUUGGG;

(SEQ ID NO: 358)
GGGUUUUUUGGG;

(SEQ ID NO: 359)
GGGUUUUUUUGGG;

(SEQ ID NO: 360)
GGGUUUUUUUUGGG;

(SEQ ID NO: 361)
GGGUUUUUUUUUGGG;

(SEQ ID NO: 362)
GGGUUUUUUUUUUGGG;

(SEQ ID NO: 363)
GGGUUUUUUUUUUUGGG;

(SEQ ID NO: 364)
GGGUUUUUUUUUUUUGGG;

(SEQ ID NO: 365)
GGGUUUUUUUUUUUUUGGG;

(SEQ ID NO: 366)
GGGUUUUUUUUUUUUUUUGGGUUUUUUUUUUUUUUUGGGUUUUUUUUU
UUUUUUGGG;

(SEQ ID NO: 367)
GGGUUUUUUUUUUUUUUUGGGGGUUUUUUUUUUUUUUUGGG;

(SEQ ID NO: 368)
GGGUUUGGGUUUGGGUUUGGGUUUGGGUUUGGGUUUGGGUUUGGGUUU
GGG;

(short GU-rich, SEQ ID NO: 369)
GGUUUUUUUUUUUUUUUGGG
or (SEQ ID NO: 370)
CCCUUUUUUUUUUUUUUUCCCUUUUUUUUUUUUUUUCCCUUUUUUUUU
UUUUUUCCC (SEQ ID NO: 371)
CCCUUUCCCUUUCCCUUUCCCUUUCCCUUUCCCUUUCCCUUUCCCUUU
CCC (SEQ ID NO: 372)
CCCUUUUUUUUUUUUUUUCCCCCUUUUUUUUUUUUUUUCCC or from a sequence having at least 60%, 70%, 80%, 90%, or even 95% sequence identity with any of these sequences.

According to a further particularly preferred embodiment, an immunostimulatory nucleic acid sequence, particularly an isRNA, as used herein, may consist of or comprise a nucleic acid of formula (III) or (IV):

$$(N_u G_l X_m G_n N_v)_a, \quad \text{(formula (III))}$$

wherein:

G is guanosine (guanine), uridine (uracil) or an analogue of guanosine (guanine) or uridine (uracil), preferably guanosine (guanine) or an analogue thereof;

X is guanosine (guanine), uridine (uracil), adenosine (adenine), thymidine (thymine), cytidine (cytosine), or an analogue of these nucleotides (nucleosides), preferably uridine (uracil) or an analogue thereof;

N is a nucleic acid sequence having a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
 wherein
 when l=1, G is guanosine (guanine) or an analogue thereof,
 when l>1, at least 50% of these nucleotides (nucleosides) are guanosine (guanine) or an analogue thereof;

m is an integer and is at least 3;
 wherein
 when m=3, X is uridine (uracil) or an analogue thereof, and
 when m>3, at least 3 successive uridines (uracils) or analogues of uridine (uracil) occur;

n is an integer from 1 to 40,
 wherein
 when n=1, G is guanosine (guanine) or an analogue thereof,
 when n>1, at least 50% of these nucleotides (nucleosides) are guanosine (guanine) or an analogue thereof;

u, v may be independently from each other an integer from 0 to 50,
 preferably wherein when u=0, v≥1, or
 when v=0, u≥1;

wherein the nucleic acid molecule of formula (III) has a length of at least 50 nucleotides, preferably of at least 100 nucleotides, more preferably of at least 150 nucleotides, even more preferably of at least 200 nucleotides and most preferably of at least 250 nucleotides.

$$(N_u C_l X_m C_n N_v)_a \qquad \text{(formula IV))}$$

wherein:

C is cytidine (cytosine), uridine (uracil) or an analogue of cytidine (cytosine) or uridine (uracil), preferably cytidine (cytosine) or an analogue thereof;

X is guanosine (guanine), uridine (uracil), adenosine (adenine), thymidine (thymine), cytidine (cytosine) or an analogue of the above-mentioned nucleotides (nucleosides), preferably uridine (uracil) or an analogue thereof;

N is each a nucleic acid sequence having independent from each other a length of about 4 to 50, preferably of about 4 to 40, more preferably of about 4 to 30 or 4 to 20 nucleic acids, each N independently being selected from guanosine (guanine), uridine (uracil), adenosine (adenine), thymidine (thymine), cytidine (cytosine) or an analogue of these nucleotides (nucleosides);

a is an integer from 1 to 20, preferably from 1 to 15, most preferably from 1 to 10;

l is an integer from 1 to 40,
 wherein
 when l=1, C is cytidine (cytosine) or an analogue thereof,
 when l>1, at least 50% of these nucleotides (nucleosides) are cytidine (cytosine) or an analogue thereof;

m is an integer and is at least 3;
 wherein
 when m=3, X is uridine (uracil) or an analogue thereof,
 when m>3, at least 3 successive uridines (uracils) or analogues of uridine (uracil) occur;

n is an integer from 1 to 40,
 wherein
 when n=1, C is cytidine (cytosine) or an analogue thereof,
 when n>1, at least 50% of these nucleotides (nucleosides) are cytidine (cytosine) or an analogue thereof.

u, v may be independently from each other an integer from 0 to 50,
 preferably wherein when u=0, v≥1, or
 when v=0, u≥1;

wherein the nucleic acid molecule of formula (IV) according to the invention has a length of at least 50 nucleotides, preferably of at least 100 nucleotides, more preferably of at least 150 nucleotides, even more preferably of at least 200 nucleotides and most preferably of at least 250 nucleotides.

Any of the definitions given above in formulae (I) and (II), e.g. for elements N (i.e. $N_u$ and $N_v$) and X ($X_m$), particularly the core structure as defined above, as well as for integers a, l, m, n, u and v, similarly apply to elements of formula (III) and (IV) correspondingly. The definition of bordering elements $N_u$ and $N_v$ in formula (IV) is identical to the definitions given above for $N_u$ and $N_v$ in formula (IV).

According to a very particularly preferred embodiment, the inventive nucleic acid molecule according to formula (IV), which may be used as an immunostimulatory nucleic acid sequence, particularly an isRNA, may be selected from e.g. any of the following sequences:

(SEQ ID NO: 373)
UAGCGAAGCUCUUGGACCUAGGUUUUUUUUUUUUUUUGGGUGCGUUCCUAGAA-
GUACACG (SEQ ID NO: 374)
UAGCGAAGCUCUUGGACCUAGGUUUUUUUUUUUUUUUGGGUGCGUUCCUAGAA-
GUACACG AUCGCUUCGA GAACCUGGAUCCAAAAAAAAAAAAAAACCCAC-
GCAAGGAUCUUCAUGUGC (SEQ ID NO: 375)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-

-continued

CUAGGUCGUCAGUUGACCAGUCCGCCACUAGACGUGAGUCCGUCAAAGCAGUUA-
GAUGUUACACUCUAUUAGAUC (SEQ ID NO: 376)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-
CUAGGUCGUCAGUUGACCAGUCCGCCACUAGACGUGAGUCCGUCAAAGCAGUUA-
GAUGUUACACUCUAUUAGAUCUCGGAUUACAGCUGGAAGGAGCAGGAGUAGUG-
UUCUUGCUCUAAGUACCGAGUGUGCCCAAUACCCGAUCAGCUUAUUAACGAAC-
GGCUCCUCCUCUUAGACUGCAGCGUAAGUGCGGAAUCUGGGGAUCAAAUUACU-
GACUGCCUGGAUUACCCUCGGACAUAUAACCUUGUAGCAC-
GCUGUUGCUGUAUAGGUGACCAACGCCCACUCGAGUAGACCAGCUCU-
CUUAGUCCGGACAAUGAUAGGAGGCGCGGUCAAUCUACUUCUGGCUAGUU-
AAGAAUAGGCUGCACCGACCUCUAUAAGUAGCGUGUCCUCUAG (SEQ ID NO: 377)
GGGAGAAAGCUCAAGCUUGGAGCAAUGCCCGCACAUUGAGGAAACCGAGUUG-
CAUAUCUCAGAGUAUUGGCCCCCGUGUAGGUUAUUCUUGACAGACAGUG-
GAGCUUAUUCACUCCCAGGAUCCGAGUCGCAUACUACGGUACUGGUGACAGAC-
CUAGGUCGUCAGUUGACCAGUCCGCCACUAGACGUGAGUCCGUCAAAGCAGUUA-
GAUGUUACACUCUAUUAGAUCUCGGAUUACAGCUGGAAGGAGCAGGAGUAGUG-
UUCUUGCUCUAAGUACCGAGUGUGCCCAAUACCCGAUCAGCUUAUUAACGAAC-
GGCUCCUCCUCUUAGACUGCAGCGUAAGUGCGGAAUCUGGGGAUCAAAUUACU-
GACUGCCUGGAUUACCCUCGGACAUAUAACCUUGUAGCAC-
GCUGUUGCUGUAUAGGUGACCAACGCCCACUCGAGUAGACCAGCUCU-
CUUAGUCCGGACAAUGAUAGGAGGCGCGGUCAAUCUACUUCUGGCUAGUU-
AAGAAUAGGCUGCACCGACCUCUAUAAGUAGCGUGUCCUCUAGAGCUAC-
GCAGGUUCGCAAUAAAAGCGUUGAUUAGUGUGCAUAGAACAGACCU-
CUUAUUCGGUGAAACGCCAGAAUGCUAAAUUCCAAUAACUCUUCCCAAAAC-
GCGUACGGCCGAAGACGCGCGCUUAUCUUGUGUACGUUCUCGCACAUGGAA-
GAAUCAGCGGGCAUGGUGGUAGGGCAAUAGGGGAGCUGGGUAG-
CAGCGAAAAAGGGCCCCUGCGCAC-
GUAGCUUCGCUGUUCGUCUGAAACAACCCGG-
CAUCCGUUGUAGCGAUCCCGUUAUCAGUGUUAUUCUUGUGCGCACUAAGAU-
UCAUGGUGUAGUCGACAAUAACAGCGUCUUGGCAGAUUCUGGUCACGUG-
CCCUAUGCCCGGGCUUGUGCCUCUCAGGUGCACAGCGAUACUUAAA-
GCCUUCAAGGUACUCGACGUGGGUACCGAUUCGUGACACUUCCUAAGAU-
UAUUCCACUGUGUUAGCCCCGCACCGCCGACCUAAACUGGUCCAAUGUAUAC-
GCAUUCGCUGAGCGGAUCGAUAAUAAAAGCUUGAAUU (SEQ ID NO: 378)
GGGAGAAAGCUCAAGCUUAUCCAAGUAGGCUGGUCACCUGUACAAC-
GUAGCCGGUAUUUUUUUUUUUUUUUUUUUUUUUGACCGUCUCAAGGUCCAA-
GUUAGUCUGCCUAUAAAGGUGCGGAUCCACAGCUGAUGAAAGACUUGUG-

-continued

CGGUACGGUUAAUCUCCCCUUUUUUUUUUUUUUUUUUUUUUUAGU-

AAAUGCGUCUACUGAAUCCAGCGAUGAUGCUGGCCCAGAUC (R 722 SEQ ID NO: 379)

GGGAGAAAGCUCAAGCUUAUCCAAGUAGGCUGGUCACCUGUACAAC-

GUAGCCGGUAUUUUUUUUUUUUUUUUUUUUUUUUGACCGUCUCAAGGUCCAA-

GUUAGUCUGCCUAUAAAGGUGCGGAUCCACAGCUGAUGAAAGACUUGUG-

CGGUACGGUUAAUCUCCCCUUUUUUUUUUUUUUUUUUUUUUUAGU-

AAAUGCGUCUACUGAAUCCAGCGAUGAUGCUGGCCCAGAUCUUCGACCACAA-

GUGCAUAUAGUAGUCAU-

CGAGGGUCGCCUUUUUUUUUUUUUUUUUUUUUUUUUGGCCCAGUUCUGAGACU-

UCGCUAGAGACUACAGUUACAGCUGCAGUAGUAACCACUGCGGCUAUUGCAG-

GAAAUCCCGUUCAGGUUUUUUUUUUUUUUUUUUUUUUUCCGCUCACUAUGAU-

UAAGAACCAGGUGGAGUGUCACUGCUCUCGAGGUCUCACGA-

GAGCGCUCGAUACAGUCCUUGGAA-

GAAUCUUUUUUUUUUUUUUUUUUUUUUUGUGCGACGAUCACAGAGAACU-

UCUAUUCAUGCAGGUCUGCUCUA (SEQ ID NO: 380)

GGGAGAAAGCUCAAGCUUAUCCAAGUAGGCUGGUCACCUGUACAAC-

GUAGCCGGUAUUUUUUUUUUUUUUUUUUUUUUUUGACCGUCUCAAGGUCCAA-

GUUAGUCUGCCUAUAAAGGUGCGGAUCCACAGCUGAUGAAAGACUUGUG-

CGGUACGGUUAAUCUCCCCUUUUUUUUUUUUUUUUUUUUUUUAGU-

AAAUGCGUCUACUGAAUCCAGCGAUGAUGCUGGCCCAGAUCUUCGACCACAA-

GUGCAUAUAGUAGUCAU-

CGAGGGUCGCCUUUUUUUUUUUUUUUUUUUUUUUUUGGCCCAGUUCUGAGACU-

UCGCUAGAGACUACAGUUACAGCUGCAGUAGUAACCACUGCGGCUAUUGCAG-

GAAAUCCCGUUCAGGUUUUUUUUUUUUUUUUUUUUUUUCCGCUCACUAUGAU-

UAAGAACCAGGUGGAGUGUCACUGCUCUCGAGGUCUCACGA-

GAGCGCUCGAUACAGUCCUUGGAA-

GAAUCUUUUUUUUUUUUUUUUUUUUUUUGUGCGACGAUCACAGAGAACU-

UCUAUUCAUGCAGGUCUGCUCUAGAACGAACUGACCUGACGCCUGAACU-

UAUGAGCGUGCGUAUUUUUUUUUUUUUUUUUUUUUUUUUCCUCCCAACAAAU-

GUCGAUCAAUAGCUGGGCUGUUGGAGACGCGUCAGCAAAUGCCGUG-

GCUCCAUAGGACGUGUAGACUUCUAUUUUUUUUUUUUUUUUUUUUUUUCCCGG-

GACCACAAAUAAUAUUCUUGCUUGGUUGGGCG-

CAAGGGCCCCGUAUCAGGUCAUAAACGGGUACAUGUUG-

CACAGGCUCCUUUUUUUUUUUUUUUUUUUUUUUUUCGCUGAGUUAUUCCGGUCUCA

AAAGACGGCAGACGUCAGUCGACAACACGGUCUAAAGCAGUG-

CUACAAUCUGCCGUGUUCGUGUUUUUUUUUUUUUUUUUUUUUUGUGAACCUACAC-

GGCGUGCACUGUAGUUCGCAAU-

UCAUAGGGUACCGGCUCAGAGUUAUGCCUUGGUUGAAAACUGCCCAGCAUACU-

-continued

UUUUUUUUUUUUUUUUUUUCAUAUUCCCAUGCU-

AAGCAAGGGAUGCCGCGAGUCAUGUUAAGCUUGAAUU

According to another very particularly preferred embodiment, the nucleic acid molecule according to formula (V) may be selected from e.g. any of the following sequences:

(SEQ ID NO: 381)
UAGCGAAGCUCUUGGACCUACCUUUUUUUUUUUUUUCCCUGCGUUCCUA
GAA-GUACACG
or (SEQ ID NO: 382)
UAGCGAAGCUCUUGGACCUACCUUUUUUUUUUUUUUUCCCUGCGUUCCU
AGAA-GUACACGAUCGCUUCGAGAACCUGGAUGGAAAAAAAAAAAAAAA
GGGAC-GCAAGGAUCUUCAUGUGC or from a sequence having at least 60%, 70%, 80%, 90%, or even 95% sequence identity with any of these sequences.

Finally, the so called "(adjuvant) component", which may be used to together with the mRNA in the inventive vaccine, is preferably prepared according to a first step by complexing the at least one (m)RNA of the (adjuvant) component with a cationic or polycationic compound and/or with a polymeric carrier, preferably as defined herein, in a specific ratio to form a stable complex. In this context, it is highly preferable, that no free cationic or polycationic compound or polymeric carrier or only a neglectably small amount thereof remains in the (adjuvant) component after complexing the (m)RNA. Accordingly, the ratio of the (m)RNA and the cationic or polycationic compound and/or the polymeric carrier in the (adjuvant) component is typically selected in a range that the (m)RNA is entirely complexed and no free cationic or polycationic compound or polymeric carrier or only a neglectably small amount thereof remains in the composition. Preferably the ratio of the (adjuvant) component, i.e. the ratio of the (m)RNA to the cationic or polycationic compound and/or the polymeric carrier, preferably as defined herein, is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w). Alternatively, the ratio of the (m)RNA to the cationic or polycationic compound and/or the polymeric carrier, preferably as defined herein, in the (adjuvant) component, may also be calculated on the basis of the nitrogen/phosphate ratio (N/P-ratio) of the entire complex of the (adjuvant) component. In the context of the present invention, an N/P-ratio is preferably in the range of about 0.1-10, preferably in a range of about 0.3-4 and most preferably in a range of about 0.5-2 or 0.7-2 regarding the ratio of (m)RNA:cationic or polycationic compound and/or polymeric carrier, preferably as defined herein, in the complex, and most preferably in the range of about 0.7-1.5, preferably provided the cationic or polycationic compound in the complex is a cationic or polycationic cationic or polycationic protein or peptide and/or the polymeric carrier is as defined above. Such ratios, particularly weight and/or N/P ratios may also be applied to ratios of the at least one mRNA encoding at least one antigen as defined herein to a cationic or polycationic polymer or a polymeric carrier as defined herein used to complex the at least one mRNA.

According to a further preferred aspect, the mRNA of the inventive vaccine encoding at least one antigen as defined above may be formulated together with an (adjuvant) component as defined above, wherein the inventive vaccine may comprise a) an (adjuvant) component, comprising or consisting of at least one (m)RNA, complexed with a cationic or polycationic compound and/or with a polymeric carrier, preferably as defined herein, and b) at least one free mRNA, encoding an antigen, preferably as defined herein. This formulation is preferably as defined above. Furthermore, the entire formulation of a) and b) may be additionally packaged with a carrier molecule to allow combined packaging the (adjuvant) component and the antigen. Such a carrier molecule may be selected from any polymer suitable for packaging and preferably transporting the entire formulation of a) and b) into cells, tissue, etc., of a patient as defined herein, e.g. from a cationic or polycationic polymer as defined herein or from any further polymer suitable for this purpose, e.g. a polymeric carrier as defined above.

The ratio of all components of the entire inventive vaccine composition, as defined above, preferably, an adjuvant component comprising or consisting of at least one immunostimulatory nucleic acid sequence, complexed with a cationic or polycationic compound, the at least one mRNA encoding at least one antigen, and/or a carrier molecule, formulated in the inventive vaccine, may be calculated on the basis of the nitrogen/phosphate ratio (N/P-ratio) of all these components. In the context of the present invention, an N/P-ratio is preferably in the range of about 0.01-4, 0.01-2, 0.1-2 or 0.1-1.5 regarding the ratio of nucleic acids:cationic or polycationic peptide contained in the inventive vaccine, and most preferably in the range of about 0.1-1. Such an N/P ratio is preferably designed to provide good transfection properties in vivo and transport into and through cell membranes. Preferably, for this purpose, cationic or polycationic compound and/or polymeric carriers as used herein, are based on peptide sequences.

In a further preferred aspect of the present invention the inventive vaccine may comprise a pharmaceutically acceptable carrier and/or vehicle. In the context of the present invention, a pharmaceutically acceptable carrier typically includes the liquid or non-liquid basis of a composition comprising the components of the inventive vaccine. If the composition is provided in liquid form, the carrier will typically be pyrogen-free water; isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds, which are suitable for administration to a patient to be treated, may be used as well for the inventive vaccine. The term "compatible" as used here means that these constituents of the inventive vaccine are capable of being mixed with the components of the inventive vaccine in such a manner that no interaction occurs which would substantially reduce the pharmaceutical effectiveness of the inventive vaccine under typical use conditions.

According to a specific aspect, the inventive vaccine may comprise an adjuvant. In this context, an adjuvant may be understood as any compound, which is suitable to initiate or increase an immune response of the innate immune system, i.e. a non-specific immune response. With other words, when administered, the vaccine preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

According to one aspect such an adjuvant may be selected from an (adjuvant) component as defined above.

According to one further aspect such an adjuvant may be selected from any adjuvant known to a skilled person and suitable for the present case, i.e. supporting the induction of an innate immune response in a mammal and/or suitable for depot and delivery of the components of the inventive vaccine. Preferred as adjuvants suitable for depot and delivery are cationic or polycationic compounds as defined above. Likewise, the adjuvant may be selected from the group consisting of, without being limited thereto, cationic or polycationic compounds as defined above, from chitosan, TDM, MDP, muramyl dipeptide, pluronics, alum solution, aluminium hydroxide, AD-JUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylaminob-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D35 glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L47 alanyl-D-isoglutamine); imiquimod (1-(2-methypropyl)-1H-imidazo[4,5-c]quinoline-4-amine); ImmTher™ (N-acetyl-glucosaminylN-acetylmuramyl-L-Ala-D-isoGlu-L-Ala-glycerol dipalmitate); DRVs (immunoliposomes prepared from dehydration-rehydration vesicles); interferongamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT 5 oral adjuvant (*E. coli* labile enterotoxin-protoxin); microspheres and microparticles of any composition; MF59™; (squalenewater emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-AlaD-Gln-OCH3); MURAPALMITINE™ and DMURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (□-glucan); PLGA, PGA and PLA (homo- and co-polymers of lactic acid and glycolic acid; microspheres/nanospheres); PLURONIC L121™; PMMA (polymethylmethacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, AL); STIMULON™ (QS-21); Quil-A (Quil-A saponin); S-28463 (4-amino-otec-dimethyl-2-ethoxymethyl-1H-imidazo[4,5-c]quinoline-1-ethanol); SAF-1™ ("Syntex adjuvant formulation"); Sendai proteoliposomes and Sendaicontaining lipid matrices; Span85 (sorbitan trioleate); Specol (emulsion of Marcol 52, Span 85 and Tween 85); squalene or ROBANE® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); THERAMID® (N-acetylglucosaminyl-N-acetylmuramyl-L-Ala-D-isoGlu-LAladipalmitoxypropylamide); Theronyl-MDP (Termurtide™ or [thr 1]-MDP; N-acetylmuramyl-Lthreonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin, microbe derived adjuvants, including Romurtide, DETOX, MPL, CWS, Mannose, CpG nucleic acid sequences, CpG7909, ligands of human TLR 1-10, ligands of murine TLR 1-13, ISS-1018, 35 IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Particularly preferred, an adjuvant may be selected from adjuvants, which support induction of a Th1-immune response or maturation of naïve T cells, such as GM-CSF, IL-12, IFNγ, immunostimulatory RNA sequences as defined herein, CpG DNA, etc.

The inventive vaccine may additionally contain a further immunotherapeutic agent selected from immunoglobulins, preferably IgGs, monoclonal or polyclonal antibodies, polyclonal serum or sera, etc. Preferably, such a further immunotherapeutic agent may be provided as a peptide/protein or may be encoded by a nucleic acid, preferably by a DNA or an RNA, more preferably an mRNA. Such an immunostimulatory agent allows providing passive vaccination additional to active vaccination triggered by the mRNA encoded antigen of the inventive composition or vaccine composition.

The inventive vaccine can additionally contain one or more auxiliary substances in order to increase its immunogenicity or immunostimulatory capacity, if desired. A synergistic action of the inventive vaccine and of an auxiliary substance, which may be optionally contained in the vaccine or may be formulated with the inhibitor, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a “danger signal” (LPS, GP96, etc.) or cytokines, such as GM-CFS, which allow an immune response to be enhanced and/or influenced in a targeted manner.

Particularly preferred auxiliary substances are cytokines, such as monokines, lymphokines, interleukins or chemokines, that further promote the innate immune response, such as IL-1, IL-2, IL3, IL-4, IL-5, IL-6, IL-7, IL-8, IL-9, IL-10, IL-12, IL-13, IL-14, IL-15, IL-16, IL-17, IL-18, IL19, IL-20, IL-21, IL-22, IL-23, IL-24, IL-25, IL-26, IL-27, IL-28, IL-29, IL-30, IL-31, IL-32, IL33, IFNα, IFNβ, IFNγ, GM-CSF, G-CSF, M-CSF, LT-beta or TNF-alpha, growth factors, such as hGH.

The inventive vaccine can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13, a ligand of a NOD-like receptor, or a ligand of a RIG-I like receptor.

In this context the inventive vaccine may also additionally contain an immunostimulatory nucleic acid, preferably an immunostimulatory RNA (isRNA), as defined above.

The inventive vaccine as defined according to the first embodiment of the present invention may furthermore comprise further additives or additional compounds. Further additives which may be included in the inventive vaccine are emulsifiers, such as, for example, TWEEN®; wetting agents, such as, for example, sodium lauryl sulfate; colouring agents; taste-imparting agents, pharmaceutical carriers; tablet-forming agents; stabilizers; antioxidants; preservatives.

One further additive, which may be contained in the inventive vaccine, may be an antibacterial agent. In this context, any anti-bacterial agents known to one of skill in the art may be used in combination with the components of the inventive vaccine as defined herein. Non-limiting examples of anti-bacterial agents include Amikacin, Amoxicillin, Amoxicillin-clavulanic acid, Amphothericin-B, Ampicillin, Ampicllin-sulbactam, Apramycin, Azithromycin, Aztreonam, Bacitracin, Benzylpenicillin, Caspofungin, Cefaclor, Cefadroxil, Cefalexin, Cefalothin, Cefazolin, Cefdinir, Cefepime, Cefixime, Cefmenoxime, Cefoperazone, Cefoperazonesulbactam, Cefotaxime, Cefoxitin, Cefbirome, Cefpodoxime, Cefpodoxime-clavulanic acid, Cefpodoxime-sulbactam, Cefbrozil, Cefquinome, Ceftazidime, Ceftibutin, Ceftiofur, Ceftobiprole, Ceftriaxon, Cefuroxime, Chloramphenicole, Florfenicole, Ciprofloxacin, Clarithromycin, Clinafloxacin, Clindamycin, Cloxacillin, Colistin, Cotrimoxazol (Trimthoprim/sulphamethoxazole), Dalbavancin, Dalfopristin/Quinopristin, Daptomycin, Dibekacin, Dicloxacillin, Doripenem, Doxycycline, Enrofloxacin, Ertapenem, Erythromycin, Flucloxacillin, Fluconazol, Flucytosin, Fosfomycin, Fusidic acid, Garenoxacin, Gatifloxacin, Gemifloxacin, Gentamicin, Imipenem, Itraconazole, Kanamycin, Ketoconazole, Levofloxacin, Lincomycin, Linezolid, Loracarbef, Mecillnam (amdinocillin), Meropenem, Metronidazole, Meziocillin, Mezlocillin-sulbactam, Minocycline, Moxifloxacin, Mupirocin, Nalidixic acid, Neomycin, Netilmicin, Nitrofurantoin, Norfloxacin, Ofloxacin, Oxacillin, Pefloxacin, Penicillin V, Piperacillin, Piperacillin-sulbactam, Piperacillin-tazobactam, Rifampicin, Roxythromycin, Sparfloxacin, Spectinomycin, Spiramycin, Streptomycin, Sulbactam, Sulfamethoxazole, Teicoplanin, Telavancin, Telithromycin, Temocillin, Tetracyklin, Ticarcillin, Ticarcillin-clavulanic acid, Tigecycline, Tobramycin, Trimethoprim, Trovafloxacin, Tylosin, Vancomycin, Virginiamycin, and Voriconazole.

Another additive, which may be contained in the inventive vaccine, may be an anti-viral agents, preferably, but are not limited to, nucleoside analogs (e.g., zidovudine, acyclovir, gangcyclovir, vidarabine, idoxuridine, trifluridine, and ribavirin), foscarnet, amantadine, peramivir, rimantadine, saquinavir, indinavir, ritonavir, alpha-interferons and other interferons, AZT, t-705, zanamivir (RELENZA®), and oseltamivir (TAMIFLU®). Other anti-viral agents include influenza virus vaccines, e.g., FLUARIX® (Glaxo SmithKline), FLUMIST® (Medlmmune Vaccines), FLUVIRIN® (Chiron Corporation), FLULAVAL® (GlaxoSmithKline), AFLURIA® (CSL Biotherapies Inc.), AGRIFLU® (Novartis) or FLUZONE® (Aventis Pasteur).

The inventive vaccine typically comprises a “safe and effective amount” of the components of the inventive vaccine as defined herein. As used herein, a “safe and effective amount” preferably means an amount of the components, preferably of the at least one mRNA, that is sufficient to significantly induce a positive modification of a disease or disorder as defined herein. At the same time, however, a “safe and effective amount” is small enough to avoid serious side-effects and to permit a sensible relationship between advantage and risk. The determination of these limits typically lies within the scope of sensible medical judgment.

As defined according to the first embodiment, the inventive vaccine comprising at least one mRNA encoding at least one antigen may be used in the prophylaxis and treatment of a disease in newborns and/or infants, preferably exhibiting an age of not more than 3 or 2 years, preferably of not more than 1 year (12 months), more preferably of not more than 9, 6 or 3 months. The treatment preferably comprises vaccination of the newborn or infant and eliciting an immune response in said newborn or infant. Preferably, a newborn or infant is a mammal (patient), preferably a human (patient), typically exhibiting an age of not more than 3 or usually 2 years, preferably of not more than 1.5 years, more preferably of not more than 1 year (12 months), even more preferably of not more than 9 months, 6 months or even 3 months. Accordingly, a newborn or infant may comprise an age of about 0 to 3 or usually 0 to 2 years, preferably of 0 to 1.5 years, more preferably of 0 to 1 years (0 to 12 months), even more preferably of not more than 0 to 9 months, 0 to 6 months or even 0 to 3 months. A newborn or infant may furthermore be distinguished into a newborn, typically exhibiting an age of not more than 1 year (12 months), preferably of not more than 9 months, 6 months or even 3 months. Accordingly, a newborn or infant may comprise an age of about 0 to 1 years (0 to 12 months), preferably of not more than 0 to 9 months, 0 to 6 months or even 0 to 3 months. A newborn or infant may furthermore be distinguished into an infant, typically exhibiting an age of more than 3 months, preferably exhibiting an age of 6 months, more preferably exhibiting an age of more than 9 months, but additionally exhibiting an age of not more than 3 or usually 2 years, preferably of not more than 1.5 years, more preferably of not more than 1 year (12 months), even more preferably of not more than 9 months or even 6 months. Accordingly, a newborn or infant may comprise an age of about 3 months to about 3 years, about 3 months to about 2 years, about 3 months to about 1.5 years, or about 3 months to about 1 year (12 months), about 6 months to about 3 years, about 6 months to about 2 years, about 6 months to about 1.5 years, or about 6 months to about 1 year (12 months), about 9 months to about 3 years, about 9 months to about 2 years, or about 9 months to about 1.5 years, about 12 months to about 3 years, about 12 months to about 2 years, or about 12 months to about 1.5 years. The newborns and or infant may be male or female.

As furthermore defined in the first embodiment of the present invention, the treatment comprises vaccination of the patient and eliciting an immune response in said patient. In this context, vaccination typically occurs via administration of the inventive vaccine. Administration may occur parenterally, orally, nasally, pulmonary, by inhalation (e.g. via an aerosol or spray), topically, rectally, buccally, vaginally, or via an implanted reservoir. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. Preferably, the inventive vaccine may be administered intradermally to reach APCs in the dermis. Likewise preferably, the inventive vaccine as defined herein may be administered orally in any orally acceptable dosage form including, but not limited to, capsules, tablets, aqueous suspensions or solutions. Likewise preferably, the inventive vaccine may be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive vaccine may be formulated in a suitable ointment, containing the inventive vaccine and optionally further components as defined herein suspended or dissolved in one or more carriers. Pulmonary administration can also be employed, e.g., by use of an inhaler or nebulizer, and formulation with an aerosolizing agent for use as a spray.

The inventive vaccine may be used in combination with other therapies, preferably with a therapy for a disease as defined herein, or further therapies. As used herein, the term "in combination," in the context of the administration of two or more therapies to a newborn or an infant as defined herein, refers to the use of more than one therapy, preferably two therapies or even more. The use of the term "in combination" does not restrict the order in which therapies are administered to a newborn or an infant as defined herein. For example, a first therapy (e.g., a first prophylactic or therapeutic agent) can be administered at any time prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a newborn or an infant as defined herein. In some aspects, the one or more other therapies are surgery, immunotherapies, gene therapies, pain treatments, anti-fever medications, therapies that alleviate or assist with breathing, other (active or passive) vaccinations/immunizations, anti-viral therapies, antibacterial therapies, antifungal therapies, anti-parasite therapies, anti-allergic therapies, conventional tumour therapies, chemotherapies, or may include a post exposition prophylaxis in or for any of the diseases mentioned herein, preferably for rabies, RSV viral infection, etc.

In certain aspects, the therapies are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours apart. In specific aspects, two or more therapies are administered within the same patient visit.

Exemplary doses for mRNAs encoding at least one antigen as defined herein may range, without being limited thereto, from about 10 ng to 1 g, 100 ng to 100 mg, 1 μg to 10 μg, or 30-300 μg mRNA per patient. Preferably, the inventive vaccine is formulated accordingly to comprise one dose, two doses, three or even more doses.

According to a specific aspect, the inventive vaccine may be administered to a newborn or an infant as a single dose. In certain aspects, the inventive vaccine may be administered to a newborn or an infant as a single dose followed by a second dose later and optionally even a third, fourth (or more) dose subsequent thereto etc. In accordance with this aspect, booster inoculations with the inventive vaccine may be administered to a newborn or an infant at specific time intervals, preferably as defined below, following the second (or third, fourth, etc.) inoculation. In certain aspects, such booster inoculations with the inventive vaccine may utilize an additional compound or component as defined for the inventive vaccine as defined herein. In some aspects, the administration of the same inventive vaccine and/or booster administrations may be repeated and such administrations may be separated by at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, 12 months, 18 months, 24 months, 30 months, 36 months, 1 year, 2 years, 3 years, 5 years, 10 years, 15 years, 20 years, 30 years, 40 years, 50 years, 60 years, or even more. In certain aspects, the inventive vaccine may be administered to a subject as a single dose once per year.

In particular aspects, the inventive vaccine may be administered to a newborn or an infant in the fall or winter, i.e., prior to or during the influenza season in each hemisphere. In one aspect, a newborn or an infant is administered his/her first dose early in the season, e.g., late September or early October, so that the second dose (if necessary) can be given prior to the peak of the influenza season.

In particular aspects, the inventive vaccine may be administered at least once, preferably twice or more to a newborn or an infant prior to a treatment of a disease as defined herein, preferably at least 1 day, 2 days, 3 days, 4 days, 5 days, 10 days, 15 days, 30 days, 45 days, 2 months, 75 days, e.g. 1 to 5 days, 1 to 10 days, 5 to 15 days, 10 to 20 days, 15 to 25 days, 20 to 30 days, 25 to 35 days, 30 to 50 days, 40 to 60 days, 50 to 70 days, 1 to 75 days, or 1 month, 2 months, 3 months, 4 months, 5 months, or at least 6, 7, 8, 9, 10, 11, or 12 months prior to a treatment of a disease as defined herein. A second or further dose may then be administered directly prior to treatment, concurrent with or subsequent to treatment.

Furthermore, a disease as defined according to the first embodiment of the present invention is any disease selected from infectious diseases, preferably (viral, bacterial or protozoological) infectious diseases, autoimmune diseases, allergies or allergic diseases or cancer or tumour diseases diseases.

Such diseases include cancer or tumour diseases, preferably selected from melanomas, malignant melanomas, colon carcinomas, lymphomas, sarcomas, blastomas, renal carcinomas, gastrointestinal tumours, gliomas, prostate tumours, bladder cancer, rectal tumours, stomach cancer, oesophageal cancer, pancreatic cancer, liver cancer, mammary carcinomas (=breast cancer), uterine cancer, cervical cancer, acute myeloid leukaemia (AML), acute lymphoid leukaemia (ALL), chronic myeloid leukaemia (CML), chronic lymphocytic leukaemia (CLL), leukaemia, hepatomas, various virus-induced tumours such as, for example, papilloma virus-induced carcinomas (e.g. cervical carcinoma=cervical cancer), adenocarcinomas, herpes virus-induced tumours (e.g. Burkitt's lymphoma, EBV-induced B cell lymphoma), heptatitis B-induced tumours (hepatocell carcinomas), HTLV-1- and HTLV-2-induced lymphomas, acoustic neuroma, lung carcinomas (=lung cancer=bronchial carcinoma), small-cell lung carcinomas, pharyngeal cancer, anal carcinoma, glioblastoma, rectal carcinoma, astrocytoma, brain tumours, retinoblastoma, basalioma, brain metastases, medulloblastomas, vaginal cancer, pancreatic cancer, testicular cancer, Hodgkin's syndrome, meningiomas, Schneeberger disease, hypophysis tumour, Mycosis fungoides, carcinoids, neurinoma, spinalioma, Burkitt's lymphoma, laryngeal cancer, renal cancer, thymoma, corpus carcinoma, bone cancer, non-Hodgkin's lymphomas, urethral cancer, CUP syndrome, head/neck tumours, oligodendroglioma, vulval cancer, intestinal cancer, colon carcinoma, oesophageal carcinoma (=oesophageal cancer), wart involvement, tumours of the small intestine, craniopharyngeomas, ovarian carcinoma, genital tumours, ovarian cancer (=ovarian carcinoma), pancreatic carcinoma (=pancreatic cancer), endometrial carcinoma, liver metastases, penile cancer, tongue cancer, gall bladder cancer, leukaemia, plasmocytoma, lid tumour, prostate cancer (=prostate tumours), etc.

According to one further specific aspect, diseases as defined herein comprise infectious diseases, preferably (viral, bacterial or protozoological) infectious diseases. Such infectious diseases, preferably viral, bacterial or protozoological infectious diseases, are typically selected from viral infectious diseases such as influenza, preferably influenza-A, influenza-B, influenza-C or thogotovirus, more preferably influenza-A comprising e.g. haemagglutinin subtypes H1, H2, H3, H4, H5, H6, H7, H8, H9, H10, H11, H12, H13, H14 or H15, and/or neuroamidase subtypes N1, N2, N3, N4, N5, N6, N7, N8 or N9, or preferably influenza-A subtypes H1N1, H1N2, H2N2, H2N3, H3N1, H3N2, H3N3, H5N1, H5N2, H7N7 or H9N2, etc., or any further combination, malaria, severe acute respiratory syndrome (SARS), respiratory syncytial virus infection, yellow fever, AIDS, Lyme borreliosis, Leishmaniasis, anthrax, meningitis, Condyloma *acuminata*, hollow warts, Dengue fever, three-day fever, Ebola virus, cold, early summer meningoencephalitis (FSME), shingles, hepatitis, herpes simplex type I, herpes simplex type II, Herpes zoster, Japanese encephalitis, Arenavirus-associated diseases (Lassa fever infection), Marburg virus, measles, foot-and-mouth disease, mononucleosis infectiosa (Pfeiffer's glandular fever), mumps, Norwalk virus infection, smallpox, polio (childhood lameness), pseudo-croup, Erythema infectiosum (fifth disease), rabies, warts, West Nile fever, chickenpox, cytomegalic virus (CMV), bacterial infectious diseases such as miscarriage (prostate inflammation), anthrax, appendicitis, borreliosis, botulism, *Campylobacter, Chlamydia trachomatis* (inflammation of the urethra, conjunctivitis), cholera, diphtheria, donavanosis, epiglottitis, typhus fever, gas gangrene, gonorrhoea, rabbit fever, *Helicobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella* paratyphus, *Salmonella* typhus, scarlet fever, syphilis, tetanus, tripper, tsutsugamushi disease, tuberculosis, typhus, vaginitis (colpitis), soft chancre, and infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm.

According to another specific aspect, diseases as defined herein comprise autoimmune diseases as defined in the following. Autoimmune diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T cell bypass. A normal immune system requires the activation of B cells by T cells before the former can produce antibodies in large quantities. This requirement of a T cell can be by-passed in rare instances, such as infection by organisms producing super-antigens, which are capable of initiating polyclonal activation of B cells, or even of T cells, by directly binding to the B-subunit of T cell receptors in a non-specific fashion. Another explanation deduces autoimmune diseases from a "Molecular Mimicry": an exogenous antigen may share structural similarities with certain host antigens; thus, any antibody produced against this antigen (which mimics the self-antigens) can also, in theory, bind to the host antigens and amplify the immune response. Autoimmune diseases based on molecular mimicry are known to a skilled person for various viral and bacterial antigens. The most striking form of molecular mimicry is observed in Group A beta-haemolytic streptococci, which shares antigens with human myocardium, and is responsible for the cardiac manifestations of rheumatic fever.

Additionally, according to one further specific aspect, diseases as defined herein comprise allergies or allergic diseases, i.e. diseases related to allergies. Allergy is a condition that typically involves an abnormal, acquired immunological hypersensitivity to certain foreign antigens or allergens, such as the allergy antigens as defined herein. Such allergy antigens or allergens may be selected from allergy antigens as defined herein antigens derived from different sources, e.g. from animals, plants, fungi, bacteria, etc. Allergens in this context include e.g. danders, grasses, pollens, molds, drugs, or numerous environmental triggers, etc. Allergies normally result in a local or systemic inflammatory response to these antigens or allergens and lead to immunity in the body against these allergens. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, asthma, allergic asthma (leading to swelling of the nasal mucosa), allergic conjunctivitis (leading to redness and itching of the conjunctiva), allergic rhinitis ("hay fever"), anaphylaxis, angiodema, atopy, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. Treatment of such allergic disorders or diseases may occur preferably by desensitizing the immune reaction which triggers a specific immune response. Such a desensitizing may be carried out by administering an effective amount of the allergen or allergic antigen encoded by the nucleic acid as defined herein, preferably, when formulated as a pharmaceutical composition, to induce a slight immune reaction. The amount of the allergen or allergic antigen may then be raised step by step in subsequent administrations until the immune system of the patient to be treated tolerates a specific amount of allergen or allergic antigen.

Diseases in the context of the present invention may also include type II hypersensitivity reactions (cytotoxic, antibody-dependent), including e.g. autoimmune hemolytic anemia, thrombocytopenia, erythroblastosis fetalis, Goodpasture's syndrome, Graves' disease, Myasthenia Gravis, etc.; type III hypersensitivity reactions (immune complex disease), including e.g. serum sickness, Arthus reaction, Systemic lupus erythematosus (SLE), etc.; type IV hypersensitivity reactions (delayed-type hypersensitivity (DTH), cell-mediated immune memory response, antibody-independent), including e.g. contact dermatitis, Mantoux test, chronic transplant rejection, multiple sclerosis, etc.; and type V hypersensitivity reactions (receptor mediated autoimmune disease), including e.g. Graves' disease, Myasthenia Gravis, etc.;

In a further preferred embodiment, the inventive vaccine may be formulated as a kit, preferably as a kit of part. Accordingly, the present invention also provides kits, particularly kits of parts, comprising the components of the inventive vaccine either alone or in combination with further ingredients as defined above, and optionally technical instructions with information on the administration and dosage of the inventive vaccine. The components of the inventive vaccine either alone or in combination with further ingredients as defined above may be contained in the kit in either one part of the kit or in different parts of the kit, e.g. each at least one mRNA encoding at least one antigen as defined above in one part of the kit, and preferably further components admixed to the each at least one mRNA encoding at least one antigen or separately in a further part of the kit. Such kits, preferably kits of parts, may be applied, e.g., for any of the above mentioned applications or uses.

In the present invention, if not otherwise indicated, different features of alternatives and embodiments may be combined with each other, where suitable. Furthermore, the term "comprising" shall not be construed as meaning "consisting of", if not specifically mentioned. However, in the context of the present invention, term "comprising" may be substituted with the term "consisting of", where suitable.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

FIGURES

The following Figures are intended to illustrate the invention further. They are not intended to limit the subject matter of the invention thereto.

FIG. 1A: shows the development of the weight of the mice in the experiment. As a result newborn mice vaccinated with mRNA coding for PR8 H1 Hemagglutinin exhibited a significantly better survival (all mice survived) against influenza challenge infection with control mRNA only (all mice died about 5 days subsequent to vaccination with control mRNA encoding chicken ovalbumin, when vaccinated with control mRNA at the first day 8 weeks and died about 6 days subsequent to vaccination with control mRNA, when vaccinated with 8 weeks). Most surprisingly, the survival rate was comparable to that of adult mice.

FIGS. 1B, 1C show the coding sequence of the mRNAs used for vaccination of newborn and 8 weeks old mice (see FIG. 1A) coding for PR8 H1 HA (Hemagglutinin of influenza virus A/Puerto Rico/8/1934) (SEQ ID NO: 384) (FIG. 1B) or for *Gallus gallus* ovalbumine as a control (control mRNA) (SEQ ID NO: 385) (FIG. 1C)

EXAMPLES

The following examples are intended to illustrate the invention further. They are not intended to limit the subject matter of the invention thereto.

Example 1—Preparation of mRNA Constructs

For the present examples DNA sequences, encoding PR8 H1 HA (Haemagglutinin of A/Puerto Rico/8/1934) (SEQ ID NO: 384), and *Gallus gallus* ovalbumine, respectively, as a control (control mRNA) (SEQ ID NO: 385), were prepared and used for subsequent in vitro transcription reactions.

According to a first preparation, the DNA sequence termed PR8 H1 HA (Haemagglutinin of A/Puerto Rico/8/1934) (SEQ ID NO: 384) (see FIG. 1B) was prepared by modifying the wildtype Haemagglutinin encoding DNA sequence by introducing a GC-optimized sequence for a better codon usage and stabilization. In SEQ ID NO: 384 (see FIG. 1B) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70× adenosine at the 3'-terminal end (poly-A-tail) and a stretch of 30× cytosine at the 3'-terminal end (poly-C-tail). The sequence of the final DNA construct was termed "PR8 H1 HA".

According to a second preparation, the DNA sequence termed *Gallus gallus* ovalbumine, respectively, as a control (control mRNA) (SEQ ID NO: 385) (see FIG. 1C) was prepared by modifying the wildtype *Gallus gallus* ovalbumine encoding DNA sequence by introducing a GC-optimized sequence for a better codon usage and stabilization. In SEQ ID NO: 385 (see FIG. 1C) the sequence of the corresponding mRNA is shown. The sequence was furthermore introduced into a pCV19 vector and modified to comprise stabilizing sequences derived from alpha-globin-3'-UTR (muag (mutated alpha-globin-3'-UTR)), a stretch of 70× adenosine at the 3'-terminal end (poly-A-tail) and a stretch of 30× cytosine at the 3'-terminal end (poly-C-tail). The sequence of the final DNA construct was termed "*Gallus gallus* ovalbumine".

In a further step, the respective DNA plasmids prepared above were transcribed into mRNA in vitro using T7-Polymerase. Subsequently the obtained mRNA was purified using PUREMESSENGER® (CureVac, Tubingen, Germany).

All obtained mRNAs used herein were furthermore complexed with protamine prior to use. The RNA complexation consisted of a mixture of 50% free mRNA and 50% mRNA complexed with protamine at a weight ratio of 2:1. First, mRNA was complexed with protamine by slow addition of protamine-Ringer's lactate solution to mRNA. As soon as the complexes were stably generated, free mRNA was added, stirred shortly and the final concentration of the vaccine was adjusted with Ringer's lactate solution.

Example 2—Vaccination of Newborn and 8 Weeks Old Mice

In this experiment newborn or 8 weeks old mice were vaccinated twice intradermally with 80 μg mRNA coding for PR8 H1 HA (Hemagglutinin of A/Puerto Rico/8/1934; FIG. 1B) or with mRNA coding for *Gallus gallus* ovalbumine as a control (control mRNA; FIG. 1C). The first injection was carried out at the first day of life (≤24 h) and with 8 weeks, respectively. 5 weeks after the last vaccination the mice were challenged with a 10fold median lethal dose of PR8 virus (10 LD50). The weight of the mice was controlled over 2 weeks and the mice were killed when they have lost more than 25% of their original weight. The results are shown in FIG. 1A. FIG. 1A shows the development of the weight of the mice in the experiment. As a result mice vaccinated with mRNA coding for PR8 H1 Hemagglutinin exhibited a significantly better survival (all mice survived) against influenza challenge infection with control mRNA only (all mice in the control experiment died about 5 days subsequent to vaccination with control mRNA encoding chicken ovalbumin, when vaccinated with control mRNA at the first day and died about 6 days subsequent to vaccination with control mRNA, when vaccinated with 8 weeks). All vaccinated newborn mice survived antigen challenge with PR8 H1 Hemagglutinin in contrast to the control.

The invention claimed is:

1. A method for stimulating a protective antigen specific immune response in a subject comprising, administering to the subject an effective amount of a composition comprising a purified mRNA encoding a respiratory syncytial virus (RSV) fusion protein, or an antigenic fragment thereof, said mRNA comprising a 5' cap and a poly-A sequence, wherein said mRNA is complexed with a cationic or polycationic compound, wherein the composition is administered by injection and wherein the subject is no more than 2 years of age.

2. The method of claim 1, wherein the subject is about 3 months to 2 years of age.

3. The method of claim 2, wherein the subject is no more than 1 year of age.

4. The method of claim 3, wherein the subject is no more than 6 months of age.

5. The method of claim 1, wherein the composition is administered by intradermal or intramuscular injection.

6. The method of claim 5, wherein the composition is administered by intramuscular injection.

7. The method of claim 5, wherein the cationic or polycationic compound comprises a cationic lipid.

8. The method of claim 5, wherein the mRNA comprises a backbone modification, a sugar modification, or a base modification.

9. The method of claim 8, wherein the mRNA comprises a base modification.

10. The method of claim 5, wherein the composition further comprises an adjuvant.

11. The method of claim 5, wherein the antigen-specific immune response comprises production of antigen-specific antibodies.

12. The method of claim 11, wherein the antigen-specific immune response comprises an antigen-specific Th1 immune response.

13. The method of claim 5, wherein the composition further comprises a mRNA encoding at least a second viral antigen or an antigenic fragment thereof.

14. The method of claim 13, wherein the second antigen comprises a coronavirus antigen or an influenza antigen.

15. The method of claim 14, wherein the second antigen is an influenza hemagglutinin (HA) virus antigen, or an antigenic fragment thereof.

16. The method of claim 14, wherein the second antigen is coronavirus spike protein, or an antigenic fragment thereof.

17. The method of claim 5, further comprising administering at least a second dose of the composition to the subject.

18. The method of claim 17, wherein the second dose of the composition is administered at least 10 days after the first administration.

19. The method of claim 5, wherein the composition further comprises polyethyleneglycol.

20. The method of claim 5, wherein the sequence of the mRNA that encodes the RSV fusion protein, or an antigenic fragment thereof, has a G/C content which is increased compared to a wild type RNA sequence encoding the RSV fusion protein or the antigen antigenic fragment thereof.

21. The method of claim 20, wherein the G/C content which is increased by at least 15 percentage points compared to a wild type RNA sequence encoding the RSV fusion protein or the antigenic fragment thereof.

22. The method of claim 20, wherein the G/C content which is increased by at least 20 percentage points compared to a wild type RNA sequence encoding the RSV fusion protein or the antigenic fragment thereof.

23. The method of claim 5, wherein the mRNA comprises, from 5' to 3':

(i) the 5' cap;

(ii) a 5' untranslated region (UTR);

(iii) the sequence encoding the RSV fusion protein, or an antigenic fragment thereof;

(iv) a 3' UTR; and (v) the poly-A sequence.

24. The method of claim 23, wherein the poly-A sequence is located at the 3' terminus of the mRNA.

25. A method for stimulating a protective antigen specific immune response in a subject comprising, administering to the subject an effective amount of a composition comprising a purified mRNA encoding a respiratory syncytial virus (RSV) fusion protein, or an antigenic fragment thereof, said mRNA comprising: a 5' cap, a poly-A sequence and at least one base modification, said composition comprising a cationic lipid, wherein the subject is 3 months to 2 years of age and wherein the composition is administered by intramuscular injection.

26. The method of claim 25, wherein the sequence of the mRNA that encodes the RSV fusion protein, or an antigenic fragment thereof, has a G/C content which is increased compared to a wild type RNA sequence encoding the RSV fusion protein or the antigen antigenic fragment thereof.

27. The method of claim 26, wherein the G/C content which is increased by at least 15 percentage points compared to a wild type RNA sequence encoding the RSV fusion protein or the antigenic fragment thereof.

28. The method of claim 27, wherein the G/C content which is increased by at least 20 percentage points compared to a wild type RNA sequence encoding the RSV fusion protein or the antigenic fragment thereof.

29. The method of claim 25, wherein the mRNA comprises, from 5' to 3':

(i) the 5' cap;

(ii) a 5' untranslated region (UTR);

(iii) the sequence encoding the RSV fusion protein, or an antigenic fragment thereof;

(iv) a 3' UTR; and (v) the poly-A sequence.

30. The method of claim 29, wherein the poly-A sequence is located at the 3' terminus of the mRNA.

31. The method of claim 29, wherein the RSV fusion protein is a full length RSV fusion protein.

32. The method of claim 29, wherein the mRNA encodes an antigenic fragment of the RSV fusion protein.

33. The method of claim 29, wherein the subject is no more than 1 year of age.

34. The method of claim 33, wherein the subject is no more than 6 months of age.

35. The method of claim 29, wherein the composition further comprises an adjuvant.

36. The method of claim 29, wherein the antigen-specific immune response comprises production of antigen-specific antibodies.

37. The method of claim 29, wherein the antigen-specific immune response comprises an antigen-specific Th1 immune response.

38. The method of claim 29, wherein the composition further comprises a mRNA encoding at least a second viral antigen or an antigenic fragment thereof.

39. The method of claim 38, wherein the second antigen comprises a coronavirus antigen or an influenza antigen.

40. The method of claim 39, wherein the second antigen is an influenza hemagglutinin (HA) virus antigen, or an antigenic fragment thereof.

41. The method of claim 39, wherein the second antigen is coronavirus spike protein, or an antigenic fragment thereof.

42. The method of claim 29, further comprising administering at least a second dose of the composition to the subject.

43. The method of claim 42, wherein the second dose of the composition is administered at least 10 days after the first administration.

44. The method of claim 29, wherein the composition further comprises polyethyleneglycol.

45. The method of claim 5, wherein the antigen-specific immune response comprises a CD8+ T cell response.

46. The method of claim 25, wherein the antigen-specific immune response comprises a CD8+ T cell response.

47. The method of claim 29, wherein the antigen-specific immune response comprises a CD8+ T cell response.

* * * * *

SEQUENCE LISTING

```
Sequence total quantity: 385
SEQ ID NO: 1            moltype = AA  length = 9
FEATURE                 Location/Qualifiers
REGION                  1..9
                        note = Description of Sequence: cationic or polycationic
                         peptide of formula (Ib): Cys

 Cys
source                  1..9
                        mol_type = protein
                        organism = synthetic construct
SEQUENCE: 1
CRRRRRRRC                                                            9

SEQ ID NO: 2            moltype = AA  length = 10
FEATURE                 Location/Qualifiers
REGION                  1..10
                        note = Description of Sequence: cationic or polycationic
                         peptide of formula (Ib): Cys

 Cys
source                  1..10
                        mol_type = protein
```

-continued

```
                        organism = synthetic construct
SEQUENCE: 2
CRRRRRRRRC                                                          10

SEQ ID NO: 3            moltype = AA  length = 11
FEATURE                 Location/Qualifiers
REGION                  1..11
                        note = Description of Sequence: cationic or polycationic
                         peptide of formula (Ib): Cys

 Cys
source                  1..11
                        mol_type = protein
                        organism = synthetic construct
SEQUENCE: 3
CRRRRRRRRR C                                                        11

SEQ ID NO: 4            moltype = AA  length = 12
FEATURE                 Location/Qualifiers
REGION                  1..12
                        note = Description of Sequence: cationic or polycationic
                         peptide of formula (Ib): Cys

 Cys
source                  1..12
                        mol_type = protein
                        organism = synthetic construct
SEQUENCE: 4
CRRRRRRRRR RC                                                       12

SEQ ID NO: 5            moltype = AA  length = 13
FEATURE                 Location/Qualifiers
REGION                  1..13
                        note = Description of Sequence: cationic or polycationic
                         peptide of formula (Ib): Cys

 Cys
source                  1..13
                        mol_type = protein
                        organism = synthetic construct
SEQUENCE: 5
CRRRRRRRRR RRC                                                      13

SEQ ID NO: 6            moltype = AA  length = 14
FEATURE                 Location/Qualifiers
REGION                  1..14
                        note = Description of Sequence: cationic or polycationic
                         peptide of formula (Ib): Cys

 Cys
source                  1..14
                        mol_type = protein
                        organism = synthetic construct
SEQUENCE: 6
CRRRRRRRRR RRRC                                                     14

SEQ ID NO: 7            moltype = AA  length = 15
FEATURE                 Location/Qualifiers
REGION                  1..15
                        note = Description of Sequence: cationic or polycationic
                         peptide of formula (Ib): Cys

 Cys
source                  1..15
                        mol_type = protein
                        organism = synthetic construct
SEQUENCE: 7
CRRRRRRRRR RRRRC                                                    15

SEQ ID NO: 8            moltype = AA  length = 16
FEATURE                 Location/Qualifiers
REGION                  1..16
                        note = Description of Sequence: cationic or polycationic
                         peptide of formula (Ib): Cys

 Cys
source                  1..16
                        mol_type = protein
                        organism = synthetic construct
SEQUENCE: 8
```

-continued

```
CRRRRRRRRR RRRRRC                                                 16

SEQ ID NO: 9           moltype = AA  length = 17
FEATURE                Location/Qualifiers
REGION                 1..17
                       note = Description of Sequence: cationic or polycationic
                        peptide of formula (Ib): Cys

 Cys
source                 1..17
                       mol_type = protein
                       organism = synthetic construct
SEQUENCE: 9
CRRRRRRRRR RRRRRRC                                                17

SEQ ID NO: 10          moltype = AA  length = 18
FEATURE                Location/Qualifiers
REGION                 1..18
                       note = Description of Sequence: cationic or polycationic
                        peptide of formula (Ib): Cys

 Cys
source                 1..18
                       mol_type = protein
                       organism = synthetic construct
SEQUENCE: 10
CRRRRRRRRR RRRRRRRC                                               18

SEQ ID NO: 11          moltype = AA  length = 19
FEATURE                Location/Qualifiers
REGION                 1..19
                       note = Description of Sequence: cationic or polycationic
                        peptide of formula (Ib): Cys

 Cys
source                 1..19
                       mol_type = protein
                       organism = synthetic construct
SEQUENCE: 11
CRRRRRRRRR RRRRRRRRC                                              19

SEQ ID NO: 12          moltype = AA  length = 20
FEATURE                Location/Qualifiers
REGION                 1..20
                       note = Description of Sequence: cationic or polycationic
                        peptide of formula (Ib): Cys

 Cys
source                 1..20
                       mol_type = protein
                       organism = synthetic construct
SEQUENCE: 12
CRRRRRRRRR RRRRRRRRRC                                             20

SEQ ID NO: 13          moltype = AA  length = 21
FEATURE                Location/Qualifiers
REGION                 1..21
                       note = Description of Sequence: cationic or polycationic
                        peptide of formula (Ib): Cys

 Cys
source                 1..21
                       mol_type = protein
                       organism = synthetic construct
SEQUENCE: 13
CRRRRRRRRR RRRRRRRRRR C                                           21

SEQ ID NO: 14          moltype = AA  length = 22
FEATURE                Location/Qualifiers
REGION                 1..22
                       note = Description of Sequence: cationic or polycationic
                        peptide of formula (Ib): Cys

 Cys
source                 1..22
                       mol_type = protein
                       organism = synthetic construct
SEQUENCE: 14
CRRRRRRRRR RRRRRRRRRR RC                                          22
```

-continued

```
SEQ ID NO: 15          moltype =   length =
SEQUENCE: 15
000

SEQ ID NO: 16          moltype =   length =
SEQUENCE: 16
000

SEQ ID NO: 17          moltype =   length =
SEQUENCE: 17
000

SEQ ID NO: 18          moltype =   length =
SEQUENCE: 18
000

SEQ ID NO: 19          moltype =   length =
SEQUENCE: 19
000

SEQ ID NO: 20          moltype =   length =
SEQUENCE: 20
000

SEQ ID NO: 21          moltype =   length =
SEQUENCE: 21
000

SEQ ID NO: 22          moltype =   length =
SEQUENCE: 22
000

SEQ ID NO: 23          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 23
WYWY                                                                4

SEQ ID NO: 24          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 24
YWYW                                                                4

SEQ ID NO: 25          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 25
WWWW                                                                4

SEQ ID NO: 26          moltype =   length =
SEQUENCE: 26
000

SEQ ID NO: 27          moltype =   length =
SEQUENCE: 27
000

SEQ ID NO: 28          moltype =   length =
SEQUENCE: 28
000

SEQ ID NO: 29          moltype =   length =
SEQUENCE: 29
000

SEQ ID NO: 30          moltype =   length =
```

-continued

```
SEQUENCE: 30
000

SEQ ID NO: 31          moltype =   length =
SEQUENCE: 31
000

SEQ ID NO: 32          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 32
FYFY                                                                        4

SEQ ID NO: 33          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 33
YFYF                                                                        4

SEQ ID NO: 34          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 34
FFFF                                                                        4

SEQ ID NO: 35          moltype =   length =
SEQUENCE: 35
000

SEQ ID NO: 36          moltype =   length =
SEQUENCE: 36
000

SEQ ID NO: 37          moltype =   length =
SEQUENCE: 37
000

SEQ ID NO: 38          moltype =   length =
SEQUENCE: 38
000

SEQ ID NO: 39          moltype =   length =
SEQUENCE: 39
000

SEQ ID NO: 40          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 40
FWFW                                                                        4

SEQ ID NO: 41          moltype = AA  length = 4
FEATURE                Location/Qualifiers
REGION                 1..4
                       note = Exemplary aromatic amino acid component (AA)
source                 1..4
                       mol_type = protein
                       organism = synthetic construct
SEQUENCE: 41
WFWF                                                                        4

SEQ ID NO: 42          moltype = AA  length = 4
FEATURE                Location/Qualifiers
```

-continued

```
REGION                  1..4
                        note = Exemplary aromatic amino acid component (AA)
source                  1..4
                        mol_type = protein
                        organism = synthetic construct
SEQUENCE: 42
YYYY                                                                        4

SEQ ID NO: 43           moltype =   length =
SEQUENCE: 43
000

SEQ ID NO: 44           moltype =   length =
SEQUENCE: 44
000

SEQ ID NO: 45           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 45
CWYC                                                                        4

SEQ ID NO: 46           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 46
CYWC                                                                        4

SEQ ID NO: 47           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 47
CWWC                                                                        4

SEQ ID NO: 48           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 48
CYYC                                                                        4

SEQ ID NO: 49           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 49
CWYWC                                                                       5

SEQ ID NO: 50           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 50
CYWYC                                                                       5

SEQ ID NO: 51           moltype = AA  length = 5
FEATURE                 Location/Qualifiers
REGION                  1..5
```

```
                        note = Exemplary aromatic amino acid component (AA)
source                  1..5
                        mol_type = protein
                        organism = synthetic construct
SEQUENCE: 51
CWWWC                                                                    5

SEQ ID NO: 52           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 52
CYYYC                                                                    5

SEQ ID NO: 53           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 53
CWYWYC                                                                   6

SEQ ID NO: 54           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 54
CYWYWC                                                                   6

SEQ ID NO: 55           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 55
CWWWWC                                                                   6

SEQ ID NO: 56           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 56
CYYYYC                                                                   6

SEQ ID NO: 57           moltype =   length =
SEQUENCE: 57
000

SEQ ID NO: 58           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 58
CFYC                                                                     4

SEQ ID NO: 59           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 59
```

```
CYFC                                                                    4

SEQ ID NO: 60           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 60
CFFC                                                                    4

SEQ ID NO: 61           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 61
CYYC                                                                    4

SEQ ID NO: 62           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 62
CFYFC                                                                   5

SEQ ID NO: 63           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 63
CYFYC                                                                   5

SEQ ID NO: 64           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 64
CFFFC                                                                   5

SEQ ID NO: 65           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 65
CYYYC                                                                   5

SEQ ID NO: 66           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 66
CFYFYC                                                                  6

SEQ ID NO: 67           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
```

```
SEQUENCE: 67
CYFYF                                                        5

SEQ ID NO: 68           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 68
CFFFFC                                                       6

SEQ ID NO: 69           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 69
CFWC                                                         4

SEQ ID NO: 70           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 70
CWFC                                                         4

SEQ ID NO: 71           moltype = AA  length = 4
FEATURE                 Location/Qualifiers
REGION                  1..4
                        note = Exemplary aromatic amino acid component (AA)
source                  1..4
                        mol_type = protein
                        organism = synthetic construct
SEQUENCE: 71
CFFC                                                         4

SEQ ID NO: 72           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 72
CFWFC                                                        5

SEQ ID NO: 73           moltype = AA  length = 5
FEATURE                 Location/Qualifiers
REGION                  1..5
                        note = Exemplary aromatic amino acid component (AA)
source                  1..5
                        mol_type = protein
                        organism = synthetic construct
SEQUENCE: 73
CWFWC                                                        5

SEQ ID NO: 74           moltype = AA  length = 6
FEATURE                 Location/Qualifiers
REGION                  1..6
                        note = Exemplary aromatic amino acid component (AA)
source                  1..6
                        mol_type = protein
                        organism = synthetic construct
SEQUENCE: 74
CFWFWC                                                       6

SEQ ID NO: 75           moltype = AA  length = 6
FEATURE                 Location/Qualifiers
REGION                  1..6
                        note = Exemplary aromatic amino acid component (AA)
source                  1..6
                        mol_type = protein
```

```
                        organism = synthetic construct
SEQUENCE: 75
CWFWFC                                                      6

SEQ ID NO: 76           moltype =   length =
SEQUENCE: 76
000

SEQ ID NO: 77           moltype =   length =
SEQUENCE: 77
000

SEQ ID NO: 78           moltype =   length =
SEQUENCE: 78
000

SEQ ID NO: 79           moltype =   length =
SEQUENCE: 79
000

SEQ ID NO: 80           moltype =   length =
SEQUENCE: 80
000

SEQ ID NO: 81           moltype =   length =
SEQUENCE: 81
000

SEQ ID NO: 82           moltype =   length =
SEQUENCE: 82
000

SEQ ID NO: 83           moltype =   length =
SEQUENCE: 83
000

SEQ ID NO: 84           moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 84
STST                                                        4

SEQ ID NO: 85           moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 85
TSTS                                                        4

SEQ ID NO: 86           moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 86
SSSS                                                        4

SEQ ID NO: 87           moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 87
TTTT                                                        4
```

```
SEQ ID NO: 88          moltype =   length =
SEQUENCE: 88
000

SEQ ID NO: 89          moltype =   length =
SEQUENCE: 89
000

SEQ ID NO: 90          moltype =   length =
SEQUENCE: 90
000

SEQ ID NO: 91          moltype =   length =
SEQUENCE: 91
000

SEQ ID NO: 92          moltype =   length =
SEQUENCE: 92
000

SEQ ID NO: 93          moltype =   length =
SEQUENCE: 93
000

SEQ ID NO: 94          moltype =   length =
SEQUENCE: 94
000

SEQ ID NO: 95          moltype =   length =
SEQUENCE: 95
000

SEQ ID NO: 96          moltype = AA  length = 4
FEATURE                Location/Qualifiers
REGION                 1..4
                       note = Exemplary hydrophilic (and preferably non charged
                        polar) amino acid component (AA)
source                 1..4
                       mol_type = protein
                       organism = synthetic construct
SEQUENCE: 96
QNQN                                                         4

SEQ ID NO: 97          moltype = AA  length = 4
FEATURE                Location/Qualifiers
REGION                 1..4
                       note = Exemplary hydrophilic (and preferably non charged
                        polar) amino acid component (AA)
source                 1..4
                       mol_type = protein
                       organism = synthetic construct
SEQUENCE: 97
NQNQ                                                         4

SEQ ID NO: 98          moltype = AA  length = 4
FEATURE                Location/Qualifiers
REGION                 1..4
                       note = Exemplary hydrophilic (and preferably non charged
                        polar) amino acid component (AA)
source                 1..4
                       mol_type = protein
                       organism = synthetic construct
SEQUENCE: 98
QQQQ                                                         4

SEQ ID NO: 99          moltype = AA  length = 4
FEATURE                Location/Qualifiers
REGION                 1..4
                       note = Exemplary hydrophilic (and preferably non charged
                        polar) amino acid component (AA)
source                 1..4
                       mol_type = protein
                       organism = synthetic construct
SEQUENCE: 99
NNNN                                                         4

SEQ ID NO: 100         moltype =   length =
SEQUENCE: 100
```

```
000

SEQ ID NO: 101          moltype =   length =
SEQUENCE: 101
000

SEQ ID NO: 102          moltype =   length =
SEQUENCE: 102
000

SEQ ID NO: 103          moltype =   length =
SEQUENCE: 103
000

SEQ ID NO: 104          moltype =   length =
SEQUENCE: 104
000

SEQ ID NO: 105          moltype =   length =
SEQUENCE: 105
000

SEQ ID NO: 106          moltype =   length =
SEQUENCE: 106
000

SEQ ID NO: 107          moltype =   length =
SEQUENCE: 107
000

SEQ ID NO: 108          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 108
SNSN                                                                        4

SEQ ID NO: 109          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 109
NSNS                                                                        4

SEQ ID NO: 110          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 110
SSSS                                                                        4

SEQ ID NO: 111          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 111
NNNN                                                                        4

SEQ ID NO: 112          moltype =   length =
SEQUENCE: 112
000

SEQ ID NO: 113          moltype =   length =
```

```
SEQUENCE: 113
000

SEQ ID NO: 114          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 114
CSTC                                                                        4

SEQ ID NO: 115          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 115
CTSC                                                                        4

SEQ ID NO: 116          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 116
CSSC                                                                        4

SEQ ID NO: 117          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 117
CTTC                                                                        4

SEQ ID NO: 118          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 118
CSTSC                                                                       5

SEQ ID NO: 119          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 119
CTSTC                                                                       5

SEQ ID NO: 120          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 120
CSSSC                                                                       5
```

```
SEQ ID NO: 121          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 121
CTTTC                                                                5

SEQ ID NO: 122          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 122
CSTSTC                                                               6

SEQ ID NO: 123          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 123
CTSTSC                                                               6

SEQ ID NO: 124          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 124
CSSSSC                                                               6

SEQ ID NO: 125          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 125
CTTTTC                                                               6

SEQ ID NO: 126          moltype =   length =
SEQUENCE: 126
000

SEQ ID NO: 127          moltype =   length =
SEQUENCE: 127
000

SEQ ID NO: 128          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 128
CQNC                                                                 4

SEQ ID NO: 129          moltype = AA  length = 4
FEATURE                 Location/Qualifiers
REGION                  1..4
                        note = Exemplary hydrophilic (and preferably non charged
```

```
                         polar) amino acid component (AA)
source                   1..4
                         mol_type = protein
                         organism = synthetic construct
SEQUENCE: 129
CNQC                                                                          4

SEQ ID NO: 130           moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 130
CQQC                                                                          4

SEQ ID NO: 131           moltype = AA  length = 4
FEATURE                  Location/Qualifiers
REGION                   1..4
                         note = Exemplary hydrophilic (and preferably non charged
                          polar) amino acid component (AA)
source                   1..4
                         mol_type = protein
                         organism = synthetic construct
SEQUENCE: 131
CNNC                                                                          4

SEQ ID NO: 132           moltype = AA  length = 5
FEATURE                  Location/Qualifiers
REGION                   1..5
                         note = Exemplary hydrophilic (and preferably non charged
                          polar) amino acid component (AA)
source                   1..5
                         mol_type = protein
                         organism = synthetic construct
SEQUENCE: 132
CQNQC                                                                         5

SEQ ID NO: 133           moltype = AA  length = 5
FEATURE                  Location/Qualifiers
REGION                   1..5
                         note = Exemplary hydrophilic (and preferably non charged
                          polar) amino acid component (AA)
source                   1..5
                         mol_type = protein
                         organism = synthetic construct
SEQUENCE: 133
CNQNC                                                                         5

SEQ ID NO: 134           moltype = AA  length = 5
FEATURE                  Location/Qualifiers
REGION                   1..5
                         note = Exemplary hydrophilic (and preferably non charged
                          polar) amino acid component (AA)
source                   1..5
                         mol_type = protein
                         organism = synthetic construct
SEQUENCE: 134
CQQQC                                                                         5

SEQ ID NO: 135           moltype = AA  length = 5
FEATURE                  Location/Qualifiers
REGION                   1..5
                         note = Exemplary hydrophilic (and preferably non charged
                          polar) amino acid component (AA)
source                   1..5
                         mol_type = protein
                         organism = synthetic construct
SEQUENCE: 135
CNNNC                                                                         5

SEQ ID NO: 136           moltype = AA  length = 6
FEATURE                  Location/Qualifiers
REGION                   1..6
                         note = Exemplary hydrophilic (and preferably non charged
                          polar) amino acid component (AA)
source                   1..6
```

```
                        mol_type = protein
                        organism = synthetic construct
SEQUENCE: 136
CQNQNC                                                          6

SEQ ID NO: 137          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 137
CNQNQC                                                          6

SEQ ID NO: 138          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 138
CQQQQC                                                          6

SEQ ID NO: 139          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 139
CNNNNC                                                          6

SEQ ID NO: 140          moltype =   length =
SEQUENCE: 140
000

SEQ ID NO: 141          moltype =   length =
SEQUENCE: 141
000

SEQ ID NO: 142          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 142
CSNC                                                            4

SEQ ID NO: 143          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 143
CNSC                                                            4

SEQ ID NO: 144          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 144
CSSC                                                            4
```

-continued

```
SEQ ID NO: 145          moltype = AA  length = 4
FEATURE                 Location/Qualifiers
REGION                  1..4
                        note = Exemplary hydrophilic (and preferably non charged
                         polar) amino acid component (AA)
source                  1..4
                        mol_type = protein
                        organism = synthetic construct
SEQUENCE: 145
CNNC                                                                        4

SEQ ID NO: 146          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 146
CSNSC                                                                       5

SEQ ID NO: 147          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 147
CNSNC                                                                       5

SEQ ID NO: 148          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 148
CSSSC                                                                       5

SEQ ID NO: 149          moltype = AA  length = 5
FEATURE                 Location/Qualifiers
REGION                  1..5
                        note = Exemplary hydrophilic (and preferably non charged
                         polar) amino acid component (AA)
source                  1..5
                        mol_type = protein
                        organism = synthetic construct
SEQUENCE: 149
CNNNC                                                                       5

SEQ ID NO: 150          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 150
CSNSNC                                                                      6

SEQ ID NO: 151          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 151
CNSNSC                                                                      6

SEQ ID NO: 152          moltype = AA  length = 6
FEATURE                 Location/Qualifiers
```

-continued

```
REGION                  1..6
                        note = Exemplary hydrophilic (and preferably non charged
                         polar) amino acid component (AA)
source                  1..6
                        mol_type = protein
                        organism = synthetic construct
SEQUENCE: 152
CSSSSC                                                                     6

SEQ ID NO: 153          moltype = AA  length = 6
FEATURE                 Location/Qualifiers
REGION                  1..6
                        note = Exemplary hydrophilic (and preferably non charged
                         polar) amino acid component (AA)
source                  1..6
                        mol_type = protein
                        organism = synthetic construct
SEQUENCE: 153
CNNNNC                                                                     6

SEQ ID NO: 154          moltype =   length =
SEQUENCE: 154
000

SEQ ID NO: 155          moltype =   length =
SEQUENCE: 155
000

SEQ ID NO: 156          moltype =   length =
SEQUENCE: 156
000

SEQ ID NO: 157          moltype =   length =
SEQUENCE: 157
000

SEQ ID NO: 158          moltype =   length =
SEQUENCE: 158
000

SEQ ID NO: 159          moltype =   length =
SEQUENCE: 159
000

SEQ ID NO: 160          moltype =   length =
SEQUENCE: 160
000

SEQ ID NO: 161          moltype =   length =
SEQUENCE: 161
000

SEQ ID NO: 162          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 162
LVLV                                                                       4

SEQ ID NO: 163          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 163
VLVL                                                                       4

SEQ ID NO: 164          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
```

```
SEQUENCE: 164
LLLL                                                                    4

SEQ ID NO: 165          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 165
VVVV                                                                    4

SEQ ID NO: 166          moltype =   length =
SEQUENCE: 166
000

SEQ ID NO: 167          moltype =   length =
SEQUENCE: 167
000

SEQ ID NO: 168          moltype =   length =
SEQUENCE: 168
000

SEQ ID NO: 169          moltype =   length =
SEQUENCE: 169
000

SEQ ID NO: 170          moltype =   length =
SEQUENCE: 170
000

SEQ ID NO: 171          moltype =   length =
SEQUENCE: 171
000

SEQ ID NO: 172          moltype =   length =
SEQUENCE: 172
000

SEQ ID NO: 173          moltype =   length =
SEQUENCE: 173
000

SEQ ID NO: 174          moltype =   length =
SEQUENCE: 174
000

SEQ ID NO: 175          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 175
AIAI                                                                    4

SEQ ID NO: 176          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 176
IIII                                                                    4

SEQ ID NO: 177          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 177
AAAA                                                                    4
```

-continued

```
SEQ ID NO: 178          moltype =   length =
SEQUENCE: 178
000

SEQ ID NO: 179          moltype =   length =
SEQUENCE: 179
000

SEQ ID NO: 180          moltype =   length =
SEQUENCE: 180
000

SEQ ID NO: 181          moltype =   length =
SEQUENCE: 181
000

SEQ ID NO: 182          moltype =   length =
SEQUENCE: 182
000

SEQ ID NO: 183          moltype =   length =
SEQUENCE: 183
000

SEQ ID NO: 184          moltype =   length =
SEQUENCE: 184
000

SEQ ID NO: 185          moltype =   length =
SEQUENCE: 185
000

SEQ ID NO: 186          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 186
MAMA                                                                4

SEQ ID NO: 187          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 187
AMAM                                                                4

SEQ ID NO: 188          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 188
MMMM                                                                4

SEQ ID NO: 189          moltype =   length =
SEQUENCE: 189
000

SEQ ID NO: 190          moltype =   length =
SEQUENCE: 190
000

SEQ ID NO: 191          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 191
CLVC                                                                4
```

```
SEQ ID NO: 192          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 192
CVLC                                                                  4

SEQ ID NO: 193          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 193
CLLC                                                                  4

SEQ ID NO: 194          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 194
CVVC                                                                  4

SEQ ID NO: 195          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 195
CLVLC                                                                 5

SEQ ID NO: 196          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 196
CVLVC                                                                 5

SEQ ID NO: 197          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 197
CLLLC                                                                 5

SEQ ID NO: 198          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 198
CVVVC                                                                 5

SEQ ID NO: 199          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 199
```

```
CLVLVC                                                      6

SEQ ID NO: 200          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 200
CVLVLC                                                      6

SEQ ID NO: 201          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 201
CLLLLC                                                      6

SEQ ID NO: 202          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 202
CVVVVC                                                      6

SEQ ID NO: 203          moltype =   length =
SEQUENCE: 203
000

SEQ ID NO: 204          moltype =   length =
SEQUENCE: 204
000

SEQ ID NO: 205          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 205
CIAC                                                        4

SEQ ID NO: 206          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 206
CAIC                                                        4

SEQ ID NO: 207          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 207
CIIC                                                        4

SEQ ID NO: 208          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 208
CAAC                                                        4
```

```
SEQ ID NO: 209          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 209
CIAIC                                                                       5

SEQ ID NO: 210          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 210
CAIAC                                                                       5

SEQ ID NO: 211          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 211
CIIIC                                                                       5

SEQ ID NO: 212          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 212
CAAAC                                                                       5

SEQ ID NO: 213          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 213
CIAIAC                                                                      6

SEQ ID NO: 214          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 214
CAIAIC                                                                      6

SEQ ID NO: 215          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 215
CIIIIC                                                                      6

SEQ ID NO: 216          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 216
```

```
CAAAAC                                                          6

SEQ ID NO: 217          moltype =   length =
SEQUENCE: 217
000

SEQ ID NO: 218          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 218
CMAC                                                            4

SEQ ID NO: 219          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 219
CAMC                                                            4

SEQ ID NO: 220          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 220
CMMC                                                            4

SEQ ID NO: 221          moltype = AA  length = 4
FEATURE                 Location/Qualifiers
REGION                  1..4
                        note = Exemplary lipophilic amino acid component (AA)
source                  1..4
                        mol_type = protein
                        organism = synthetic construct
SEQUENCE: 221
CAAC                                                            4

SEQ ID NO: 222          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 222
CMAMC                                                           5

SEQ ID NO: 223          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 223
CAMAC                                                           5

SEQ ID NO: 224          moltype = AA  length = 5
FEATURE                 Location/Qualifiers
REGION                  1..5
                        note = Exemplary lipophilic amino acid component (AA)
source                  1..5
                        mol_type = protein
                        organism = synthetic construct
SEQUENCE: 224
CMMMC                                                           5

SEQ ID NO: 225          moltype = AA  length = 5
FEATURE                 Location/Qualifiers
REGION                  1..5
```

```
                        note = Exemplary lipophilic amino acid component (AA)
source                  1..5
                        mol_type = protein
                        organism = synthetic construct
SEQUENCE: 225
CAAAC                                                                     5

SEQ ID NO: 226          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 226
CMAMAC                                                                    6

SEQ ID NO: 227          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 227
CAMAMC                                                                    6

SEQ ID NO: 228          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 228
CMMMMC                                                                    6

SEQ ID NO: 229          moltype = AA  length = 6
FEATURE                 Location/Qualifiers
REGION                  1..6
                        note = Exemplary lipophilic amino acid component (AA)
source                  1..6
                        mol_type = protein
                        organism = synthetic construct
SEQUENCE: 229
CAAAAC                                                                    6

SEQ ID NO: 230          moltype =   length =
SEQUENCE: 230
000

SEQ ID NO: 231          moltype =   length =
SEQUENCE: 231
000

SEQ ID NO: 232          moltype =   length =
SEQUENCE: 232
000

SEQ ID NO: 233          moltype =   length =
SEQUENCE: 233
000

SEQ ID NO: 234          moltype =   length =
SEQUENCE: 234
000

SEQ ID NO: 235          moltype =   length =
SEQUENCE: 235
000

SEQ ID NO: 236          moltype =   length =
SEQUENCE: 236
000

SEQ ID NO: 237          moltype =   length =
SEQUENCE: 237
000
```

-continued

```
SEQ ID NO: 238          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 238
DHDH                                                                       4

SEQ ID NO: 239          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 239
HDHD                                                                       4

SEQ ID NO: 240          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 240
DDDD                                                                       4

SEQ ID NO: 241          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 241
HHHH                                                                       4

SEQ ID NO: 242          moltype =   length =
SEQUENCE: 242
000

SEQ ID NO: 243          moltype =   length =
SEQUENCE: 243
000

SEQ ID NO: 244          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 244
CDHC                                                                       4

SEQ ID NO: 245          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 245
CHDC                                                                       4

SEQ ID NO: 246          moltype = AA  length = 4
FEATURE                 Location/Qualifiers
REGION                  1..4
                        note = Exemplary weak basic amino acid component (AA)
source                  1..4
                        mol_type = protein
                        organism = synthetic construct
SEQUENCE: 246
CDDC                                                                       4

SEQ ID NO: 247          moltype = AA  length = 4
```

-continued

```
FEATURE                 Location/Qualifiers
REGION                  1..4
                        note = Exemplary weak basic amino acid component (AA)
source                  1..4
                        mol_type = protein
                        organism = synthetic construct
SEQUENCE: 247
CHHC                                                                        4

SEQ ID NO: 248          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 248
CDHDC                                                                       5

SEQ ID NO: 249          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 249
CHDHC                                                                       5

SEQ ID NO: 250          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 250
CDDDC                                                                       5

SEQ ID NO: 251          moltype = AA  length = 5
FEATURE                 Location/Qualifiers
REGION                  1..5
                        note = Exemplary weak basic amino acid component (AA)
source                  1..5
                        mol_type = protein
                        organism = synthetic construct
SEQUENCE: 251
CHHHC                                                                       5

SEQ ID NO: 252          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 252
CDHDHC                                                                      6

SEQ ID NO: 253          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 253
CHDHDC                                                                      6

SEQ ID NO: 254          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 254
CDDDDC                                                                      6
```

-continued

```
SEQ ID NO: 255          moltype = AA  length = 6
FEATURE                 Location/Qualifiers
REGION                  1..6
                        note = Exemplary weak basic amino acid component (AA)
source                  1..6
                        mol_type = protein
                        organism = synthetic construct
SEQUENCE: 255
CHHHHC                                                                      6

SEQ ID NO: 256          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 256
KDEL                                                                        4

SEQ ID NO: 257          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 257
DDEL                                                                        4

SEQ ID NO: 258          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 258
DEEL                                                                        4

SEQ ID NO: 259          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 259
QEDL                                                                        4

SEQ ID NO: 260          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 260
RDEL                                                                        4

SEQ ID NO: 261          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
```

```
SEQUENCE: 261
GQNLSTSN                                                           8

SEQ ID NO: 262          moltype = AA  length = 7
FEATURE                 Location/Qualifiers
REGION                  1..7
                        note = Description of sequence: signal peptide,
                         localization signal or sequence or nuclear localization
                         signal
source                  1..7
                        mol_type = protein
                        organism = synthetic construct
SEQUENCE: 262
PKKKRKV                                                            7

SEQ ID NO: 263          moltype = AA  length = 7
FEATURE                 Location/Qualifiers
REGION                  1..7
                        note = Description of sequence: signal peptide,
                         localization signal or sequence or nuclear localization
                         signal
source                  1..7
                        mol_type = protein
                        organism = synthetic construct
SEQUENCE: 263
PQKKIKS                                                            7

SEQ ID NO: 264          moltype = AA  length = 5
FEATURE                 Location/Qualifiers
REGION                  1..5
                        note = Description of sequence: signal peptide,
                         localization signal or sequence or nuclear localization
                         signal
source                  1..5
                        mol_type = protein
                        organism = synthetic construct
SEQUENCE: 264
QPKKP                                                              5

SEQ ID NO: 265          moltype = AA  length = 4
FEATURE                 Location/Qualifiers
REGION                  1..4
                        note = Description of sequence: signal peptide,
                         localization signal or sequence or nuclear localization
                         signal
source                  1..4
                        mol_type = protein
                        organism = synthetic construct
SEQUENCE: 265
RKKR                                                               4

SEQ ID NO: 266          moltype = AA  length = 12
FEATURE                 Location/Qualifiers
REGION                  1..12
                        note = Description of sequence: signal peptide,
                         localization signal or sequence or nuclear localization
                         signal
source                  1..12
                        mol_type = protein
                        organism = synthetic construct
SEQUENCE: 266
RKKRRQRRRA HQ                                                      12

SEQ ID NO: 267          moltype = AA  length = 16
FEATURE                 Location/Qualifiers
REGION                  1..16
                        note = Description of sequence: signal peptide,
                         localization signal or sequence or nuclear localization
                         signal
source                  1..16
                        mol_type = protein
                        organism = synthetic construct
SEQUENCE: 267
RQARRNRRRR WRERQR                                                  16

SEQ ID NO: 268          moltype = AA  length = 19
FEATURE                 Location/Qualifiers
REGION                  1..19
                        note = Description of sequence: signal peptide,
```

```
                      localization signal or sequence or nuclear localization
                      signal
source               1..19
                     mol_type = protein
                     organism = synthetic construct
SEQUENCE: 268
MPLTRRRPAA SQALAPPTP                                            19

SEQ ID NO: 269       moltype = AA  length = 8
FEATURE              Location/Qualifiers
REGION               1..8
                     note = Description of sequence: signal peptide,
                      localization signal or sequence or nuclear localization
                      signal
source               1..8
                     mol_type = protein
                     organism = synthetic construct
SEQUENCE: 269
GAALTILV                                                        8

SEQ ID NO: 270       moltype = AA  length = 8
FEATURE              Location/Qualifiers
REGION               1..8
                     note = Description of sequence: signal peptide,
                      localization signal or sequence or nuclear localization
                      signal
source               1..8
                     mol_type = protein
                     organism = synthetic construct
SEQUENCE: 270
GAALTLLG                                                        8

SEQ ID NO: 271       moltype = AA  length = 15
FEATURE              Location/Qualifiers
REGION               1..15
                     note = Description of sequence: signal peptide,
                      localization signal or sequence or nuclear localization
                      signal
source               1..15
                     mol_type = protein
                     organism = synthetic construct
SEQUENCE: 271
MDDQRDLISN NEQLP                                                15

SEQ ID NO: 272       moltype = AA  length = 32
FEATURE              Location/Qualifiers
REGION               1..32
                     note = Description of sequence: signal peptide,
                      localization signal or sequence or nuclear localization
                      signal
REGION               7..8
                     note = misc_feature - Xaa can be any naturally occurring
                      amino acid
SITE                 32
                     note = misc_feature - Xaa can be any naturally occurring
                      amino acid
source               1..32
                     mol_type = protein
                     organism = synthetic construct
SEQUENCE: 272
MLFNLRXXLN NAAFRHGHNF MVRNFRCGQP LX                             32

SEQ ID NO: 273       moltype = AA  length = 8
FEATURE              Location/Qualifiers
REGION               1..8
                     note = Description of sequence: signal peptide,
                      localization signal or sequence or nuclear localization
                      signal
source               1..8
                     mol_type = protein
                     organism = synthetic construct
SEQUENCE: 273
GCVCSSNP                                                        8

SEQ ID NO: 274       moltype = AA  length = 8
FEATURE              Location/Qualifiers
REGION               1..8
                     note = Description of sequence: signal peptide,
                      localization signal or sequence or nuclear localization
```

```
                         signal
source                  1..8
                        mol_type = protein
                        organism = synthetic construct
SEQUENCE: 274
GQTVTTPL                                                        8

SEQ ID NO: 275          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 275
GQELSQHE                                                        8

SEQ ID NO: 276          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 276
GNSPSYNP                                                        8

SEQ ID NO: 277          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 277
GVSGSKGQ                                                        8

SEQ ID NO: 278          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 278
GQTITTPL                                                        8

SEQ ID NO: 279          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 279
GQTLTTPL                                                        8

SEQ ID NO: 280          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 280
GQIFSRSA                                                        8
```

```
SEQ ID NO: 281          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 281
GQIHGLSP                                                                 8

SEQ ID NO: 282          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 282
GARASVLS                                                                 8

SEQ ID NO: 283          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 283
GCTLSAEE                                                                 8

SEQ ID NO: 284          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 284
GAQVSSQK                                                                 8

SEQ ID NO: 285          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 285
GAQLSRNT                                                                 8

SEQ ID NO: 286          moltype = AA  length = 8
FEATURE                 Location/Qualifiers
REGION                  1..8
                        note = Description of sequence: signal peptide,
                         localization signal or sequence or nuclear localization
                         signal
source                  1..8
                        mol_type = protein
                        organism = synthetic construct
SEQUENCE: 286
GNAAAAKK                                                                 8

SEQ ID NO: 287          moltype = AA  length = 8
FEATURE                 Location/Qualifiers
REGION                  1..8
                        note = Description of sequence: signal peptide,
                         localization signal or sequence or nuclear localization
                         signal
source                  1..8
```

```
                          mol_type = protein
                          organism = synthetic construct
SEQUENCE: 287
GNEASYPL                                                            8

SEQ ID NO: 288            moltype = AA  length = 8
FEATURE                   Location/Qualifiers
REGION                    1..8
                          note = Description of sequence: signal peptide,
                           localization signal or sequence or nuclear localization
                           signal
source                    1..8
                          mol_type = protein
                          organism = synthetic construct
SEQUENCE: 288
GSSKSKPK                                                            8

SEQ ID NO: 289            moltype = RNA  length = 20
FEATURE                   Location/Qualifiers
misc_feature              1..20
                          note = nucleic acid sequence according to formula (II)
source                    1..20
                          mol_type = other RNA
                          organism = synthetic construct
SEQUENCE: 289
ggtttttttt tttttttggg                                               20

SEQ ID NO: 290            moltype = RNA  length = 20
FEATURE                   Location/Qualifiers
misc_feature              1..20
                          note = nucleic acid sequence according to formula (II)
source                    1..20
                          mol_type = other RNA
                          organism = synthetic construct
SEQUENCE: 290
gggggttttt tttttggggg                                               20

SEQ ID NO: 291            moltype = RNA  length = 40
FEATURE                   Location/Qualifiers
misc_feature              1..40
                          note = nucleic acid sequence according to formula (II)
source                    1..40
                          mol_type = other RNA
                          organism = synthetic construct
SEQUENCE: 291
gggggttttt tttttttttt tttttttttt tttttggggg                         40

SEQ ID NO: 292            moltype = RNA  length = 39
FEATURE                   Location/Qualifiers
misc_feature              1..39
                          note = nucleic acid sequence according to formula (II)
source                    1..39
                          mol_type = other RNA
                          organism = synthetic construct
SEQUENCE: 292
gtgtgtgtgt gttttttttt tttttttgtg tgtgtgtgt                          39

SEQ ID NO: 293            moltype = RNA  length = 39
FEATURE                   Location/Qualifiers
misc_feature              1..39
                          note = nucleic acid sequence according to formula (II)
source                    1..39
                          mol_type = other RNA
                          organism = synthetic construct
SEQUENCE: 293
ggttggttgg tttttttttt tttttttggt tggttggtt                          39

SEQ ID NO: 294            moltype = RNA  length = 20
FEATURE                   Location/Qualifiers
misc_feature              1..20
                          note = nucleic acid sequence according to formula (II)
source                    1..20
                          mol_type = other RNA
                          organism = synthetic construct
SEQUENCE: 294
gggggggggt ttgggggggg                                               20

SEQ ID NO: 295            moltype = RNA  length = 20
FEATURE                   Location/Qualifiers
```

```
misc_feature           1..20
                       note = nucleic acid sequence according to formula (II)
source                 1..20
                       mol_type = other RNA
                       organism = synthetic construct
SEQUENCE: 295
gggggggtt ttgggggggg                                       20

SEQ ID NO: 296         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 296
gggggggttt tttggggggg                                       20

SEQ ID NO: 297         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 297
gggggggttt ttttgggggg                                       20

SEQ ID NO: 298         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 298
ggggggtttt ttttgggggg                                       20

SEQ ID NO: 299         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 299
ggggggtttt tttttggggg                                       20

SEQ ID NO: 300         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 300
ggggggtttt ttttttgggg                                       20

SEQ ID NO: 301         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 301
gggggttttt ttttttgggg                                       20

SEQ ID NO: 302         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 302
gggggttttt tttttttggg                                       20

SEQ ID NO: 303         moltype = RNA  length = 20
```

-continued

```
FEATURE                Location/Qualifiers
misc_feature           1..20
                       note = nucleic acid sequence according to formula (II)
source                 1..20
                       mol_type = other RNA
                       organism = synthetic construct
SEQUENCE: 303
ggggtttttt tttttttggg                                              20

SEQ ID NO: 304         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 304
ggggtttttt ttttttttgg                                              20

SEQ ID NO: 305         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 305
ggtttttttt ttttttttgg                                              20

SEQ ID NO: 306         moltype = RNA  length = 20
FEATURE                Location/Qualifiers
misc_feature           1..20
                       note = nucleic acid sequence according to formula (II)
source                 1..20
                       mol_type = other RNA
                       organism = synthetic construct
SEQUENCE: 306
gttttttttt tttttttttg                                              20

SEQ ID NO: 307         moltype = RNA  length = 22
FEATURE                Location/Qualifiers
misc_feature           1..22
                       note = nucleic acid sequence according to formula (II)
source                 1..22
                       mol_type = other RNA
                       organism = synthetic construct
SEQUENCE: 307
gggggggggg tttggggggg gg                                           22

SEQ ID NO: 308         moltype = RNA  length = 22
FEATURE                Location/Qualifiers
misc_feature           1..22
                       note = nucleic acid sequence according to formula (II)
source                 1..22
                       mol_type = other RNA
                       organism = synthetic construct
SEQUENCE: 308
gggggggggt tttggggggg gg                                           22

SEQ ID NO: 309         moltype = RNA  length = 22
FEATURE                Location/Qualifiers
misc_feature           1..22
                       note = nucleic acid sequence according to formula (II)
source                 1..22
                       mol_type = other RNA
                       organism = synthetic construct
SEQUENCE: 309
ggggggggtt ttttgggggg gg                                           22

SEQ ID NO: 310         moltype = RNA  length = 22
FEATURE                Location/Qualifiers
misc_feature           1..22
                       note = nucleic acid sequence according to formula (II)
source                 1..22
                       mol_type = other RNA
                       organism = synthetic construct
SEQUENCE: 310
ggggggggtt tttttggggg gg                                           22
```

-continued

```
SEQ ID NO: 311          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 311
gggggggttt tttttggggg gg                                            22

SEQ ID NO: 312          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 312
gggggggttt ttttttgggg gg                                            22

SEQ ID NO: 313          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 313
gggggggttt tttttttggg gg                                            22

SEQ ID NO: 314          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 314
ggggggtttt tttttttggg gg                                            22

SEQ ID NO: 315          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 315
ggggggtttt ttttttttgg gg                                            22

SEQ ID NO: 316          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 316
gggggttttt ttttttttgg gg                                            22

SEQ ID NO: 317          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 317
gggggttttt tttttttttg gg                                            22

SEQ ID NO: 318          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 318
gggttttttt tttttttttg gg                                            22
```

```
SEQ ID NO: 319          moltype = RNA  length = 22
FEATURE                 Location/Qualifiers
misc_feature            1..22
                        note = nucleic acid sequence according to formula (II)
source                  1..22
                        mol_type = other RNA
                        organism = synthetic construct
SEQUENCE: 319
ggtttttttt tttttttttt gg                                                22

SEQ ID NO: 320          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 320
gggggggggg gtttgggggg gggg                                              24

SEQ ID NO: 321          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 321
gggggggggg ttttgggggg gggg                                              24

SEQ ID NO: 322          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 322
gggggggggt tttttggggg gggg                                              24

SEQ ID NO: 323          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 323
gggggggggt ttttttgggg gggg                                              24

SEQ ID NO: 324          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 324
ggggggggtt ttttttgggg gggg                                              24

SEQ ID NO: 325          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 325
ggggggggtt tttttttggg gggg                                              24

SEQ ID NO: 326          moltype = RNA  length = 24
FEATURE                 Location/Qualifiers
misc_feature            1..24
                        note = nucleic acid sequence according to formula (II)
source                  1..24
                        mol_type = other RNA
                        organism = synthetic construct
SEQUENCE: 326
```

-continued

```
ggggggggtt ttttttttgg gggg                                          24

SEQ ID NO: 327         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 327
gggggggttt ttttttttgg gggg                                          24

SEQ ID NO: 328         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 328
gggggggttt tttttttttg gggg                                          24

SEQ ID NO: 329         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 329
ggggggtttt tttttttttg gggg                                          24

SEQ ID NO: 330         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 330
ggggggtttt tttttttttt gggg                                          24

SEQ ID NO: 331         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 331
ggggtttttt tttttttttt gggg                                          24

SEQ ID NO: 332         moltype = RNA  length = 24
FEATURE                Location/Qualifiers
misc_feature           1..24
                       note = nucleic acid sequence according to formula (II)
source                 1..24
                       mol_type = other RNA
                       organism = synthetic construct
SEQUENCE: 332
gggttttttt tttttttttt tggg                                          24

SEQ ID NO: 333         moltype = RNA  length = 32
FEATURE                Location/Qualifiers
misc_feature           1..32
                       note = nucleic acid sequence according to formula (II)
source                 1..32
                       mol_type = other RNA
                       organism = synthetic construct
SEQUENCE: 333
gttttttttt tttttttttt tttttttttt tg                                 32

SEQ ID NO: 334         moltype = RNA  length = 34
FEATURE                Location/Qualifiers
misc_feature           1..34
                       note = nucleic acid sequence according to formula (II)
source                 1..34
                       mol_type = other RNA
                       organism = synthetic construct
```

```
SEQUENCE: 334
ggtttttttt tttttttttt tttttttttt ttgg                              34

SEQ ID NO: 335         moltype = RNA  length = 36
FEATURE                Location/Qualifiers
misc_feature           1..36
                       note = nucleic acid sequence according to formula (II)
source                 1..36
                       mol_type = other RNA
                       organism = synthetic construct
SEQUENCE: 335
gggttttttt tttttttttt tttttttttt tttggg                            36

SEQ ID NO: 336         moltype = RNA  length = 37
FEATURE                Location/Qualifiers
misc_feature           1..37
                       note = nucleic acid sequence according to formula (II)
source                 1..37
                       mol_type = other RNA
                       organism = synthetic construct
SEQUENCE: 336
ggggtttttt tttttttttt tttttttttt ttttggg                           37

SEQ ID NO: 337         moltype = RNA  length = 39
FEATURE                Location/Qualifiers
misc_feature           1..39
                       note = nucleic acid sequence according to formula (II)
source                 1..39
                       mol_type = other RNA
                       organism = synthetic construct
SEQUENCE: 337
gggggttttt tttttttttt tttttttttt tttttgggg                         39

SEQ ID NO: 338         moltype = RNA  length = 41
FEATURE                Location/Qualifiers
misc_feature           1..41
                       note = nucleic acid sequence according to formula (II)
source                 1..41
                       mol_type = other RNA
                       organism = synthetic construct
SEQUENCE: 338
ggggggtttt tttttttttt tttttttttt ttttttgggg g                      41

SEQ ID NO: 339         moltype = RNA  length = 43
FEATURE                Location/Qualifiers
misc_feature           1..43
                       note = nucleic acid sequence according to formula (II)
source                 1..43
                       mol_type = other RNA
                       organism = synthetic construct
SEQUENCE: 339
gggggggttt tttttttttt tttttttttt tttttttggg ggg                    43

SEQ ID NO: 340         moltype = RNA  length = 45
FEATURE                Location/Qualifiers
misc_feature           1..45
                       note = nucleic acid sequence according to formula (II)
source                 1..45
                       mol_type = other RNA
                       organism = synthetic construct
SEQUENCE: 340
ggggggggtt tttttttttt tttttttttt ttttttttgg ggggg                  45

SEQ ID NO: 341         moltype = RNA  length = 47
FEATURE                Location/Qualifiers
misc_feature           1..47
                       note = nucleic acid sequence according to formula (II)
source                 1..47
                       mol_type = other RNA
                       organism = synthetic construct
SEQUENCE: 341
gggggggggt tttttttttt tttttttttt tttttttttg ggggggg                47

SEQ ID NO: 342         moltype =   length =
SEQUENCE: 342
000

SEQ ID NO: 343         moltype =   length =
SEQUENCE: 343
```

-continued

```
000

SEQ ID NO: 344          moltype =   length =
SEQUENCE: 344
000

SEQ ID NO: 345          moltype = RNA  length = 10
FEATURE                 Location/Qualifiers
misc_feature            1..10
                        note = nucleic acid sequence according to formula (II)
source                  1..10
                        mol_type = other RNA
                        organism = synthetic construct
SEQUENCE: 345
ggttttttgg                                                    10

SEQ ID NO: 346          moltype = RNA  length = 11
FEATURE                 Location/Qualifiers
misc_feature            1..11
                        note = nucleic acid sequence according to formula (II)
source                  1..11
                        mol_type = other RNA
                        organism = synthetic construct
SEQUENCE: 346
ggtttttttg g                                                  11

SEQ ID NO: 347          moltype = RNA  length = 12
FEATURE                 Location/Qualifiers
misc_feature            1..12
                        note = nucleic acid sequence according to formula (II)
source                  1..12
                        mol_type = other RNA
                        organism = synthetic construct
SEQUENCE: 347
ggtttttttt gg                                                 12

SEQ ID NO: 348          moltype = RNA  length = 13
FEATURE                 Location/Qualifiers
misc_feature            1..13
                        note = nucleic acid sequence according to formula (II)
source                  1..13
                        mol_type = other RNA
                        organism = synthetic construct
SEQUENCE: 348
ggtttttttt tgg                                                13

SEQ ID NO: 349          moltype = RNA  length = 14
FEATURE                 Location/Qualifiers
misc_feature            1..14
                        note = nucleic acid sequence according to formula (II)
source                  1..14
                        mol_type = other RNA
                        organism = synthetic construct
SEQUENCE: 349
ggtttttttt ttgg                                               14

SEQ ID NO: 350          moltype = RNA  length = 15
FEATURE                 Location/Qualifiers
misc_feature            1..15
                        note = nucleic acid sequence according to formula (II)
source                  1..15
                        mol_type = other RNA
                        organism = synthetic construct
SEQUENCE: 350
ggtttttttt tttgg                                              15

SEQ ID NO: 351          moltype = RNA  length = 16
FEATURE                 Location/Qualifiers
misc_feature            1..16
                        note = nucleic acid sequence according to formula (II)
source                  1..16
                        mol_type = other RNA
                        organism = synthetic construct
SEQUENCE: 351
ggtttttttt ttttgg                                             16

SEQ ID NO: 352          moltype = RNA  length = 17
FEATURE                 Location/Qualifiers
misc_feature            1..17
```

```
                         note = nucleic acid sequence according to formula (II)
source                   1..17
                         mol_type = other RNA
                         organism = synthetic construct
SEQUENCE: 352
ggtttttttt tttttgg                                                    17

SEQ ID NO: 353           moltype = RNA  length = 18
FEATURE                  Location/Qualifiers
misc_feature             1..18
                         note = nucleic acid sequence according to formula (II)
source                   1..18
                         mol_type = other RNA
                         organism = synthetic construct
SEQUENCE: 353
ggtttttttt ttttttgg                                                   18

SEQ ID NO: 354           moltype = RNA  length = 19
FEATURE                  Location/Qualifiers
misc_feature             1..19
                         note = nucleic acid sequence according to formula (II)
source                   1..19
                         mol_type = other RNA
                         organism = synthetic construct
SEQUENCE: 354
ggtttttttt tttttttgg                                                  19

SEQ ID NO: 355           moltype =   length =
SEQUENCE: 355
000

SEQ ID NO: 356           moltype = RNA  length = 10
FEATURE                  Location/Qualifiers
misc_feature             1..10
                         note = nucleic acid sequence according to formula (II)
source                   1..10
                         mol_type = other RNA
                         organism = synthetic construct
SEQUENCE: 356
gggttttggg                                                            10

SEQ ID NO: 357           moltype = RNA  length = 11
FEATURE                  Location/Qualifiers
misc_feature             1..11
                         note = nucleic acid sequence according to formula (II)
source                   1..11
                         mol_type = other RNA
                         organism = synthetic construct
SEQUENCE: 357
gggtttttgg g                                                          11

SEQ ID NO: 358           moltype = RNA  length = 12
FEATURE                  Location/Qualifiers
misc_feature             1..12
                         note = nucleic acid sequence according to formula (II)
source                   1..12
                         mol_type = other RNA
                         organism = synthetic construct
SEQUENCE: 358
gggttttttg gg                                                         12

SEQ ID NO: 359           moltype = RNA  length = 13
FEATURE                  Location/Qualifiers
misc_feature             1..13
                         note = nucleic acid sequence according to formula (II)
source                   1..13
                         mol_type = other RNA
                         organism = synthetic construct
SEQUENCE: 359
gggttttttt ggg                                                        13

SEQ ID NO: 360           moltype = RNA  length = 14
FEATURE                  Location/Qualifiers
misc_feature             1..14
                         note = nucleic acid sequence according to formula (II)
source                   1..14
                         mol_type = other RNA
                         organism = synthetic construct
SEQUENCE: 360
```

```
gggttttttt tggg                                                  14

SEQ ID NO: 361        moltype = RNA  length = 15
FEATURE               Location/Qualifiers
misc_feature          1..15
                      note = nucleic acid sequence according to formula (II)
source                1..15
                      mol_type = other RNA
                      organism = synthetic construct
SEQUENCE: 361
gggttttttt ttggg                                                 15

SEQ ID NO: 362        moltype = RNA  length = 16
FEATURE               Location/Qualifiers
misc_feature          1..16
                      note = nucleic acid sequence according to formula (II)
source                1..16
                      mol_type = other RNA
                      organism = synthetic construct
SEQUENCE: 362
gggttttttt tttggg                                                16

SEQ ID NO: 363        moltype = RNA  length = 17
FEATURE               Location/Qualifiers
misc_feature          1..17
                      note = nucleic acid sequence according to formula (II)
source                1..17
                      mol_type = other RNA
                      organism = synthetic construct
SEQUENCE: 363
gggttttttt ttttggg                                               17

SEQ ID NO: 364        moltype = RNA  length = 18
FEATURE               Location/Qualifiers
misc_feature          1..18
                      note = nucleic acid sequence according to formula (II)
source                1..18
                      mol_type = other RNA
                      organism = synthetic construct
SEQUENCE: 364
gggttttttt tttttggg                                              18

SEQ ID NO: 365        moltype = RNA  length = 19
FEATURE               Location/Qualifiers
misc_feature          1..19
                      note = nucleic acid sequence according to formula (II)
source                1..19
                      mol_type = other RNA
                      organism = synthetic construct
SEQUENCE: 365
gggttttttt ttttttggg                                             19

SEQ ID NO: 366        moltype = RNA  length = 57
FEATURE               Location/Qualifiers
misc_feature          1..57
                      note = nucleic acid sequence according to formula (II)
source                1..57
                      mol_type = other RNA
                      organism = synthetic construct
SEQUENCE: 366
gggttttttt ttttttttgg gttttttttt ttttttgggt ttttttttt ttttggg    57

SEQ ID NO: 367        moltype = RNA  length = 42
FEATURE               Location/Qualifiers
misc_feature          1..42
                      note = nucleic acid sequence according to formula (II)
source                1..42
                      mol_type = other RNA
                      organism = synthetic construct
SEQUENCE: 367
gggttttttt ttttttttgg ggggtttttt ttttttttg gg                    42

SEQ ID NO: 368        moltype = RNA  length = 51
FEATURE               Location/Qualifiers
misc_feature          1..51
                      note = nucleic acid sequence according to formula (III)
source                1..51
                      mol_type = other RNA
                      organism = synthetic construct
```

```
SEQUENCE: 368
gggtttgggt ttgggtttgg gtttgggttt gggtttgggt ttgggtttgg g          51

SEQ ID NO: 369         moltype = RNA  length = 20
FEATURE                Location/Qualifiers
misc_feature           1..20
                       note = nucleic acid sequence according to formula (II) -
                        Short GU rich
source                 1..20
                       mol_type = other RNA
                       organism = synthetic construct
SEQUENCE: 369
ggtttttttt tttttttggg                                             20

SEQ ID NO: 370         moltype = RNA  length = 57
FEATURE                Location/Qualifiers
misc_feature           1..57
                       note = nucleic acid sequence according to formula (III)
source                 1..57
                       mol_type = other RNA
                       organism = synthetic construct
SEQUENCE: 370
cccttttttt ttttttttcc cttttttttt ttttttccct ttttttttt ttttccc     57

SEQ ID NO: 371         moltype = RNA  length = 51
FEATURE                Location/Qualifiers
misc_feature           1..51
                       note = nucleic acid sequence according to formula (III)
source                 1..51
                       mol_type = other RNA
                       organism = synthetic construct
SEQUENCE: 371
ccctttccct ttccctttcc ctttcccttt ccctttccct ttccctttcc c          51

SEQ ID NO: 372         moltype = RNA  length = 42
FEATURE                Location/Qualifiers
misc_feature           1..42
                       note = nucleic acid sequence according to formula (III)
source                 1..42
                       mol_type = other RNA
                       organism = synthetic construct
SEQUENCE: 372
cccttttttt ttttttttcc cccctttttt ttttttttc cc                    42

SEQ ID NO: 373         moltype = RNA  length = 60
FEATURE                Location/Qualifiers
misc_feature           1..60
                       note = nucleic acid sequence according to formula (IV)
source                 1..60
                       mol_type = other RNA
                       organism = synthetic construct
SEQUENCE: 373
tagcgaagct cttggaccta ggtttttttt tttttttggg tgcgttccta gaagtacacg  60

SEQ ID NO: 374         moltype = RNA  length = 120
FEATURE                Location/Qualifiers
misc_feature           1..120
                       note = nucleic acid sequence according to formula (IV)
source                 1..120
                       mol_type = other RNA
                       organism = synthetic construct
SEQUENCE: 374
tagcgaagct cttggaccta ggtttttttt tttttttggg tgcgttccta gaagtacacg  60
atcgcttcga gaacctggat ccaaaaaaaa aaaaaaaccc acgcaaggat cttcatgtgc  120

SEQ ID NO: 375         moltype = RNA  length = 229
FEATURE                Location/Qualifiers
misc_feature           1..229
                       note = nucleic acid sequence according to formula (IV)
source                 1..229
                       mol_type = other RNA
                       organism = synthetic construct
SEQUENCE: 375
gggagaaagc tcaagcttgg agcaatgccc gcacattgag gaaaccgagt tgcatatctc  60
agagtattgg cccccgtgta ggttattctt gacagacagt ggagcttatt cactcccagg  120
atccgagtcg catactacgg tactggtgac agacctaggt cgtcagttga ccagtccgcc  180
actagacgtg agtccgtcaa agcagttaga tgttacactc tattagatc             229

SEQ ID NO: 376         moltype = RNA  length = 547
```

-continued

```
FEATURE                Location/Qualifiers
misc_feature           1..547
                       note = nucleic acid sequence according to formula (IV)
source                 1..547
                       mol_type = other RNA
                       organism = synthetic construct
SEQUENCE: 376
gggagaaagc tcaagcttgg agcaatgccc gcacattgag gaaaccgagt tgcatatctc  60
agagtattgg cccccgtgta ggttattctt gacagacagt ggagcttatt cactcccagg  120
atccgagtcg catactacgg tactggtgac agacctaggt cgtcagttga ccagtccgcc  180
actagacgtg agtccgtcaa agcagttaga tgttacactc tattagatct cggattacag  240
ctggaaggag caggagtagt gttcttgctc taagtaccga gtgtgcccaa tacccgatca  300
gcttattaac gaacggctcc tcctcttaga ctgcagcgta agtgcggaat ctggggatca  360
aattactgac tgcctggatt accctcggac atataacctt gtagcacgct gttgctgtat  420
aggtgaccaa cgcccactcg agtagaccag ctctcttagt ccggacaatg ataggaggcg  480
cggtcaatct acttctggct agttaagaat aggctgcacc gacctctata agtagcgtgt  540
cctctag                                                            547

SEQ ID NO: 377         moltype = RNA  length = 1083
FEATURE                Location/Qualifiers
misc_feature           1..1083
                       note = nucleic acid sequence according to formula (IV)
source                 1..1083
                       mol_type = other RNA
                       organism = synthetic construct
SEQUENCE: 377
gggagaaagc tcaagcttgg agcaatgccc gcacattgag gaaaccgagt tgcatatctc  60
agagtattgg cccccgtgta ggttattctt gacagacagt ggagcttatt cactcccagg  120
atccgagtcg catactacgg tactggtgac agacctaggt cgtcagttga ccagtccgcc  180
actagacgtg agtccgtcaa agcagttaga tgttacactc tattagatct cggattacag  240
ctggaaggag caggagtagt gttcttgctc taagtaccga gtgtgcccaa tacccgatca  300
gcttattaac gaacggctcc tcctcttaga ctgcagcgta agtgcggaat ctggggatca  360
aattactgac tgcctggatt accctcggac atataacctt gtagcacgct gttgctgtat  420
aggtgaccaa cgcccactcg agtagaccag ctctcttagt ccggacaatg ataggaggcg  480
cggtcaatct acttctggct agttaagaat aggctgcacc gacctctata agtagcgtgt  540
cctctagagc tacgcaggtt cgcaataaaa gcgttgatta gtgtgcatag aacagacctc  600
ttattcggtg aaacgccaga atgctaaatt ccaataactc ttcccaaaac gcgtacggcc  660
gaagacgcgc gcttatcttg tgtacgttct cgcacatgga agaatcagcg ggcatggtgg  720
tagggcaata ggggagctgg gtagcagcga aaaagggccc ctgcgcacgt agcttcgctg  780
ttcgtctgaa acaacccggc atccgttgta gcgatcccgt tatcagtgtt attcttgtgc  840
gcactaagat tcatggtgta gtcgacaata acagcgtctt ggcagattct ggtcacgtgc  900
cctatgcccg ggcttgtgcc tctcaggtgc acagcgatac ttaaagcctt caaggtactc  960
gacgtgggta ccgattcgtg acacttccta agattattcc actgtgttag ccccgcaccg  1020
ccgacctaaa ctggtccaat gtatacgcat tcgctgagcg gatcgataat aaaagcttga  1080
att                                                                1083

SEQ ID NO: 378         moltype = RNA  length = 229
FEATURE                Location/Qualifiers
misc_feature           1..229
                       note = nucleic acid sequence according to formula (IV)
source                 1..229
                       mol_type = other RNA
                       organism = synthetic construct
SEQUENCE: 378
gggagaaagc tcaagcttat ccaagtaggc tggtcacctg tacaacgtag ccggtatttt  60
tttttttttt tttttttga ccgtctcaag gtccaagtta gtctgcctat aaaggtgcgg  120
atccacagct gatgaaagac ttgtgcggta cggttaatct ccccttttt tttttttttt  180
tttttagtaa atgcgtctac tgaatccagc gatgatgctg gcccagatc              229

SEQ ID NO: 379         moltype = RNA  length = 546
FEATURE                Location/Qualifiers
misc_feature           1..546
                       note = nucleic acid sequence according to formula (IV)
source                 1..546
                       mol_type = other RNA
                       organism = synthetic construct
SEQUENCE: 379
gggagaaagc tcaagcttat ccaagtaggc tggtcacctg tacaacgtag ccggtatttt  60
tttttttttt tttttttga ccgtctcaag gtccaagtta gtctgcctat aaaggtgcgg  120
atccacagct gatgaaagac ttgtgcggta cggttaatct ccccttttt tttttttttt  180
tttttagtaa atgcgtctac tgaatccagc gatgatgctg gcccagatct tcgaccacaa  240
gtgcatatag tagtcatcga gggtcgcctt tttttttttt tttttttttt tggcccagtt  300
ctgagacttc gctagagact acagttacag ctgcagtagt aaccactgcg gctattgcag  360
gaaatcccgt tcaggttttt tttttttttt ttttttccgc tcactatgat taagaaccag  420
gtggagtgtc actgctctcg aggtctcacg agagcgctcg atacagtcct tggaagaatc  480
tttttttttt tttttttttt ttgtgcgacg atcacagaga acttctattc atgcaggtct  540
gctcta                                                             546

SEQ ID NO: 380         moltype = RNA  length = 1083
```

```
FEATURE                Location/Qualifiers
misc_feature           1..1083
                       note = nucleic acid sequence according to formula (IV)
source                 1..1083
                       mol_type = other RNA
                       organism = synthetic construct
SEQUENCE: 380
gggagaaagc tcaagcttat ccaagtaggc tggtcacctg tacaacgtag ccggtatttt  60
tttttttttt tttttttga ccgtctcaag gtccaagtta gtctgcctat aaaggtgcgg  120
atccacagct gatgaaagac ttgtgcggta cggttaatct cccctttttt tttttttttt  180
tttttagtaa atgcgtctac tgaatccagc gatgatgctg gcccagatct tcgaccacaa  240
gtgcatatag tagtcatcga gggtcgcctt tttttttttt tttttttttt tggcccagtt  300
ctgagacttc gctagagact acagttacag ctgcagtagt aaccactgcg gctattgcag  360
gaaatcccgt tcaggttttt tttttttttt ttttttccgc tcactatgat taagaaccag  420
gtggagtgtc actgctctcg aggtctcacg agagcgctcg atacagtcct tggaagaatc  480
tttttttttt tttttttttt ttgtgcgacg atcacagaga acttctattc atgcaggtct  540
gctctagaac gaactgacct gacgcctgaa cttatgagcg tgcgtatttt tttttttttt  600
tttttttttc ctcccaacaa atgtcgatca atagctgggc tgttggagac gcgtcagcaa  660
atgccgtggc tccataggac gtgtagactt ctattttttt tttttttttt ttttcccggg  720
accacaaata atattcttgc ttggttgggc gcaagggccc cgtatcaggt cataaacggg  780
tacatgttgc acaggctcct tttttttttt tttttttttt ttcgctgagt tattccggtc  840
tcaaaagacg gcagacgtca gtcgacaaca cggtctaaag cagtgctaca atctgccgtg  900
ttcgtgtttt tttttttttt ttttttgtga acctacacgg cgtgcactgt agttcgcaat  960
tcatagggta ccggctcaga gttatgcctt ggttgaaaac tgcccagcat actttttttt  1020
tttttttttt ttcatattcc catgctaagc aagggatgcc gcgagtcatg ttaagcttga  1080
att                                                                1083

SEQ ID NO: 381         moltype = RNA  length = 59
FEATURE                Location/Qualifiers
misc_feature           1..59
                       note = nucleic acid sequence according to formula (V)
source                 1..59
                       mol_type = other RNA
                       organism = synthetic construct
SEQUENCE: 381
tagcgaagct cttggaccta cctttttttt ttttttccct gcgttcctag aagtacacg   59

SEQ ID NO: 382         moltype = RNA  length = 120
FEATURE                Location/Qualifiers
misc_feature           1..120
                       note = nucleic acid sequence according to formula (V)
source                 1..120
                       mol_type = other RNA
                       organism = synthetic construct
SEQUENCE: 382
tagcgaagct cttggaccta cctttttttt tttttttccc tgcgttccta gaagtacacg  60
atcgcttcga gaacctggat ggaaaaaaaa aaaaaaaggg acgcaaggat cttcatgtgc  120

SEQ ID NO: 383         moltype = RNA  length = 22
FEATURE                Location/Qualifiers
misc_feature           1..22
                       note = Description of sequence: A synthetic stabilizing
                        sequence
misc_feature           5..9
                       note = N is A, U, C, or G and is either present or absent.
misc_feature           14..17
                       note = Y is either present or absent
source                 1..22
                       mol_type = other RNA
                       organism = synthetic construct
SEQUENCE: 383
yccannnnnc ccwyyyytcy cc                                           22

SEQ ID NO: 384         moltype = RNA  length = 1698
FEATURE                Location/Qualifiers
misc_feature           1..1698
                       note = PR8 H1 mRNA
source                 1..1698
                       mol_type = other RNA
                       organism = synthetic construct
SEQUENCE: 384
atgaaggcca acctgctcgt gctgctgtgc gccctcgcgg ccgccgacgc cgacaccatc  60
tgcatcggct accacgccaa caacagcacc gacacggtcg acaccgtgct ggagaagaac  120
gtgaccgtca cccactccgt gaacctgctc gaggacagcc acaacgggaa gctgtgccgg  180
ctgaagggca tcgcgcccct ccagctgggg aagtgcaaca tcgccggctg gctgctcggg  240
aacccggagt gcgacccccct gctgcccgtg cgctcctgga gctacatcgt cgagacgccc  300
aactccgaga acggcatctg ctacccgggc gacttcatcg actacgagga gctccgggag  360
cagctgagct ccgtgagctc cttcgagcgc ttcgagatct tccccaagga gagctcctgg  420
cccaaccaca acaccaacgg ggtgaccgcc gcctgcagcc acgagggcaa gtccagcttc  480
```

-continued

```
taccggaacc tgctctggct gaccgagaag gaggggtcct accccaagct gaagaacagc  540
tacgtcaaca agaagggcaa ggaggtgctc gtgctgtggg ggatccacca cccgcccaac  600
tccaaggagc agcagaacct gtaccagaac gagaacgcgt acgtcagcgt ggtgacgtcc  660
aactacaacc gccggttcac ccccgagatc gccgagcgcc ccaaggtccg ggaccaggcc  720
ggccgcatga actactactg gaccctcctg aagccgggcg acaccatcat cttcgaggcc  780
aacgggaacc tgatcgcccc gatgtacgcg ttcgccctca gccggggctt cgggagcggc  840
atcatcacgt ccaacgccag catgcacgag tgcaacacca agtgccagac ccccctgggc  900
gccatcaact ccagcctgcc ctaccagaac atccacccgg tgaccatcgg ggagtgcccc  960
aagtacgtgc gctccgccaa gctccggatg gtcacgggcc tgcgcaacaa ccccagcatc  1020
cagtcccggg ggctgttcgg cgcgatcgcc gggttcatcg agggcggctg gaccgggatg  1080
atcgacggct ggtacgggta ccaccaccag aacgagcagg gcagcgggta cgccgccgac  1140
cagaagtcca cccagaacgc catcaacggc atcaccaaca aggtgaacac ggtgatcgag  1200
aagatgaaca tccagttcac cgcggtcggc aaggagttca acaagctcga gaagcgcatg  1260
gagaacctga acaagaaggt ggacgacggg ttcctggaca tctggaccta caacgccgag  1320
ctcctggtgc tgctcgagaa cgagcggacc ctggacttcc acgacagcaa cgtcaagaac  1380
ctgtacgaga aggtgaagtc ccagctcaag aacaacgcca aggagatcgg caacgggtgc  1440
ttcgagttct accacaagtg cgacaacgag tgcatggaga gcgtccgcaa cggcacgtac  1500
gactacccca agtactccga ggagagcaag ctgaaccggg agaaggtgga cggggtgaag  1560
ctggagtcca tgggcatcta ccagatcctc gccatctaca gcaccgtcgc ctccagcctg  1620
gtgctgctgg tgtccctcgg cgcgatcagc ttctggatgt gcagcaacgg gtccctgcag  1680
tgccgcatct gcatctga                                                1698

SEQ ID NO: 385          moltype = RNA  length = 1161
FEATURE                 Location/Qualifiers
misc_feature            1..1161
                        note = Ovalbumin (control) mRNA
source                  1..1161
                        mol_type = other RNA
                        organism = synthetic construct
SEQUENCE: 385
atgggcagca tcggggccgc gtcgatggag ttctgcttcg acgtgttcaa ggagctgaag  60
gtccaccacg ccaacgagaa catcttctac tgcccgatcg ccatcatgag cgcgctcgcc  120
atggtgtacc tgggcgccaa ggacagcacc cggacgcaga tcaacaaggt ggtccgcttc  180
gacaagctgc ccggcttcgg ggactcgatc gaggcgcagt gcggcaccag cgtgaacgtg  240
cacagctcgc tccgggacat cctgaaccag atcaccaagc cgaacgacgt ctacagcttc  300
agcctggcct cgcggctcta cgccgaggag cgctacccga tcctgcccga gtacctgcag  360
tgcgtgaagg agctctaccg gggcgggctg gagccgatca acttccagac ggcggccgac  420
caggcccggg agctgatcaa cagctgggtg gagagccaga ccaacggcat catccgcaac  480
gtcctccagc cgtcgagcgt ggacagccag accgcgatgg tgctggtcaa cgccatcgtg  540
ttcaagggcc tgtgggagaa gacgttcaag gacgaggaca cccaggccat gcccttccgg  600
gtgaccgagc aggagtcgaa gccggtccag atgatgtacc agatcgggct cttccgggtg  660
gcgagcatgg ccagcgagaa gatgaagatc ctggagctgc cgttcgcctc gggcacgatg  720
agcatgctcg tgctgctgcc cgacgaggtc agcggcctcg agcagctgga gtcgatcatc  780
aacttcgaga agctgaccga gtggaccagc agcaacgtga tggaggagcg caagatcaag  840
gtgtacctcc cgcggatgaa gatggaggag aagtacaacc tgacgtcggt cctgatggcg  900
atggggatca ccgacgtgtt cagcagctcg gccaacctca gcggcatcag ctcggccgag  960
agcctgaaga tcagccaggc ggtgcacgcc gcccacgcgg agatcaacga ggccggccgg  1020
gaggtcgtgg ggtcggccga ggcgggcgtg gacgccgcca gcgtcagcga ggagttccgc  1080
gcggaccacc cgttcctgtt ctgcatcaag cacatcgcca ccaacgccgt gctcttcttc  1140
ggccggtgcg tgtcgccctg a                                            1161
```